United States Patent
Gavelle et al.

(10) Patent No.: US 10,308,659 B2
(45) Date of Patent: Jun. 4, 2019

(54) PYRIDINE DERIVATIVES

(71) Applicant: Hoffmann-La Roche Inc., Little Falls, NJ (US)

(72) Inventors: Olivier Gavelle, Hagenthal-le-Bas (FR); Uwe Grether, Efringen-Kirchen (DE); Atsushi Kimbara, Shizuoka (JP); Matthias Nettekoven, Grenzach-Wyhlen (DE); Roever Stephan, Inzlingen (DE); Mark Rogers-Evans, Bottmingen (CH); Didier Rombach, Mulhouse (FR); Tanja Schulz-Gasch, Ziefen (CH)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/868,305

(22) Filed: Sep. 28, 2015

(65) Prior Publication Data

US 2016/0016968 A1  Jan. 21, 2016

Related U.S. Application Data

(63) Continuation of application No. PCT/EP2014/055797, filed on Mar. 24, 2014.

(30) Foreign Application Priority Data

Mar. 26, 2013 (EP) ..................... 13161176

(51) Int. Cl.
| | | |
|---|---|---|
| C07D 413/04 | (2006.01) | |
| C07D 491/107 | (2006.01) | |
| C07D 413/14 | (2006.01) | |
| C07D 403/04 | (2006.01) | |
| C07D 401/04 | (2006.01) | |
| C07D 401/14 | (2006.01) | |

(52) U.S. Cl.
CPC ....... *C07D 491/107* (2013.01); *C07D 401/04* (2013.01); *C07D 401/14* (2013.01); *C07D 403/04* (2013.01); *C07D 413/04* (2013.01); *C07D 413/14* (2013.01)

(58) Field of Classification Search
CPC .................................. C07D 413/04
USPC ....................... 546/269.4; 514/340
See application file for complete search history.

(56) References Cited

U.S. PATENT DOCUMENTS

| | | |
|---|---|---|
| 9,303,012 B2 | 4/2016 | Bendels et al. |
| 9,321,727 B2 | 4/2016 | Bissantz et al. |
| 9,522,886 B2 | 12/2016 | Frei et al. |
| 2012/0316147 A1 | 12/2012 | Bissantz |
| 2016/0137606 A1 | 5/2016 | Bissantz et al. |
| 2016/0376237 A1 | 12/2016 | Gobbi et al. |
| 2016/0376262 A1 | 12/2016 | Gabbi et al. |

FOREIGN PATENT DOCUMENTS

| | | |
|---|---|---|
| JP | 2010-517934 A | 5/2010 |
| WO | 03/082191 A2 | 10/2003 |
| WO | 2008/019357 A2 | 2/2008 |
| WO | 2009/051705 A1 | 4/2009 |
| WO | 2012/168350 A1 | 12/2012 |
| WO | 2013/068306 A1 | 5/2013 |
| WO | 2014/005968 A1 | 1/2014 |
| WO | 2014/086705 A1 | 6/2014 |
| WO | 2014/086805 A1 | 6/2014 |
| WO | 2014/086806 A1 | 6/2014 |
| WO | 2014/086807 | 6/2014 |
| WO | 2014/135507 A1 | 9/2014 |

OTHER PUBLICATIONS

Bundgaard, Design of Prodrugs, p. 1, 1985.*
Banker et al., Prodrugs, Modern Pharmaceutics, 3rd edition, Revised and Expanded, pp. 451 and 596.*
Jordan "Tamoxifen . . . " Nature Rev. v.2, p. 205-213 (2003).*
Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Balant ed in Wolff et al. Burger's Medicinal Chemistry and Drug Discovery. 5th ed. vol. 1: Principles and Practice. pp. 949-982, 1996.*
Intl. Search Report WO 2014/154612, PCT/EP2014/055797.
Nettekoven et al., "Highly potent and selective cannabinoid receptor 2 agonists: initial hit optimization of an adamantyl hit series identified from high-through-put screening" Bioorg Med Chem Lett. 23(5):1177-81 ( 2013).
Nettekoven et al., "Novel Triazolopyrimidine-Derived Cannabinoid Receptor 2 Agonists as Potential Treatment for Inflammatory Kidney Diseases" ChemMedChem. 11(2):179-89 (2016).

(Continued)

*Primary Examiner* — Patricia L Morris

(74) *Attorney, Agent, or Firm* — Zong-Qiang Bill Tian; Genentech, Inc.

(57) ABSTRACT

The invention relates to a compound of formula (I)

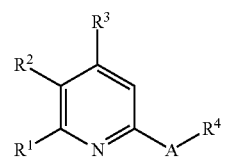

wherein A and $R^1$ to $R^4$ are defined as in the description and in the claims. The compound of formula (I) can be used as a medicament.

10 Claims, No Drawings

(56) References Cited

OTHER PUBLICATIONS

Slavik et al., "Discovery of a high affinity and selective pyridine analog as a potential positron emission tomography imaging agent for cannabinoid type 2 receptor" J Med Chem. 58(10):4266-77 (2015).

* cited by examiner

PYRIDINE DERIVATIVES

CROSS-REFERENCE TO RELATED APPLICATIONS

This application is a continuation application of International Application No. PCT/EP2014/055797 filed on Mar. 24, 2014, which claims priority to European Patent Application No. 13161176.6, filed on Mar. 26, 2013, the entire contents of which are incorporated herein by reference.

The present invention relates to organic compounds useful for therapy and/or prophylaxis in a mammal, and in particular to compounds that are preferential agonists of the Cannabinoid Receptor 2.

The invention relates in particular to a compound of formula (I)

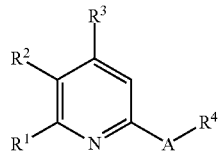

(I)

wherein
A is A1, A2, A3, A4 A5, A6, A7 or A8

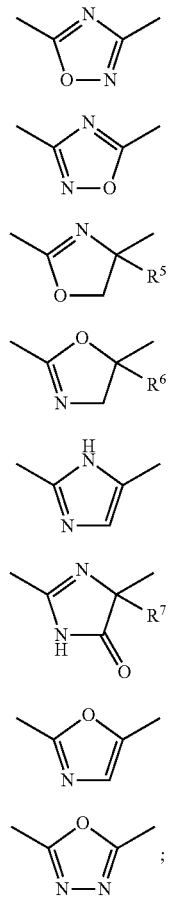

$R^1$ is hydrogen or halogen;
$R^2$ is halogen, cycloalkyl, haloazetidinyl, 6-oxa-1-azaspiro[3.3]heptyl or alkylsulfonyl;
$R^3$ is —$OR^8$, pyrrolidinyl, halopyrrolidinyl, hydroxypyrrolidinyl, morpholinyl, cycloalkylsulfonyl, alkoxyazetidinyl, 2-oxa-6-aza-spiro[3.3]heptyl or 2-oxa-7-azaspiro[3.4]heptyl;
$R^4$ is hydrogen, alkyl, hydroxyalkyl, alkoxyalkyl, haloalkyl, cycloalkyl, hydroxycycloalkyl, alkylcycloalkyl, aminocarbonylcycloalkyl, phenyl, phenylalkyl, alkyloxetanyl, azetidinyl or aminooxetanyl;
$R^5$ is hydrogen, alkyl or alkyloxadiazolyl;
or $R^4$ and $R^5$, together with the carbon atom to which they are attached, form cycloalkyl;
$R^6$ is alkyl;
$R^7$ is alkyl; and
$R^8$ is haloalkyl, alkoxyalkyl, cycloalkylalkyl, haloalkyl, halophenyl, oxetanyl, oxetanylalkyl, alkyloxetanylalkyl, tetrahydrofuranyl, tetrahydrofuranylalkyl, alkylsulfonylphenyl, alkylpyrrolidinyl, alkylpyrrolidinylalkyl, azetidinyl, morpholinylalkyl, tetrahydropyranyl, pyrrolidinylalkyl, piperidinyl, piperidinylalkyl, alkylpiperidinylalkyl, alkylpiperidinyl, dialkylaminoalkyl, pyridinylalkyl, halooxetanylalkyl, dialkyloxazolylalkyl, alkyloxazolylalkyl, halopyridinylalkyl or morpholinyl;
or a pharmaceutically acceptable salt or ester thereof.

The compound of formula (I) is particularly useful in the treatment or prophylaxis of e.g. pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, amyotrophic lateral sclerosis, multiple sclerosis, Alzheimer's disease, Parkinson's disease, stroke, transient ischemic attack or uveitis.

The compound of formula (I) is in particular useful in the treatment or prophylaxis of diabetic retinopathy, retinal vein occlusion or uveitis.

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages and T-cells (Ashton, J. C. et al. Curr Neuropharmacol 2007, 5(2), 73-80; Miller, A. M. et al. Br J Pharmacol 2008, 153(2), 299-308; Centonze, D., et al. Curr Pharm Des 2008, 14(23), 2370-42), and in the gastrointestinal system (Wright, K. L. et al. Br J Pharmacol 2008, 153(2), 263-70). The CB2 receptor is also widely distributed in the brain where it is found primarily on microglia and not neurons (Cabral, G. A. et al. Br J Pharmacol 2008, 153(2): 240-51).

The interest in CB2 receptor agonists has been steadily on the rise during the last decade (currently 30-40 patent applications/year) due to the fact that several of the early compounds have been shown to have beneficial effects in pre-clinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A. et al. J Leukoc Biol 2005, 78(6), 1192-7), ischemia/reperfusion injury (Pacher, P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6), liver fibrosis (Julien, B. et al. Gastroenterology 2005, 128(3), 742-55; Munoz-Luque, J. et al. J Pharmacol Exp Ther 2008, 324(2), 475-83).

Ischemia/reperfusion (I/R) injury is the principal cause of tissue damage occurring in conditions such as stroke, myocardial infarction, cardiopulmonary bypass and other vascular surgeries, and organ transplantation, as well as a major mechanism of end-organ damage complicating the course of circulatory shock of various etiologies. All these conditions are characterized by a disruption of normal blood supply resulting in an insufficient tissue oxygenation. Re-oxygenation e.g., reperfusion is the ultimate treatment to restore normal tissue oxygenation. However the absence of oxygen and nutrients from blood creates a condition in which the restoration of circulation results in further tissue damage. The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane.

Remote ischemic preconditioning (RIPC) represents a strategy for harnessing the body's endogenous protective capabilities against the injury incurred by ischemia and reperfusion. It describes the intriguing phenomenon in which transient non-lethal ischemia and reperfusion of one organ or tissue confers resistance to a subsequent episode of "lethal" ischemia reperfusion injury in a remote organ or tissue. The actual mechanism through which transient ischemia and reperfusion of an organ or tissue confers protection is currently unknown although several hypotheses have been proposed.

The humoral hypothesis proposes that the endogenous substance (such as adenosine, bradykinin, opioids, CGRP, endocannabinoids, Angiotensin I or some other as yet unidentified humoral factor) generated in the remote organ or tissue enters the blood stream and activates its respective receptor in the target tissue and thereby recruiting the various intracellular pathways of cardioprotection implicated in ischemic preconditioning.

Recent data indicates that endocannabinnoids and their receptors, in particular CB2 might be involved in pre-conditioning and contribute to prevent reperfusion injury by downregulation of the inflammatory response (Pacher, P. et al. Br J Pharmacol 2008, 153(2), 252-62). Specifically, recent studies using CB2 tool agonists demonstrated the efficacy of this concept for reducing the PR injury in the heart (Defer, N. et al. Faseb J 2009, 23(7), 2120-30), the brain (Zhang, M. et al. J Cereb Blood Flow Metab 2007, 27(7), 1387-96), the liver (Batkai, S. et al. Faseb J 2007, 21(8), 1788-800) and the kidney (Feizi, A. et al. Exp Toxicol Pathol 2008, 60(4-5), 405-10).

Moreover, over the last few years, a growing body of literature indicates that CB2 can also be of interest in sub-chronic and chronic setting. Specific upregulation of CB1 and CB2 has been shown to be associated in animal models of chronic diseases associated with fibrosis (Garcia-Gonzalez, E. et al. Rheumatology (Oxford) 2009, 48(9), 1050-6; Yang, Y. Y. et al. Liver Int 2009, 29(5), 678-85) with a relevant expression of CB2 in myofibroblasts, the cells responsible for fibrosis progression.

Activation of CB2 receptor by selective CB2 agonist has in fact been shown to exert anti-fibrotic effect in diffuse systemic sclerosis (Garcia-Gonzalez, E. et al. Rheumatology (Oxford) 2009, 48(9), 1050-6) and CB2 receptor has emerged as a critical target in experimental dermal fibrosis (Akhmetshina, A. et al. Arthritis Rheum 2009, 60(4), 1129-36) and in liver pathophysiology, including fibrogenesis associated with chronic liver diseases (Lotersztajn, S. et al. Gastroenterol Clin Biol 2007, 31(3), 255-8; Mallat, A. et al. Expert Opin Ther Targets 2007, 11(3), 403-9; Lotersztajn, S. et al. Br J Pharmacol 2008, 153(2), 286-9).

The compounds of the invention bind to and modulate the CB2 receptor and have lower CB1 receptor activity.

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl more particularly methyl, ethyl, propyl, isopropyl, isobutyl, tert.-butyl and isopentyl. Particular examples of alkyl are methyl, ethyl, isopropyl, isobutyl and tert.-butyl, in particular methyl, ethyl and tert.-butyl.

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl and cyclohexyl, cycloheptyl and cyclooctyl. Particular examples of "cycloalkyl" are cyclopropyl, cyclopentyl and cyclohexyl, in particular cyclopropyl and cyclohexyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert-butoxy. Particular "alkoxy" are methoxy, ethoxy and butoxy, and in particular methoxy and butoxy.

The term "oxy", alone or in combination, signifies the —O— group.

The terms "halogen" or "halo", alone or in combination, signifies fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to four halogens, i.e. one, two, three or four halogens. A particular "halogen" is fluorine.

The term "haloalkyl", alone or in combination, denotes an alkyl group substituted with at least one halogen, particularly substituted with one to five halogens, particularly one to three halogens. Particular "haloalkyl" are trifluoroethyl, trifluoromethyl, trifluoropropyl and difluoroethyl, more particularly trifluoroethyl and difluoroethyl.

A particular "halophenyl" is fluorophenyl. A particular haloazetidinyl is difluoroazetidinyl, in particular 3,3-difluoro-azetidin-1-yl. A particular halopyrrolidinyl is difluoropyrrolidinyl, in partiuclar 3,3-difluoro-pyrrolidin-1-yl, or tetrafluoropyrrolidinyl, in particular 3,3,4,4-tetrafluoropyrrolidin-1-yl. A particular halooxetanyl is fluorooxetanyl. A particular halopyridinyl is fluoropyridinyl.

The terms "hydroxyl" and "hydroxy", alone or in combination, signify the —OH group.

The term "carbonyl", alone or in combination, signifies the —C(O)— group.

The term "amino", alone or in combination, signifies the primary amino group (—NH$_2$), the secondary amino group (—NH—), or the tertiary amino group (—N—).

The term "sulfonyl", alone or in combination, signifies the —S(O)$_2$— group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that the compound of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compound of general formula (I), similar to the metabolically labile esters, which are capable of producing the parent compound of general formula (I) in vivo, are within the scope of this invention.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3$^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The invention relates in particular to:

A compound of formula (I) wherein A is A1 or A2;

A compound of formula (I) wherein $R^1$ is hydrogen or chloro;

A compound of formula (I) wherein $R^1$ is hydrogen;

A compound of formula (I) wherein $R^2$ is cycloalkyl, bishalo-azetidinyl or alkylsulphonyl;

A compound of formula (I) wherein $R^2$ is cycloalkyl;

A compound of formula (I) wherein $R^2$ is cyclopropyl;

A compound of formula (I) wherein $R^3$ is —OR$^8$ or pyrrolidinyl;

A compound of formula (I) wherein $R^3$ is —OR$^8$;

A compound of formula (I) wherein $R^4$ is alkyl;

A compound of formula (I) wherein $R^4$ is butyl, in particular tert.-butyl;

A compound of formula (I) wherein $R^5$ is hydrogen, ethyl or methyloxadiazolyl, or $R^4$ and $R^5$, together with the carbon atom to which they are attached, form cyclohexyl;

A compound of formula (I) wherein $R^6$ is methyl;

A compound of formula (I) wherein $R^7$ is methyl or isopropyl;

A compound of formula (I) wherein $R^8$ is haloalkyl, alkoxyalkyl, cycloalkylalkyl, haloalkyl, halophenyl, oxetanyl, oxetanylalkyl, alkyloxetanylalkyl, tetrahydrofuranyl, tetrahydrofuranylalkyl, alkylsulfonylphenyl, alkylpyrrolidinyl, alkylpyrrolidinylalkyl, azetidinyl, morpholinylalkyl, tetrahydropyranyl, pyrrolidinylalkyl, piperidinyl, piperidinylalkyl, alkylpiperidinylalkyl, alkylpiperidinyl, dialkylaminoalkyl, pyridinylalkyl, halooxetanylalkyl, dialkyloxazolylalkyl or alkyloxazolylalkyl;

A compound of formula (I) wherein $R^8$ is haloalkyl, alkoxyalkyl, halophenyl, alkylsulphonyl, sulphonylphenyl, alkylpyrrolidinyl, alkoxyalkylpyrrolidinyl, 2-oxa-6-azaspiro[3.3]heptanyl, alkyloxetanylalkyl, oxetanylalkyl, tetrahydrofuranyl, tetrahydrofuranylalkyl, tetrahydropyranyl or alkyloxadiazolyl;

A compound of formula (I) wherein $R^8$ is haloalkyl, alkoxyalkyl, halophenyl, alkyloxetanylalkyl, oxetanylalkyl, tetrahydrofuranyl, tetrahydrofuranylalkyl or tetrahydropyranyl;

A compound of formula (I) wherein $R^8$ is trifluoromethyl, ethoxyethyl, methoxybutyl, fluorophenyl, oxetanylmehtyl, methyloxetanylmehtyl, tetrahydrofuranyl, tetrahydrofuranylmehtyl or tetrahydropyranyl;

A compound of formula (I) wherein $R^8$ is haloalkyl, alkoxyalkyl, halophenyl, alkyloxetanylalkyl, oxetanylalkyl, tetrahydrofuranyl, tetrahydrofuranylalkyl, tetrahydropyranyl, halopyridinylalkyl or morpholinyl; and A compound of formula (I) wherein $R^8$ is trifluoromethyl, ethoxyethyl, methoxybutyl, fluorophenyl, oxetanylmehtyl, methyloxetanylmehtyl, tetrahydrofuranyl, tetrahydrofuranylmehtyl, tetrahydropyranyl, difluoroethyl, fluoropyridinylmethyl or morpholinyl.

Particular $R^4$ are methyl, ethyl, isopropyl, tert.-butyl, trifluoromethyl, cyclopropyl, cyclopentyl, methylcyclopropyl, aminocarbonylcyclopropyl, hydroxymehtyl, hydroxypropyl, hydroxycyclopropyl, methoxymethyl, phenyl, phenylmethyl, methyloxetanyl, azetidinyl, methyloxetanyl and aminooxetanyl.

In the definition of R⁴, tert.-butyl is a particular butyl.

The invention further relates to a compound of formula (I) selected from:

5-[5-cyclopropyl-4-(cyclopropylmethoxy)pyridin-2-yl]-3-methyl-1,2,4-oxadiazole;
5-[5-cyclopropyl-4-(cyclopropylmethoxy)pyridin-2-yl]-3-phenyl-1,2,4-oxadiazole;
3-cyclopropyl-5-[5-cyclopropyl-4-(cyclopropylmethoxy)pyridin-2-yl]-1,2,4-oxadiazole;
3-cyclopentyl-5-[5-cyclopropyl-4-(cyclopropylmethoxy)pyridin-2-yl]-1,2,4-oxadiazole;
3-benzyl-5-[5-cyclopropyl-4-(cyclopropylmethoxy)pyridin-2-yl]-1,2,4-oxadiazole;
3-tert-butyl-5-[5-cyclopropyl-4-(cyclopropylmethoxy)pyridin-2-yl]-1,2,4-oxadiazole;
3-cyclopropyl-5-[5-cyclopropyl-4-(2,2,2-trifluoroethoxy)pyridin-2-yl]-1,2,4-oxadiazole;
5-[5-cyclopropyl-4-(2,2,2-trifluoroethoxy)pyridin-2-yl]-3-(trifluoromethyl)-1,2,4-oxadiazole;
5-cyclopropyl-3-[5-cyclopropyl-4-(cyclopropylmethoxy)pyridin-2-yl]-1,2,4-oxadiazole;
5-tert-butyl-3-[5-cyclopropyl-4-(cyclopropylmethoxy)pyridin-2-yl]-1,2,4-oxadiazole;
2-[5-cyclopropyl-4-(cyclopropylmethoxy)pyridin-2-yl]-4,4-diethyl-5H-1,3-oxazole;
3-[5-cyclopropyl-4-(cyclopropylmethoxy)pyridin-2-yl]-5-(methoxymethyl)-1,2,4-oxadiazole;
3-[5-cyclopropyl-4-(cyclopropylmethoxy)pyridin-2-yl]-5-ethyl-1,2,4-oxadiazole;
3-[5-cyclopropyl-4-(cyclopropylmethoxy)pyridin-2-yl]-5-propan-2-yl-1,2,4-oxadiazole;
3-cyclopropyl-5-[5-(3,3-difluoroazetidin-1-yl)-4-(2,2,2-trifluoroethoxy)pyridin-2-yl]-1,2,4-oxadiazole;
5-[5-(3,3-difluoroazetidin-1-yl)-4-(2,2,2-trifluoroethoxy)pyridin-2-yl]-3-methyl-1,2,4-oxadiazole;
3-tert-butyl-5-[5-(3,3-difluoroazetidin-1-yl)-4-(2,2,2-trifluoroethoxy)pyridin-2-yl]-1,2,4-oxadiazole;
[3-[5-cyclopropyl-4-(cyclopropylmethoxy)pyridin-2-yl]-1,2,4-oxadiazol-5-yl]methanol;
3-[5-cyclopropyl-4-(cyclopropylmethoxy)pyridin-2-yl]-5-(trifluoromethyl)-1,2,4-oxadiazole;
(4S)-4-tert-butyl-2-[5-cyclopropyl-4-(cyclopropylmethoxy)pyridin-2-yl]-4,5-dihydro-1,3-oxazole;
2-[5-cyclopropyl-4-(cyclopropylmethoxy)pyridin-2-yl]-4-ethyl-4,5-dihydro-1,3-oxazole;
2-[5-cyclopropyl-4-(cyclopropylmethoxy)pyridin-2-yl]-3-oxa-1-azaspiro[4.5]dec-1-ene;
1-[3-[5-cyclopropyl-4-(cyclopropylmethoxy)pyridin-2-yl]-1,2,4-oxadiazol-5-yl]cyclopropan-1-ol;
3-[5-cyclopropyl-4-(cyclopropylmethoxy)pyridin-2-yl]-5-(1-methylcyclopropyl)-1,2,4-oxadiazole;
1-[3-[5-cyclopropyl-4-(cyclopropylmethoxy)pyridin-2-yl]-1,2,4-oxadiazol-5-yl]cyclopropane-1-carboxamide;
2-[3-[5-cyclopropyl-4-(cyclopropylmethoxy)pyridin-2-yl]-1,2,4-oxadiazol-5-yl]propan-2-ol;
2-[5-cyclopropyl-4-(2,2,2-trifluoroethoxy)pyridin-2-yl]-4,4-diethyl-5H-1,3-oxazole;
3-[5-cyclopropyl-4-(cyclopropylmethoxy)pyridin-2-yl]-5-(3-methyloxetan-3-yl)-1,2,4-oxadiazole;
5-(azetidin-3-yl)-3-[5-cyclopropyl-4-(cyclopropylmethoxy)pyridin-2-yl]-1,2,4-oxadiazole;
2-[5-(3,3-difluoroazetidin-1-yl)-4-(2,2,2-trifluoroethoxy)pyridin-2-yl]-4,4-diethyl-5H-1,3-oxazole;
2-[5-cyclopropyl-4-(2,2,2-trifluoroethoxy)pyridin-2-yl]-3-oxa-1-azaspiro[4.5]dec-1-ene;
5-tert-butyl-3-[4-(cyclopropylmethoxy)-5-(3,3-difluoroazetidin-1-yl)pyridin-2-yl]-1,2,4-oxadiazole;
5-tert-butyl-3-[5-cyclopropyl-4-(2,2,2-trifluoroethoxy)pyridin-2-yl]-1,2,4-oxadiazole;
3-[5-cyclopropyl-4-(2,2,2-trifluoroethoxy)pyridin-2-yl]-5-(1-methylcyclopropyl)-1,2,4-oxadiazole;
1-[6-(5-tert-butyl-1,2,4-oxadiazol-3-yl)-4-(cyclopropylmethoxy)pyridin-3-yl]-6-oxa-1-azaspiro[3.3]heptane;
3-[5-cyclopropyl-4-(2,2,2-trifluoroethoxy)pyridin-2-yl]-5-propan-2-yl-1,2,4-oxadiazole;
1-[3-[5-cyclopropyl-4-(2,2,2-trifluoroethoxy)pyridin-2-yl]-1,2,4-oxadiazol-5-yl]cyclopropan-1-ol;
3-[5-cyclopropyl-4-(2,2,2-trifluoroethoxy)pyridin-2-yl]-5-(3-methyloxetan-3-yl)-1,2,4-oxadiazole;
3-[5-cyclopropyl-4-(2,2,2-trifluoroethoxy)pyridin-2-yl]-1,2,4-oxadiazole;
3-tert-butyl-5-[5-cyclopropyl-4-(2,2,2-trifluoroethoxy)pyridin-2-yl]-1,2,4-oxadiazole;
2-[5-cyclopropyl-4-(2,2,2-trifluoroethoxy)pyridin-2-yl]-5,5-dimethyl-4H-1,3-oxazole;
5-[5-cyclopropyl-4-(2,2,2-trifluoroethoxy)pyridin-2-yl]-3-propan-2-yl-1,2,4-oxadiazole;
5-tert-butyl-3-[4-(cyclopropylmethoxy)-5-methylsulfonylpyridin-2-yl]-1,2,4-oxadiazole;
5-tert-butyl-3-[5-(3,3-difluoroazetidin-1-yl)-4-(2,2,2-trifluoroethoxy)pyridin-2-yl]-1,2,4-oxadiazole;
3-[5-(3,3-difluoroazetidin-1-yl)-4-(2,2,2-trifluoroethoxy)pyridin-2-yl]-5-propan-2-yl-1,2,4-oxadiazole;
1-[3-[5-(3,3-difluoroazetidin-1-yl)-4-(2,2,2-trifluoroethoxy)pyridin-2-yl]-1,2,4-oxadiazol-5-yl]cyclopropan-1-ol;
3-[5-(3,3-difluoroazetidin-1-yl)-4-(2,2,2-trifluoroethoxy)pyridin-2-yl]-5-(3-methyloxetan-3-yl)-1,2,4-oxadiazole;
5-tert-butyl-3-[5-cyclopropyl-4-[(2S)-1,1,1-trifluoropropan-2-yl]oxypyridin-2-yl]-1,2,4-oxadiazole;
5-tert-butyl-3-[5-cyclopropyl-4-[(2R)-1,1,1-trifluoropropan-2-yl]oxypyridin-2-yl]-1,2,4-oxadiazole;
3-tert-butyl-5-[5-cyclopropyl-4-[(2R)-1,1,1-trifluoropropan-2-yl]oxypyridin-2-yl]-1,2,4-oxadiazole;
3-tert-butyl-5-[5-cyclopropyl-4-[(2S)-1,1,1-trifluoropropan-2-yl]oxypyridin-2-yl]-1,2,4-oxadiazole;
5-tert-butyl-3-[5-cyclopropyl-4-[(4-fluorophenyl)methoxy]pyridin-2-yl]-1,2,4-oxadiazole;
5-tert-butyl-3-[5-cyclopropyl-4-(oxetan-3-yloxy)pyridin-2-yl]-1,2,4-oxadiazole;
5-tert-butyl-3-[5-cyclopropyl-4-[(3-methyloxetan-3-yl)methoxy]pyridin-2-yl]-1,2,4-oxadiazole;
5-tert-butyl-3-[5-cyclopropyl-4-(oxolan-2-ylmethoxy)pyridin-2-yl]-1,2,4-oxadiazole;
5-tert-butyl-3-[5-cyclopropyl-4-[[(2S)-1-methylpyrrolidin-2-yl]methoxy]pyridin-2-yl]-1,2,4-oxadiazole;
5-tert-butyl-3-[5-cyclopropyl-4-(oxetan-2-ylmethoxy)pyridin-2-yl]-1,2,4-oxadiazole;
5-tert-butyl-3-[5-cyclopropyl-4-(1-methylpyrrolidin-3-yl)oxypyridin-2-yl]-1,2,4-oxadiazole
3-[3-[5-cyclopropyl-4-(cyclopropylmethoxy)pyridin-2-yl]-1,2,4-oxadiazol-5-yl]oxetan-3-amine;
5-tert-butyl-3-[5-cyclopropyl-4-(4-fluorophenoxy)pyridin-2-yl]-1,2,4-oxadiazole;
5-tert-butyl-3-[5-cyclopropyl-4-(oxolan-3-yloxy)pyridin-2-yl]-1,2,4-oxadiazole;
5-tert-butyl-3-[5-cyclopropyl-4-(oxan-4-yloxy)pyridin-2-yl]-1,2,4-oxadiazole;
2-(5-tert-butyl-1H-imidazol-2-yl)-5-(3,3-difluoroazetidin-1-yl)-4-(2,2,2-trifluoroethoxy)pyridine;
5-tert-butyl-2-[5-cyclopropyl-4-(cyclopropylmethoxy)pyridin-2-yl]-1,3-oxazole;

2-[5-cyclopropyl-4-(2,2,2-trifluoroethoxy)pyridin-2-yl]-4-methyl-4-propan-2-yl-1H-imidazol-5-one;
5-tert-butyl-3-[5-methylsulfonyl-4-(2,2,2-trifluoroethoxy)pyridin-2-yl]-1,2,4-oxadiazole;
2-[5-cyclopropyl-4-(2,2,2-trifluoroethoxy)pyridin-2-yl]-4-ethyl-4-methyl-1H-imidazol-5-one;
2-[5-cyclopropyl-4-(2,2,2-trifluoroethoxy)pyridin-2-yl]-4-methyl-4-(2-methylpropyl)-1H-imidazol-5-one;
2-[5-bromo-4-(2,2,2-trifluoroethoxy)pyridin-2-yl]-4-methyl-4-propan-2-yl-1H-imidazol-5-one;
5-tert-butyl-3-[5-chloro-4-(2,2,2-trifluoroethoxy)pyridin-2-yl]-1,2,4-oxadiazole;
3-[5-chloro-4-(2,2,2-trifluoroethoxy)pyridin-2-yl]-5-cyclopropyl-1,2,4-oxadiazole;
5-cyclopropyl-3-[5-cyclopropyl-4-(2,2,2-trifluoroethoxy)pyridin-2-yl]-1,2,4-oxadiazole;
1-[2-(5-tert-butyl-1,2,4-oxadiazol-3-yl)-5-cyclopropylpyridin-4-yl]pyrrolidin-3-ol;
5-tert-butyl-3-[5-cyclopropyl-4-(3,3,4,4-tetrafluoropyrrolidin-1-yl)pyridin-2-yl]-1,2,4-oxadiazole;
5-tert-butyl-3-[5-cyclopropyl-4-(4-methylsulfonylphenoxy)pyridin-2-yl]-1,2,4-oxadiazole;
7-[2-(5-tert-butyl-1,2,4-oxadiazol-3-yl)-5-cyclopropylpyridin-4-yl]-2-oxa-7-azaspiro[3.4]octane;
5-tert-butyl-3-[5-cyclopropyl-4-(3,3-difluoropyrrolidin-1-yl)pyridin-2-yl]-1,2,4-oxadiazole;
4-[2-(5-tert-butyl-1,2,4-oxadiazol-3-yl)-5-cyclopropylpyridin-4-yl]morpholine;
5-tert-butyl-3-(5-cyclopropyl-4-pyrrolidin-1-ylpyridin-2-yl)-1,2,4-oxadiazole;
5-tert-butyl-3-(5-cyclopropyl-4-cyclopropylsulfonylpyridin-2-yl)-1,2,4-oxadiazole;
5-tert-butyl-3-[5-cyclopropyl-4-(3-methoxyazetidin-1-yl)pyridin-2-yl]-1,2,4-oxadiazole;
6-[2-(5-tert-butyl-1,2,4-oxadiazol-3-yl)-5-cyclopropylpyridin-4-yl]-2-oxa-6-azaspiro[3.3]heptane;
5-tert-butyl-3-[5-cyclopropyl-4-(2-ethoxyethoxy)pyridin-2-yl]-1,2,4-oxadiazole;
5-tert-butyl-3-[5-cyclopropyl-4-(1-methoxybutan-2-yloxy)pyridin-2-yl]-1,2,4-oxadiazole;
5-tert-butyl-3-[5-cyclopropyl-4-[2-[(2-methylpropan-2-yl)oxy]ethoxy]pyridin-2-yl]-1,2,4-oxadiazole;
5-tert-butyl-3-[5-cyclopropyl-4-[1-[(2-methylpropan-2-yl)oxy]propan-2-yloxy]pyridin-2-yl]-1,2,4-oxadiazole;
5-tert-butyl-3-[5-cyclopropyl-4-(1-methoxypropan-2-yloxy)pyridin-2-yl]-1,2,4-oxadiazole;
5-tert-butyl-3-[5-cyclopropyl-4-(oxan-3-yloxy)pyridin-2-yl]-1,2,4-oxadiazole;
5-tert-butyl-3-[5-cyclopropyl-4-(3-methoxybutoxy)pyridin-2-yl]-1,2,4-oxadiazole;
5-tert-butyl-3-[5-cyclopropyl-4-(oxetan-3-ylmethoxy)pyridin-2-yl]-1,2,4-oxadiazole;
5-cyclopropyl-3-[5-cyclopropyl-4-[(2S)-1,1,1-trifluoropropan-2-yl]oxypyridin-2-yl]-1,2,4-oxadiazole;
5-tert-butyl-3-[5-cyclopropyl-4-(1-ethylpyrrolidin-3-yl)oxypyridin-2-yl]-1,2,4-oxadiazole;
5-tert-butyl-3-[5-cyclopropyl-4-(1-propan-2-ylpyrrolidin-3-yl)oxypyridin-2-yl]-1,2,4-oxadiazole;
5-tert-butyl-3-[5-cyclopropyl-4-(2-pyrrolidin-1-ylethoxy)pyridin-2-yl]-1,2,4-oxadiazole;
5-tert-butyl-3-[5-cyclopropyl-4-(2-piperidin-1-ylethoxy)pyridin-2-yl]-1,2,4-oxadiazole;
5-tert-butyl-3-[5-cyclopropyl-4-(1-piperidin-1-ylpropan-2-yloxy)pyridin-2-yl]-1,2,4-oxadiazole;
5-tert-butyl-3-[5-cyclopropyl-4-[(1-methylpiperidin-2-yl)methoxy]pyridin-2-yl]-1,2,4-oxadiazole;
2-tert-butyl-5-[5-cyclopropyl-4-(oxan-4-yloxy)pyridin-2-yl]-1,3,4-oxadiazole;
5-tert-butyl-3-[5-cyclopropyl-4-(1-methylpiperidin-3-yl)oxypyridin-2-yl]-1,2,4-oxadiazole;
5-tert-butyl-3-[5-cyclopropyl-4-(1-ethylpiperidin-3-yl)oxypyridin-2-yl]-1,2,4-oxadiazole;
2-[2-(5-tert-butyl-1,2,4-oxadiazol-3-yl)-5-cyclopropylpyridin-4-yl]oxy-N,N-diethylpropan-1-amine;
3-[[2-(5-tert-butyl-1,2,4-oxadiazol-3-yl)-5-cyclopropylpyridin-4-yl]oxymethyl]morpholine;
4-[2-[2-(5-tert-butyl-1,2,4-oxadiazol-3-yl)-5-cyclopropylpyridin-4-yl]oxyethyl]morpholine;
5-tert-butyl-3-(5-cyclopropyl-4-piperidin-3-yloxypyridin-2-yl)-1,2,4-oxadiazole;
5-tert-butyl-3-[5-cyclopropyl-4-[(3-fluorooxetan-3-yl)methoxy]pyridin-2-yl]-1,2,4-oxadiazole;
5-tert-butyl-3-[5-cyclopropyl-4-[(2,5-dimethyl-1,3-oxazol-4-yl)methoxy]pyridin-2-yl]-1,2,4-oxadiazole;
5-tert-butyl-3-[5-cyclopropyl-4-[(5-methyl-1,2-oxazol-3-yl)methoxy]pyridin-2-yl]-1,2,4-oxadiazole;
5-tert-butyl-3-[5-cyclopropyl-4-(3-methylsulfonylphenoxy)pyridin-2-yl]-1,2,4-oxadiazole;
5-tert-butyl-3-[5-(3-fluorooxetan-3-yl)-4-(oxan-4-yloxy)pyridin-2-yl]-1,2,4-oxadiazole;
5-tert-butyl-3-[5-(3-fluorooxetan-3-yl)-4-(4-fluorophenoxy)pyridin-2-yl]-1,2,4-oxadiazole;
3-[2-[5-cyclopropyl-4-(2,2,2-trifluoroethoxy)pyridin-2-yl]-4-methyl-5H-1,3-oxazol-4-yl]-5-methyl-1,2,4-oxadiazole;
5-tert-butyl-3-(6-chloro-5-cyclopropyl-4-(4-fluorobenzyloxy)pyridin-2-yl)-1,2,4-oxadiazole;
2-tert-butyl-5-[5-cyclopropyl-4-(2,2,2-trifluoroethoxy)pyridin-2-yl]-1,3,4-oxadiazole;
5-tert-butyl-3-[6-chloro-5-cyclopropyl-4-(oxan-4-yloxy)pyridin-2-yl]-1,2,4-oxadiazole;
5-tert-butyl-3-[5-cyclopropyl-4-(2,2-difluoroethoxy)pyridin-2-yl]-1,2,4-oxadiazole;
5-tert-butyl-3-[5-cyclopropyl-4-(2-fluoroethoxy)pyridin-2-yl]-1,2,4-oxadiazole; and
5-tert-butyl-3-[5-cyclopropyl-4-(pyridin-2-ylmethoxy)pyridin-2-yl]-1,2,4-oxadiazole.

The invention relates in particular to a compound of formula (I) selected from:
5-tert-butyl-3-[5-cyclopropyl-4-(2,2,2-trifluoroethoxy)pyridin-2-yl]-1,2,4-oxadiazole;
3-tert-butyl-5-[5-cyclopropyl-4-(2,2,2-trifluoroethoxy)pyridin-2-yl]-1,2,4-oxadiazole;
5-tert-butyl-3-[5-cyclopropyl-4-[(3-methyloxetan-3-yl)methoxy]pyridin-2-yl]-1,2,4-oxadiazole;
5-tert-butyl-3-[5-cyclopropyl-4-(oxolan-2-ylmethoxy)pyridin-2-yl]-1,2,4-oxadiazole;
5-tert-butyl-3-[5-cyclopropyl-4-(4-fluorophenoxy)pyridin-2-yl]-1,2,4-oxadiazole;
5-tert-butyl-3-[5-cyclopropyl-4-(oxolan-3-yloxy)pyridin-2-yl]-1,2,4-oxadiazole;
5-tert-butyl-3-[5-cyclopropyl-4-(oxan-4-yloxy)pyridin-2-yl]-1,2,4-oxadiazole;
5-tert-butyl-3-[5-cyclopropyl-4-(2-ethoxyethoxy)pyridin-2-yl]-1,2,4-oxadiazole;
5-tert-butyl-3-[5-cyclopropyl-4-(3-methoxybutoxy)pyridin-2-yl]-1,2,4-oxadiazole; and
5-tert-butyl-3-[5-cyclopropyl-4-(oxetan-3-ylmethoxy)pyridin-2-yl]-1,2,4-oxadiazole.

The invention further relates in particular to a compound of formula (I) selected from
5-tert-butyl-3-[5-cyclopropyl-4-[(5-fluoropyridin-2-yl)methoxy]pyridin-2-yl]-1,2,4-oxadiazole;

5-tert-butyl-3-[5-cyclopropyl-4-(pyridin-3-ylmethoxy)pyridin-2-yl]-1,2,4-oxadiazole;
2-tert-butyl-5-[5-cyclopropyl-4-[(2S)-1,1,1-trifluoropropan-2-yl]oxypyridin-2-yl]-1,3,4-oxadiazole;
3-tert-butyl-5-(5-cyclopropyl-4-(tetrahydro-2H-pyran-4-yloxy)pyridin-2-yl)-1,2,4-oxadiazole;
3-tert-butyl-5-[5-cyclopropyl-4-[[(2S)-1-methylpyrrolidin-2-yl]methoxy]pyridin-2-yl]-1,2,4-oxadiazole; and
3-tert-butyl-5-(5-cyclopropyl-4-(2,2-difluoroethoxy)pyridin-2-yl)-1,2,4-oxadiazole.

The invention further relates in particular to a compound of formula (I) selected from
5-tert-butyl-3-[5-cyclopropyl-4-[(5-fluoropyridin-2-yl)methoxy]pyridin-2-yl]-1,2,4-oxadiazole;
3-tert-butyl-5-(5-cyclopropyl-4-(tetrahydro-2H-pyran-4-yloxy)pyridin-2-yl)-1,2,4-oxadiazole; and
3-tert-butyl-5-(5-cyclopropyl-4-(2,2-difluoroethoxy)pyridin-2-yl)-1,2,4-oxadiazole.

The synthesis of the compound of formula (I) can, for example, be accomplished according to the following schemes.

Unless otherwise specified, $R^2$ to $R^8$ and A have in the following schemes the meaning as defined above. In schemes 1 to 15, $R^1$ is hydrogen; in scheme 16, $R^1$ is halogen.

Following the procedure according to scheme 1, compound AA can be used as starting material. AA is either commercially available, described in the literature or can be synthesized by a person skilled in the art.

Compound AB can be prepared from AA by reaction with a suitably substituted alcohol as described in the claims, in the presence of a base, for example sodium hydride, with or without an inert solvent, for example dimethylformamide, at temperatures ranging from room temperature to the reflux temperature of the solvent (step a).

Conversion of compound AB to compound AC can be prepared by coupling a suitably substituted cycloalkyl metal species (e.g. a trifluoroborate $[BF_3]^-K^+$, a boronic acid $B(OH)_2$ or a boronic acid pinacol ester) (step b), e.g. an organotrifluoroborate potassium salt in the presence of a palladium catalyst such as palladium(II)acetate/butyl-1-adamantylphosphine and a base such as cesium carbonate in an inert solvent such as toluene at temperatures between 50° C. and the boiling temperature of the solvent, or an arylboronic acid or arylboronic acid ester in the presence of a suitable catalyst, in particular a palladium catalyst and more particularly palladium(II)acetate/triphenylphosphine mixtures or palladium(II)chloride-dppf (1,1'-bis(diphenylphosphino)ferrocene) complexes and a base such as triethylamine, sodium carbonate or potassium phosphate in an inert solvent such as dimethylformamide, toluene, tetrahydrofuran, acetonitrile or dimethoxyethane.

Scheme 1

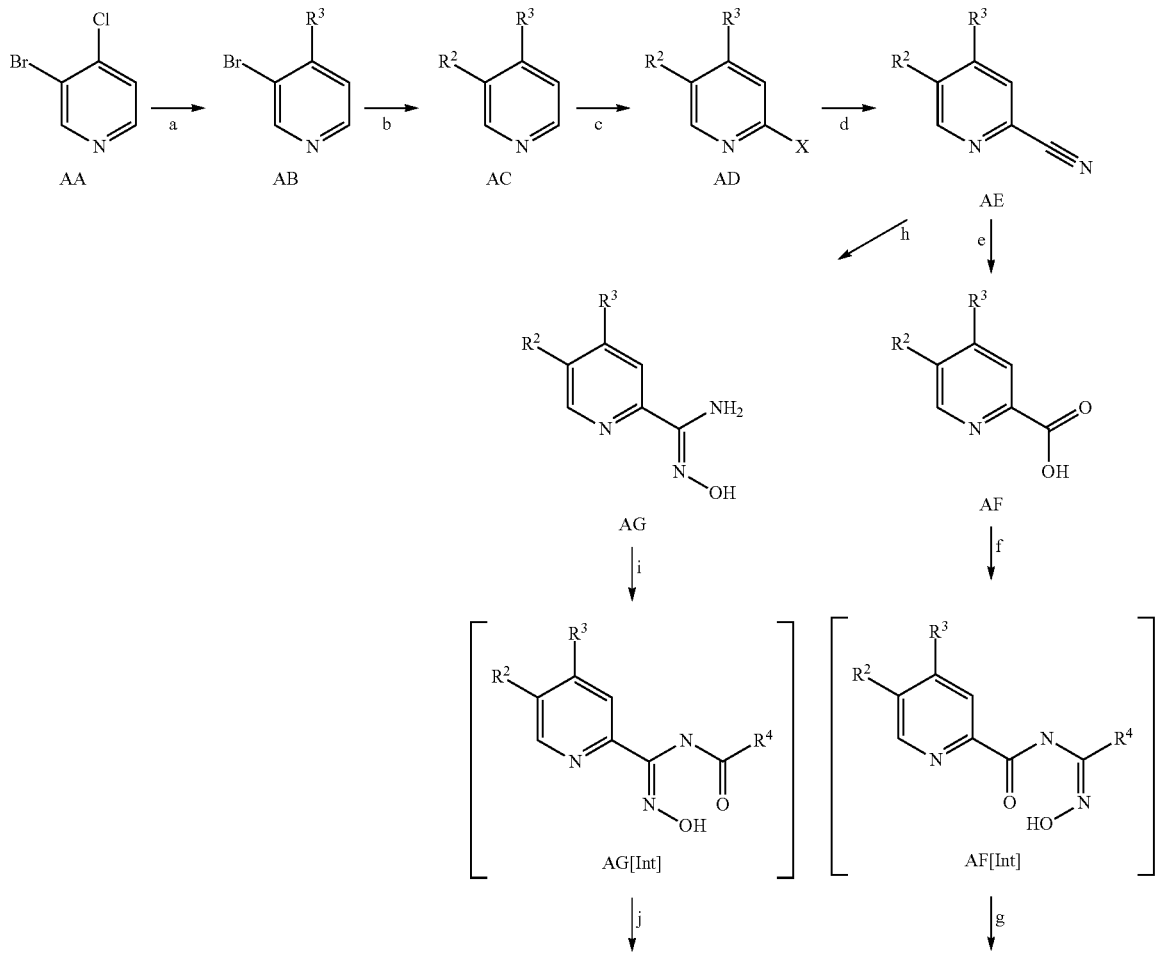

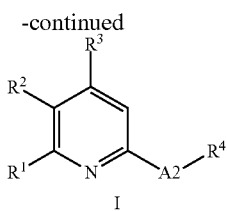
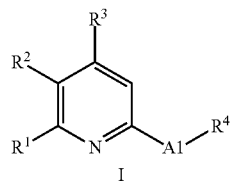

AC can be selectively halogenated on position 2 to give AD for example by treatment of N,N-dimethylethanolamine with butyl lithium on AC followed by addition of a source of Bromine, e.g. 1,2-dibromotetrachloroethane (step c).

Compound AE can be prepared from AD by addition of cyanide source, e.g. zinc cyanide or copper cyanide in presence of a palladium catalyst such as palladium triphenylphosphine tetrakis or tris(dibenzylideneacetone)dipalladium(0) and dppf, in a solvent such as DMF or dioxane and refluxed to the solvent boiling point temperature (step d).

Hydrolisis of compound AE lead to the picolinic acid AF and can be performed under acidic or basic conditions known to a person skilled in the art, e.g. with aqueous solution of hydrochloric acid at 100° C. (step e).

Compounds of formula I with A1, can be prepared from compounds of formula AF by amide coupling methods known to a person skilled in the art, with the suitably substituted hydroxyamidine commercially available leading to intermediate AF[Int](step f), followed by heating to cyclise to the oxadiazole ring in a high boiling point solvent such as DMF (step g).

Compound AE can be converted to AG by treatment with hydroxylamine hydrochloride in presence of base such as triethylamine (step h).

Cylisation to compound I with A2 can be performed by amide coupling methods known to a person skilled in the art, with the suitably substituted commercially available carboxylic acid to give intermediate AG[Int](step i), followed by heating to cyclise to the oxadiazole ring in a high boiling point solvent such as DMF (step j).

Alternatively, following the procedure according to scheme 2, compound BA can be prepared from AC by oxidation with a suitable oxidizing reagent under conditions known to a person skilled in the art, e.g. by treatment with 3-chloro perbenzoic acid in dichloromethane at ambient temperature (step a).

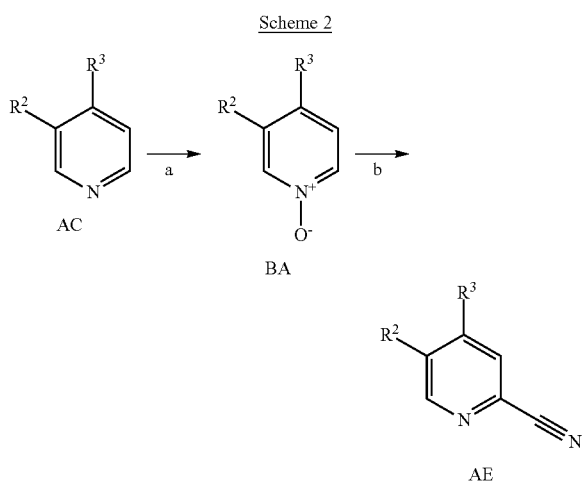

Compound AE can be then prepared from BA by a cyanation method known to a person skilled in the art, such treatment with trimethylsilanecarbonitrile followed by addition of dimethylcarbamic chloride in a solvent such as DCM.

Compound AE can be further elaborated to compounds I with A1 or A2, as described in scheme 1, step e and for g and h.

Alternatively, according to scheme 3, especially when $R^2$ was a substituent sensitive to oxidation such as groups with nitrogen, compound CA can be prepared from AB by oxidation with a suitable oxidizing reagent under conditions known to a person skilled in the art (step a), e.g. by treatment with 3-chloro perbenzoic acid in dichloromethane at ambient temperature.

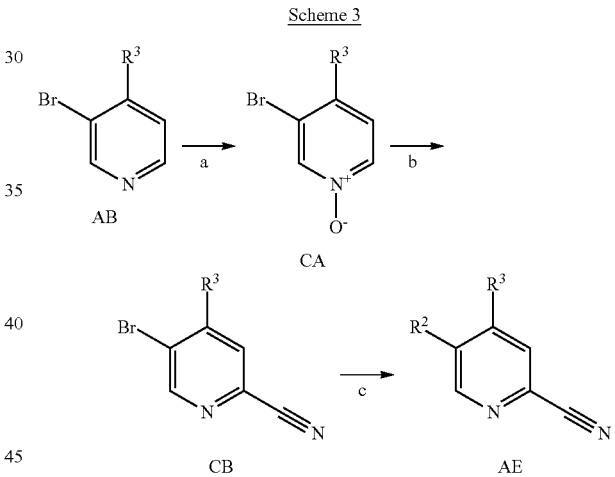

Compound CB can be then prepared from CA by a cyanation method known to a person skilled in the art, such treatment with trimethylsilanecarbonitrile followed by addition of dimethylcarbamic chloride in a solvent such as DCM (step b).

Compound AE can be obtained from compound CB by substituting with an amine or salt of an amine such difluoroazetidine hydrochloride, using Buchwald reaction conditions known to a person skilled in the art (step c), such as $Cs_2CO_3$, palladium acetate and BINAP in a solvent such as toluene under reflux.

Compound AE can be further elaborated to compounds I with A1 or A2, as described in scheme 1, step e and for g and h.

Alternatively, following the procedure according to scheme 4, compound DA can be prepared from CB by treatment with hydroxylamine hydrochloride in presence of base such as triethylamine in a solvent such as DCM (step a).

Scheme 4

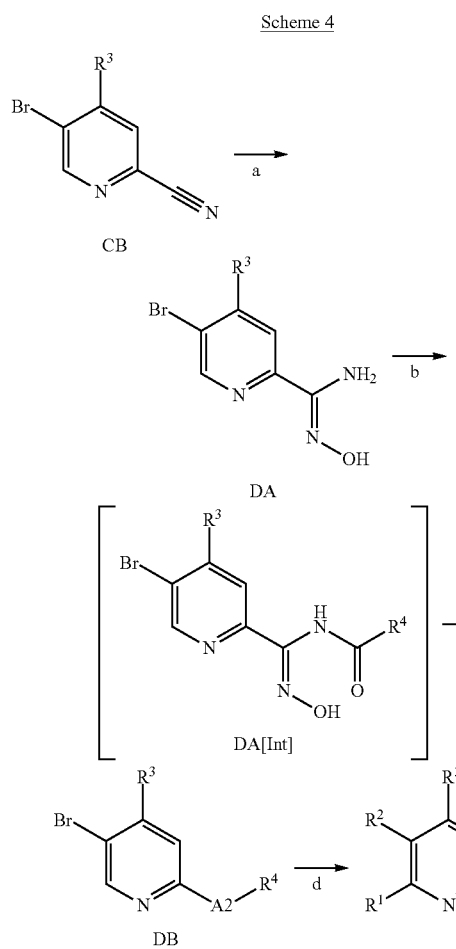

Cyclisation of compound DA to compound DB with heterocycle type A2 can be performed by amide coupling methods known to a person skilled in the art, with the suitably substituted commercially available carboxylic acid to give intermediate DA[Int](step b), followed by heating to cyclise to the oxadiazole ring in a high boiling point solvent such as DMF (step c).

Compound I can be obtained from compound DB by substituting with an amine or salt of an amine such difluoroazetidine hydrochloride, using Buchwald reaction conditions known to a person skilled in the art (step d), such as $Cs_2CO_3$, palladium acetate and BINAP in a solvent such as toluene under reflux.

Compound AE can be further elaborated to compounds I with heterocycle type A2 by coupling $R^2$ where $R^2$ is either an alkyl chain using similar method as described in scheme 1 step b; or $R^2$ is an amine or the corresponding salt using Buchwald reaction conditions as described in scheme 3 step c.

Following the procedure according to scheme 5, compound EA can be used as starting material. EA is either commercially available, described in the literature or can be synthesized by a person skilled in the art.

Compound EB can be obtained from compound EA (step a) by coupling with an alkyl chain using similar method as described in scheme 1 step b.

Compound EC can be prepared from EB by cyanation reaction methods, e.g. zinc cyanide or copper cyanide in presence of a palladium catalyst such as palladium triphenylphosphine tetrakis or tris(dibenzylideneacetone)dipalladium(0) and dppf, in a solvent such as DMF or dioxane and refluxed to the solvent boiling point temperature (step b).

Compound EC can be converted to ED by treatment with hydroxylamine hydrochloride in presence of base such as triethylamine in a solvent such as DCM (step c).

Cyclisation of compound ED to compound EE with heterocycle type A2 can be performed by amide coupling methods known to a person skilled in the art, with the suitably substituted commercially available carboxylic acid to give intermediate ED[Int](step d), followed by heating to cyclise to the oxadiazole ring in a high boiling point solvent such as DMF (step e).

Scheme 5

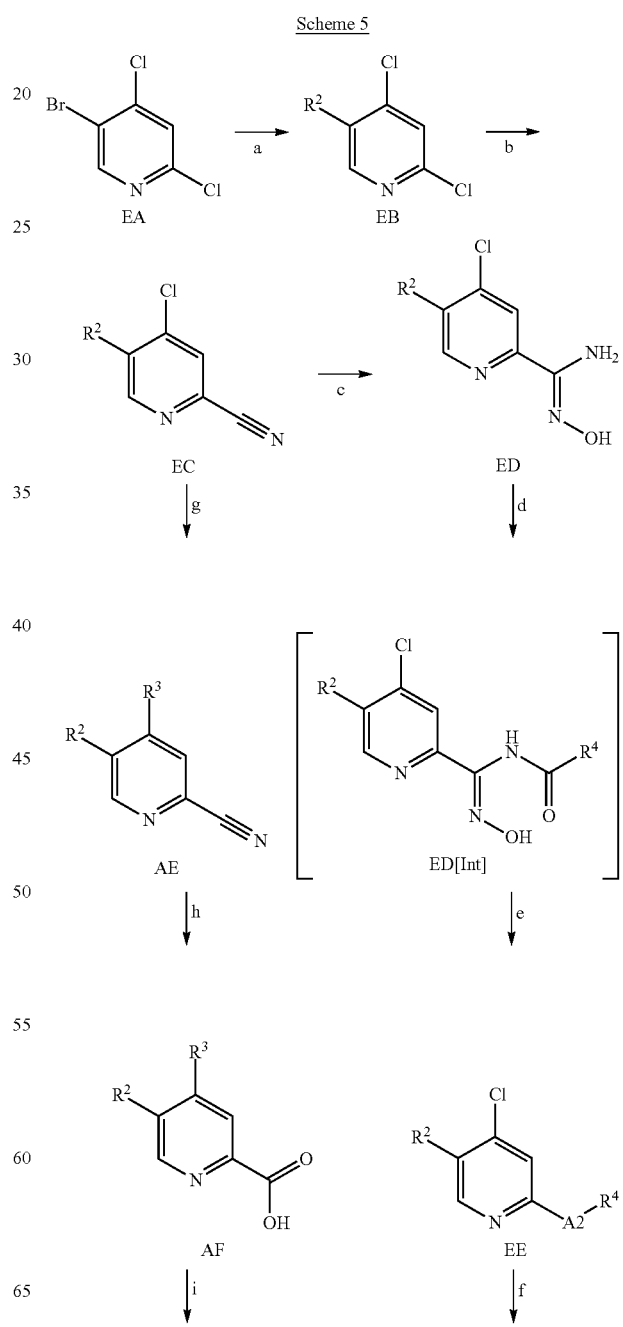

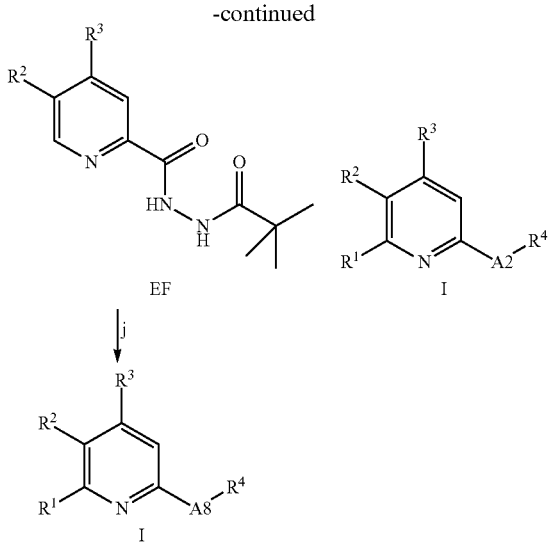

Compound I can be obtained from compound EE (step f) by reaction with a suitably substituted alcohol as described in the claims, in the presence of a base, for example sodium hydride, with or without an inert solvent, for example dimethylformamide, at temperatures ranging from room temperature to the reflux temperature of the solvent; or by reaction with a suitably substituted amine using a base such as $Cs_2CO_3$ in a high boiling point solvent such as ethylene glycol or alternatively using Buchwald reaction conditions known to a person skilled in the art, such $Cs_2CO_3$, palladium acetate and BINAP in a solvent such toluene under reflux.

Compound AE can be prepared from compound EC (step g) by reaction with a suitably substituted alcohol as described in the claims, in the presence of a base, for example sodium hydride, with or without an inert solvent, for example dimethylformamide, at temperatures ranging from room temperature to the reflux temperature of the solvent.

Hydrolisis of compound AE lead to the picolinic acid AF and can be performed under acidic or basic conditions known to a person skilled in the art, e.g. with aqueous solution of hydrochloric acid at 100° C. (step h).

Compounds of formula EF can be prepared from compounds of formula AF by amide coupling methods known to a person skilled in the art, with the suitably substituted hydrazide commercially available, in an appropriate solvent (step i).

Cyclisation of compound EF to compound I with heterocycle type A8 can be performed by dehydration methods (step j) known to a person skilled in the art, e.g. treatment of compound EF by a reaction mixture of trifluoromethanesulfonic anhydride and triphenylphosphine oxide in a solvent such as DCM.

Following the procedure according to scheme 6 (step a), compound FA can be obtained from compound AA by coupling $R^2$ where $R^2$ is an alkyl chain using similar method as described in scheme 1 step b.

Compound FA can be selectively carbonylated on position 2 to give FB by a method known to a person skilled in the art for example by treatment of N,N-dimethylethanolamine with butyl lithium on AC followed by addition of a source of carbon dioxide, e.g. dry ice (step b).

Compound FC (with A1), can be prepared from compound FB by amide coupling methods known to a person skilled in the art, with the suitably substituted hydroxyamidine commercially available giving intermediate FB[Int] (step c), followed by heating to cyclise to the oxadiazole ring in a high boiling point solvent such as DMF (step d).

Scheme 6

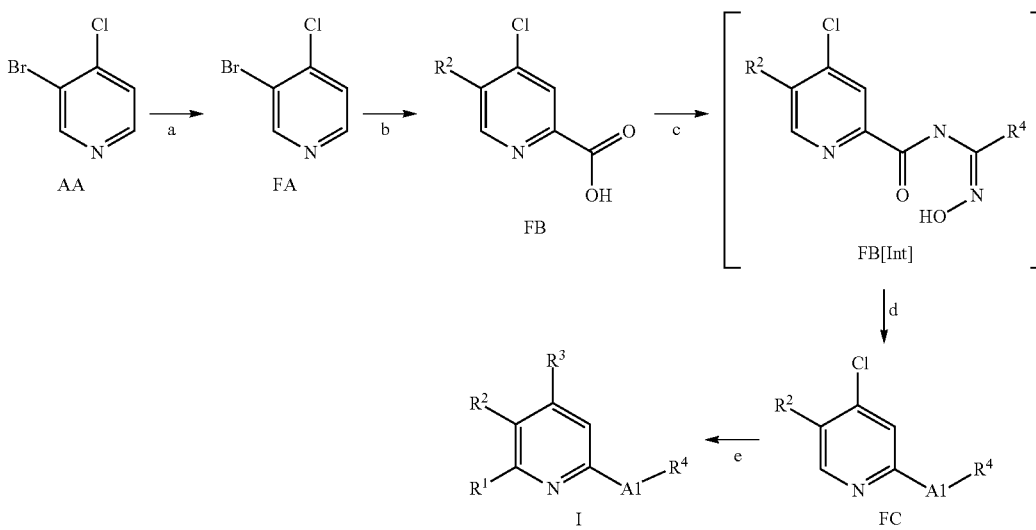

Compound I (with A1) can be prepared from compound FC by reaction with a suitably substituted alcohol as described in the claims, in the presence of a base, for example sodium hydride, with or without an inert solvent, for example dimethylformamide, at temperatures ranging from room temperature to the reflux temperature of the solvent (step e).

Following the procedure according to scheme 7 (step a), compound GA can be obtained from compound EA by coupling with oxetane-3-one using Grignard reaction method known to a person skilled in the art, e.g. isopropyl magnesium chloride lithium chloride complex in a solvent such as THF.

Compound GB can be prepared from GA by cyanation reaction methods, e.g. zinc cyanide or copper cyanide in presence of a palladium catalyst such as palladium triphenylphosphine tetrakis or tris(dibenzylideneacetone)dipalladium(0) and dppf, in a solvent such as DMF or dioxane and refluxed to the solvent boiling point temperature (step b).

described in the claims, in the presence of a base, for example sodium hydride, with or without an inert solvent, for example dimethylformamide, at temperatures ranging from room temperature to the reflux temperature of the solvent.

Scheme 7

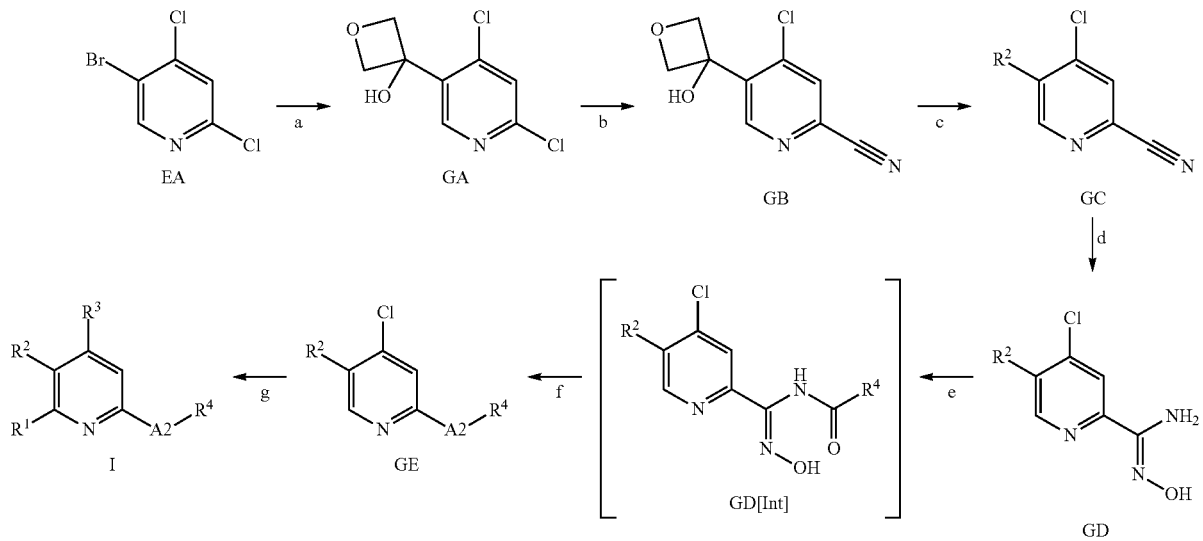

Compound GC can be prepared from GB by conversion of the hydroxy to fluorine using fluorinating reagents, such as DAST (step c).

Compound GC can be converted to GD by treatment with hydroxylamine hydrochloride in presence of base such as triethylamine in a solvent such DCM (step d).

Cyclisation of compound GD to compound GE with heterocycle type A2 can be performed by amide coupling methods known to a person skilled in the art, with the suitably substituted commercially available carboxylic acid giving intermediate GD[Int] (step e), followed by heating to cyclise to the oxadiazole ring in a high boiling point solvent such as DMF (step f).

Compound I (with A2) can b obtained from compound GE (step g) by reaction with a suitably substituted alcohol as Following the procedure according to scheme 8, compound HA can be used as starting material. HA is either commercially available, described in the literature or can be synthesized by a person skilled in the art.

Compound HB can be prepared from HA by reaction with a suitably substituted alkyl chain with a leaving group, e.g. halogen or triflate, in the presence of a base, for example sodium hydride, in a solvent, for example dimethylformamide, at temperatures ranging from room temperature to the reflux temperature of the solvent (step a).

Scheme 8

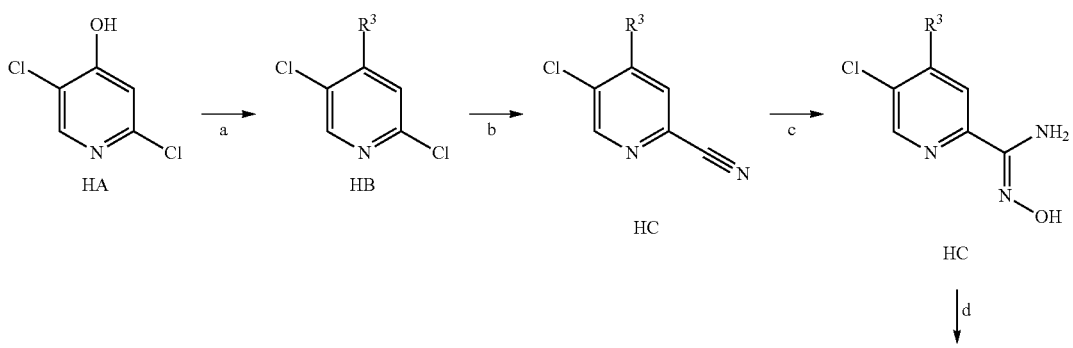

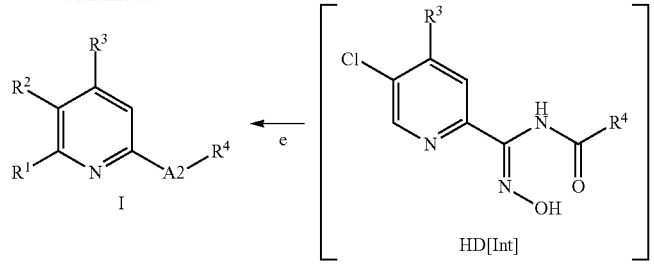

Compound HC can be prepared from HB by cyanation reaction methods known to a person skilled in the art, e.g. zinc cyanide or copper cyanide in presence of a palladium catalyst such as palladium triphenylphosphine tetrakis or tris(dibenzylideneacetone)dipalladium(0) and dppf, in a solvent such as DMF or dioxane and refluxed to the solvent boiling point temperature (step b).

Compound HC can be converted to HD by treatment with hydroxylamine hydrochloride in presence of base such as triethylamine in a solvent such DCM (step c).

Cyclisation of compound HD to compound I, with heterocycle type A2 and $R^2$=chlorine, can be performed by amide coupling methods known to a person skilled in the art, with the suitably substituted commercially available carboxylic acid to give intermediate HD[Int] (step d), followed by heating to cyclise to the oxadiazole ring in a high boiling point solvent such as DMF (step e).

Following the procedure according to scheme 9, compound JA can be obtained from compound AF by amide coupling methods known to a person skilled in the art, with the suitably substituted amine commercially available, in an appropriate solvent such as DCM (step a).

Scheme 9

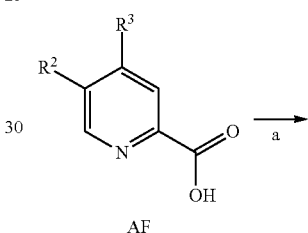

Cyclisation of compound JA to compound I with heterocycle type A3 can be performed by dehydration methods (step b) known to a person skilled in the art, e.g. using a mild dehydrating reagent such as Burgess Reagent in a solvent such as THF.

Following the procedure according to scheme 10 (step a), compound KA can be obtained from compound AF by amide coupling methods known to a person skilled in the art, with the suitably substituted amine commercially available, in an appropriate solvent such as DCM (step a).

Scheme 10

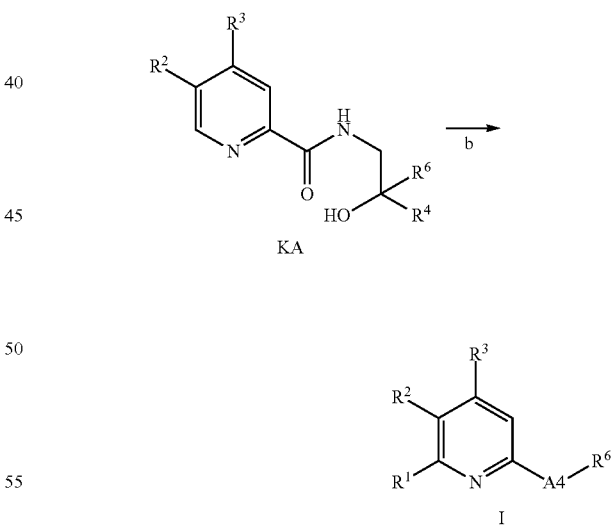

Formation of compound KA to compound I with heterocycle type A4 can be performed by condensation methods known to a person skilled in the art, such use of methanesulfonic acid, in a solvent such as DCM (step b).

Following the procedure according to scheme 11 (step a), compound LA can be obtained from compound AE by amidine formation methods known to a person skilled in the art, e.g. treatment by a reaction mixture of trimethylaluminum on ammonium chloride in a solvent such as toluene.

Scheme 11

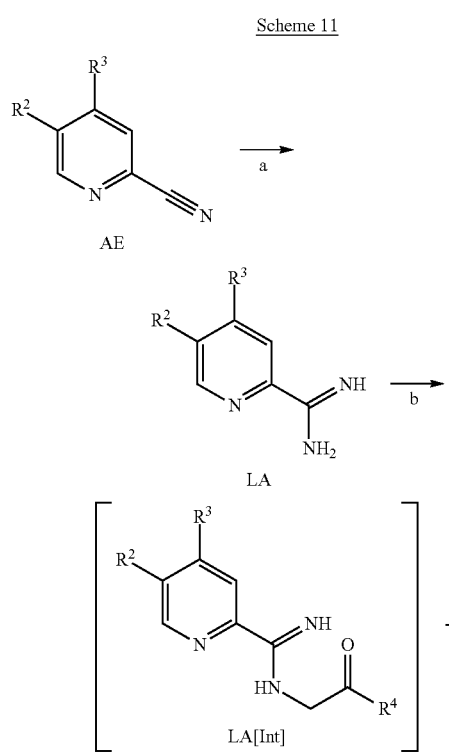

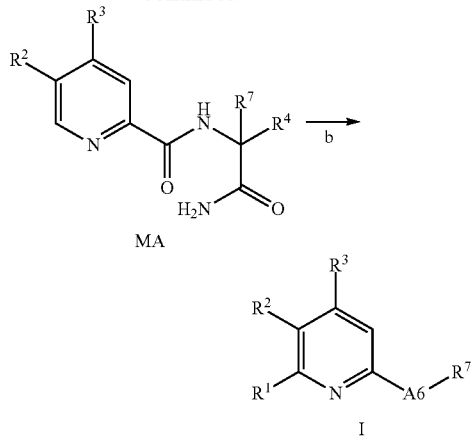

Conversion of compound MA to compound I with heterocycle type A6 (step b) can be performed by cyclising using a base, e.g. potassium hydroxide in a solvent such as THF at reflux temperature of the solvent.

Following the procedure according to scheme 13 (step a), compound NA can be obtained from compound AF by amide coupling methods known to a person skilled in the art, with the suitably substituted alpha amino alcohol, in an appropriate solvent such as DCM (step a).

Conversion of compound LA to compound I with heterocycle type A5 can be performed by coupling method with an alpha halogeno ketone suitably substituted known to a person skilled in the art, e.g use of a base such as DBU in a solvent such as ethanol giving intermediate LA[Int] (step b), and heated to cyclise (step c).

Following the procedure according to scheme 12, compound MA can be obtained from compound AF (step a) by amide coupling methods known to a person skilled in the art, with the suitably substituted amine, in an appropriate solvent such as THF (step a).

Scheme 13

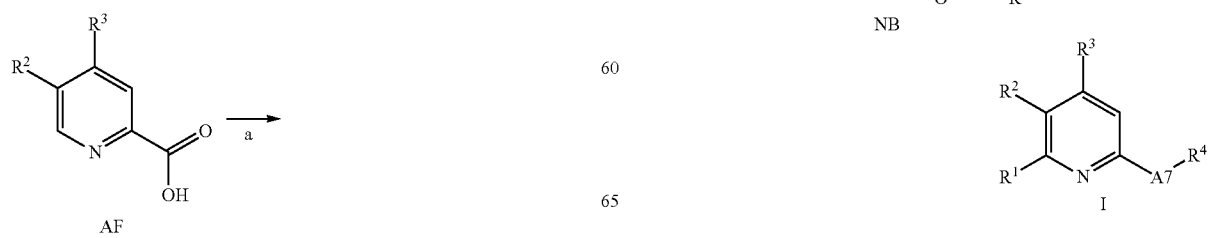

Compound NB can be prepared from NA by oxidation with a suitable oxidizing reagent known to a person skilled in the art (step b), e.g. by treatment with Dess-Martin periodinane in a solvent such as DCM.

Conversion of compound NB to compound I with heterocycle type A7 (step c) can be performed by cyclisation method known to a person skilled in the art, e.g. treatment with hexachloroethane and triphenylphosphine in as solvent such as acetonitrile.

Following the procedure according to scheme 14, compound OA can be obtained from compound DB by substitution with a alkylthiol, e.g. methanethiol and heated in an appropriate solvent such as DMF (step a).

Scheme 14

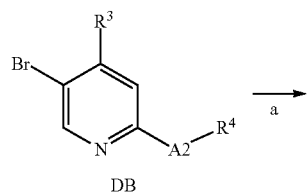

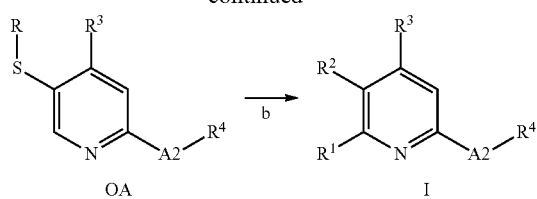

Conversion to compound I can be performed by oxidation of compound OA with a suitable oxidizing reagent under conditions known to a person skilled in the art (step b), e.g. by treatment with 3-chloro perbenzoic acid in dichloromethane at ambient temperature.

Following the procedure described in scheme 15, compound PA can be obtained from compound AF by amide coupling methods known to a person skilled in the art, with the suitably substituted amine, previously prepared by a skilled chemist, in an appropriate solvent such as DCM (step a).

Scheme 15

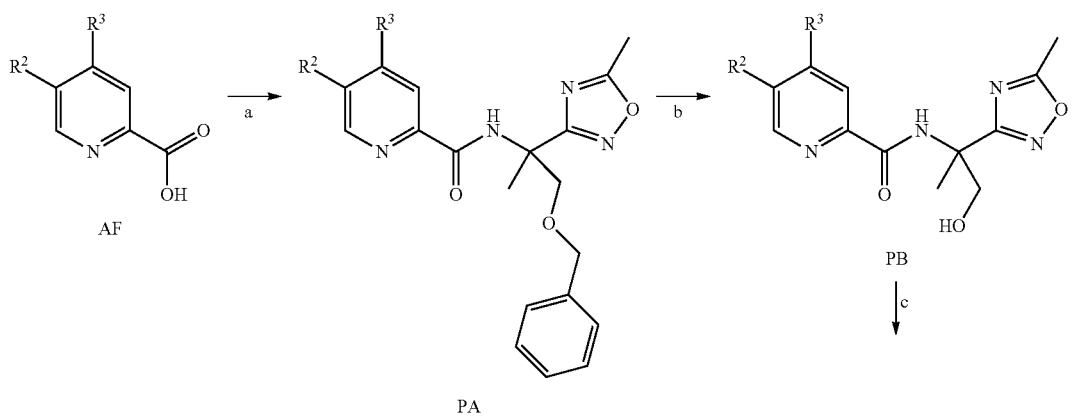

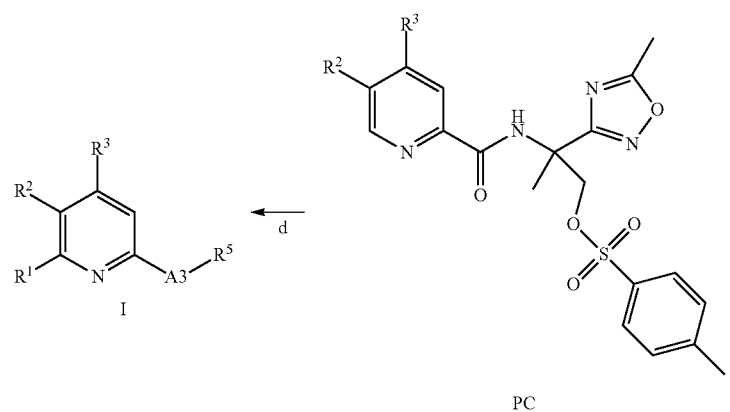

Compound PA can be converted to compound PB (step b) by debenzylation methods known to a person skilled in the art, e.g. treatment by BBr₃ solution in DCM.

Compound PC can be prepared from compound PB by tosylation methods, e.g. 4-methylbenzene-1-sulfonyl chloride with potassium carbonate in presence of dimethylaminopyridine in a solvent such as DCM.

Compound PC can be cyclized to compound I with heterocycle type A3, by heating in a presence of a base e.g. triethylamine, in a solvent such as DMF.

Alternatively, following the procedure according to scheme 14, compound QA can be prepared from I by oxidation with a suitable oxidizing reagent under conditions known to a person skilled in the art, e.g. by treatment with 3-chloro perbenzoic acid in dichloromethane (step a).

Scheme 16

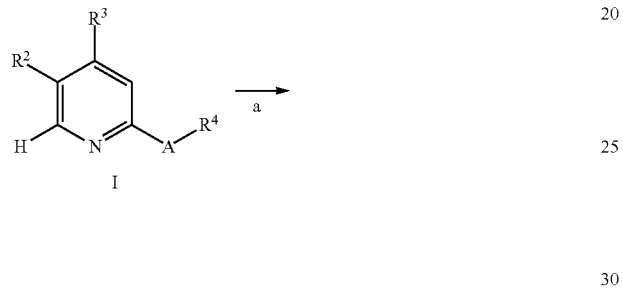

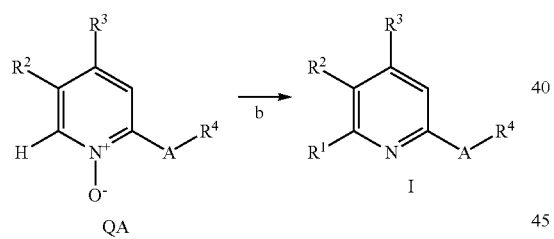

Compound I can be prepared from QA by chlorination methods known to a person skilled in the art, such as treatment with oxalyl chloride in a solvent such as DCM.

The invention also relates to a process for the manufacture of a compound of formula (I) as defined above comprising one of the following steps:

(a) the heating of a compound of formula (A)

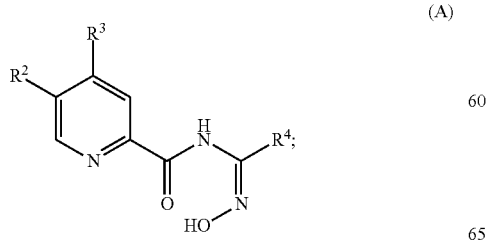

(b) the heating of a compound of formula (B)

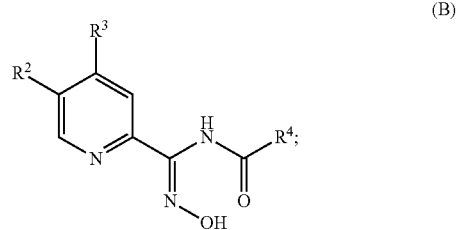

(c) the reaction of a compound of formula (C)

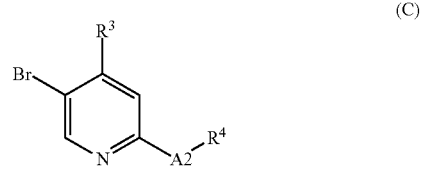

in the presence of haloazetidine or 6-oxa-1-aza-spiro[3.3]heptane, a base and a palladium catalyst;

(d) the reaction of a compound of formula (D)

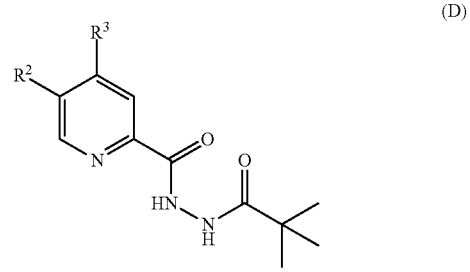

in the presence of trifluoromethanesulfonic anhydride and triphenylphosphine oxide;

(e) the reaction of a compound of formula (E1) or (E2)

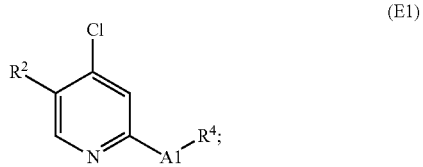

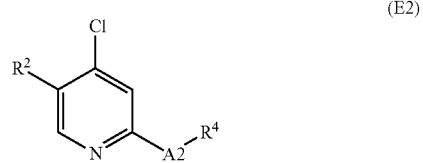

in the presence of HOR, haloazetidine, 6-oxa-1-aza-spiro[3.3]heptane or HSO₂R and a base;

(f) the heating of a compound of formula (F)

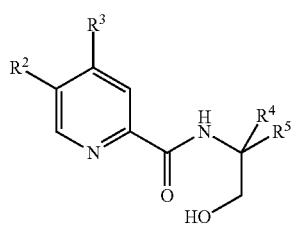

in the presence of Burgess reagent;
(g) the heating of a compound of formula (G)

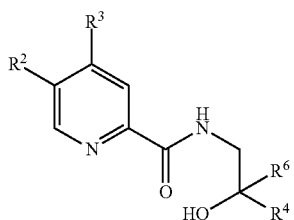

in the presence of methanesulfonic acid;
(h) the heating of a compound of formula (H)

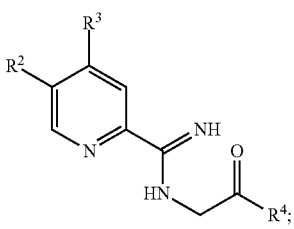

(j) the heating of a compound of formula (J)

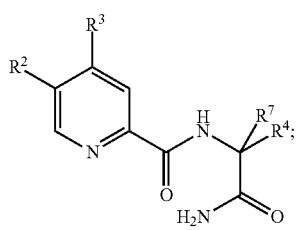

(k) the reaction of a compound of formula (K)

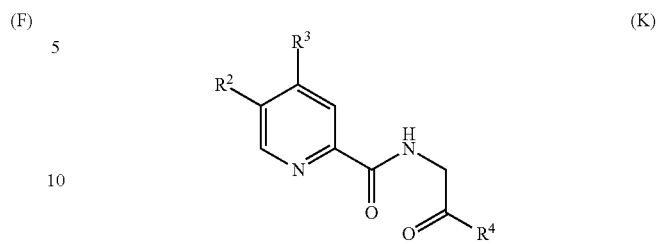

in the presence of hexachloroethane, a base and a phosphine;
(l) the reaction of a compound of formula (L)

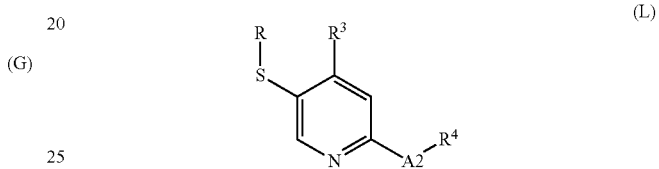

in the presence of an oxidizing agent;
(m) the heating of a compound of formula (M)

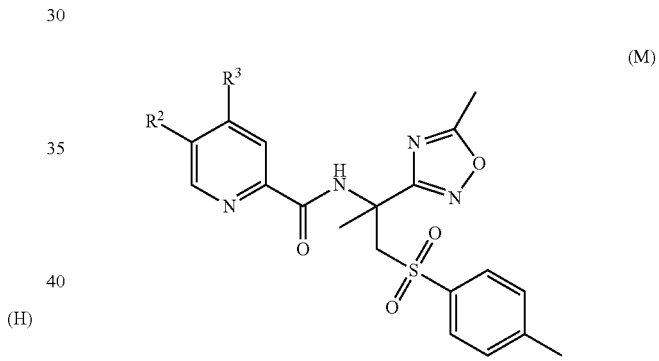

in the presence of a base;
(n) the reaction of a compound of formula (N)

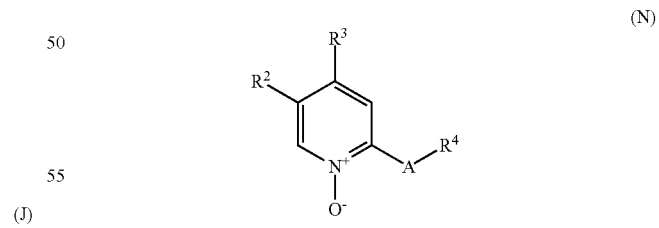

in the presence of a chlorinating agent and DMF; or
(o) the reaction of a compound of formula (C) as defined above in the presence of HSR and a base, and then an oxidation agent;
wherein A, A1 to A8 and $R^1$ to $R^4$ are as defined above and wherein R is alkyl.

Step (a) is for example carried out at 120° C.
Step (b) is for example carried out at 130° C.
Step (c) is for example carried out at 130° C.

Step (d) is carried out for example at room temperature.

In step (e), the base is for example sodium hydride.

The Burgess reagent is commonly known to the person skilled in the art, and is methyl N-(triethylammoniumsulfonyl)carbamate.

Step (g) is for example carried out at 40° C.

Step (h) is for example carried out at 120° C.

Step (j) is for example carried out at 70° C.

In step (k), the base is for example triethylamine. The phosphine is for example triphenylphosphine.

Step (l) can be performed with 3-chloro perbenzoic acid, e.g. in dichloromethane, in particular at ambient temperature.

Step (m) is for example carried out at 80° C., for example in DMF. The base of step (m) is for example triethylamine.

The chlorinating agent is for example oxalyl chloride.

The invention also relates in particular to:

The use of a compound of formula (I) for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, amyotrophic lateral sclerosis, multiple sclerosis, Alzheimer's disease, Parkinson's disease, stroke, transient ischemic attack or uveitis;

The use of a compound according of formula (I) for the preparation of a medicament for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, amyotrophic lateral sclerosis, multiple sclerosis, Alzheimer's disease, Parkinson's disease, stroke, transient ischemic attack or uveitis;

A compound of formula (I) for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, amyotrophic lateral sclerosis, multiple sclerosis, Alzheimer's disease, Parkinson's disease, stroke, transient ischemic attack or uveitis; and A method for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, amyotrophic lateral sclerosis, multiple sclerosis, Alzheimer's disease, Parkinson's disease, stroke, transient ischemic attack or uveitis, which method comprises administering an effective amount of a compound of formula (I) to a patient in need thereof.

The invention particularly relates to a compound of formula (I) for the treatment or prophylaxis of ischemia, reperfusion injury, liver fibrosis or kidney fibrosis, in particular ischemia or reperfusion injury.

The invention particularly relates to a compound of formula (I) for the treatment or prophylaxis of myocardial infarction.

The invention further particularly relates to a compound of formula (I) for the treatment or prophylaxis of age-related macular degeneration, diabetic retinopathy, glaucoma, retinal vein occlusion, retinopathy of prematurity, ocular ischemic syndrome, geographic atrophy or uveitis.

The invention further particularly relates to a compound of formula (I) for the treatment or prophylaxis of amyotrophic lateral sclerosis or multiple sclerosis.

The invention is further directed to a compound of formula (I), when manufactured according to a process according to the invention.

Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compound of formula (I) is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention will now be illustrated by the following examples which have no limiting character.

EXAMPLES

Abbreviations

MPLC=medium pressure liquid chromatography, model Combiflash Companion from TELEDYNE ISCO; MS=mass spectrometry; ESI=electrospray; BINAP=2,2'-bis(diphenylphosphino)-1,1'-binaphthyl; CDI=1,1'-carbonyldiimidazole; $Cs_2CO_3$=cesium carbonate; DCM=dichloromethane; DIPEA=N-ethyl-N-isopropylpropan-2-amine; DBU=1,8-Diazabicyclo[5.4.0]undec-7-ene; DMF=dimethylformamide; DMSO=dimethyl-sulfoxide; dppf=1,1'-bis(diphenylphosphino)ferrocene; EtOH=ethanol; HATU=2-(3H-[1,2,3]triazolo[4,5-b]pyridin-3-yl)-1,1,3,3-tetramethylisouronium hexafluorophosphate (V); HBTU=O-benzotriazole-N,N,N',N'-tetramethyl-uronium-hexafluoro-phosphate; HPLC=LC=high performance liquid chromatography; m-CPBA=meta-chloroperoxybenzoic acid; MeOH=methanol; $NaHCO_3$=sodium hydrogenocarbonate; $Na_2SO_4$=sodium sulfate; $Pd(OAc)_2$=palladium (II) acetate; RT=room temperature; TBTU=O-(benzotriazol-1-yl)-N,N,N',N'-tetramethyl-uronium-tetrafluoroborate; TBME=methyl tert-butylether; THF=tetrahydrofuran; TFA=trifluoroacetic acid; TLC=thin layer chromatography; TMS-CN=Trimethylsilyl cyanide.

Example 1

5-[5-cyclopropyl-4-(cyclopropylmethoxy)pyridin-2-yl]-3-methyl-1,2,4-oxadiazole a) 3-bromo-4-(cyclopropylmethoxy)pyridine

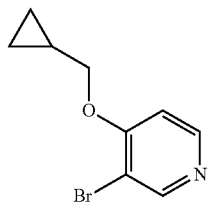 [SMILES: Brc1cnccc1OCC1CC1]

To a solution of 3-bromo-4-chloropyridine (CAS 36953-42-1) (8 g, 41.6 mmol, Eq: 1.00) in dry DMF (100 mL) under argon atmosphere at RT was added cyclopropylmethanol (CAS 2516-33-8) (3.15 g, 3.45 mL, 43.6 mmol, Eq: 1.05) and by portions NaH (1.75 g, 43.6 mmol, Eq: 1.05). The resulting reaction was stirred at RT until gas evolution stopped. The reaction mixture was then stirred at 100° C. for 3 h and controlled by TLC. The reaction was cooled down to RT, quenched by addition of water and the mixture concentrated in vacuo. The residue was redissolved in ethyl acetate, extracted with aqueous $NaHCO_3$ 1M, the organic phase dried over $Na_2SO_4$, filtered and evaporated down to dryness. Flash chromatography with a 120 g $SiO_2$ column, with an eluent mixture of heptane and ethyl acetate to give 8.25 g of light yellow oil (Yield: 87%). MS (ESI, m/z): 228.2 (M).

b) 3-cyclopropyl-4-(cyclopropylmethoxy)pyridine

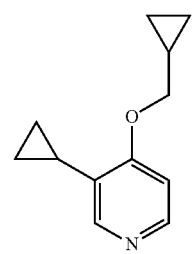 [SMILES: c1cc(OCC2CC2)c(C2CC2)cn1]

To a solution of 3-bromo-4-(cyclopropylmethoxy)pyridine (8.1 g, 35.5 mmol, Eq: 1.00) in a mixture of toluene (150 mL) and water (18 mL) was added potassium cyclopropyltrifluoroborate (CAS 1065010-87-8) (5.52 g, 37.3 mmol, Eq: 1.05), $Cs_2CO_3$ (23.1 g, 71.0 mmol, Eq: 2.0), butyldi-1-adamantylphosphine (382 mg, 1.07 mmol, Eq: 0.03) and $Pd(OAc)_2$ (159 mg, 710 µmol, Eq: 0.02). The reaction mixture was stirred at 125° C. for 7 h. Reaction mixture was cooled down and poured into a separatory funnel, ethyl acetate and water were added. After extraction of the mixture, the organic phase was collected, dried over $Na_2SO_4$ and evaporated down to dryness. Flash chromatography with a 120 g $SiO_2$ column, and an eluent mixture of heptane and ethyl acetate gave 4.6 g of the desired product (Yield 68%). MS (ESI, m/z): 190.3 ($MH^+$).

c) 2-bromo-5-cyclopropyl-4-(cyclopropylmethoxy) pyridine

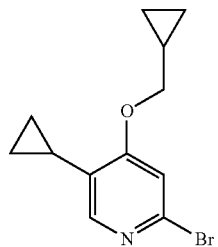 [SMILES: Brc1cc(OCC2CC2)c(C2CC2)cn1]

To a solution of N,N-dimethylethanolamine (1.13 g, 1.28 mL, 12.7 mmol, Eq: 3.0) in hexane (9 mL) under an argon atmosphere at −15° C. was slowly added BuLi 1.6M in hexane (15.9 mL, 25.4 mmol, Eq: 6.0) and the reaction mixture was stirred at −15° C. for 15 min. Addition of 3-cyclopropyl-4-(cyclopropylmethoxy)pyridine (0.8 g, 4.23 mmol, Eq: 1.00) in dry toluene (5 mL) to the reaction at −15° C. was followed by stirring at −15° C. for 1 h. Reaction was then cooled down to −78° C. and a solution of 1,2-dibromotetrachloroethane (4.13 g, 12.7 mmol, Eq: 3.0) in dry toluene (6 mL) was added. The resulting white suspension was then stirred for 1 h at −78° C. and controlled by LC-MS. The reaction was then quenched with water, allowed to warm up to RT and diluted with ethyl acetate. The mixture was poured into a separatory funnel, extracted with aqueous NaHCO₃ 1M. The organic phase was dried over Na₂SO₄ and evaporated down to dryness. Flash chromatography with a 70 g SiO₂ column, and an eluent mixture of heptane and ethyl acetate gave 980 mg of colorless oil (Yield 77%). MS (ESI, m/z): 268.1 (M).

d) 5-cyclopropyl-4-(cyclopropylmethoxy)picolinonitrile

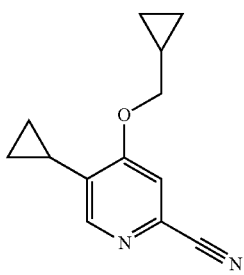 [SMILES: N#Cc1cc(OCC2CC2)c(C2CC2)cn1]

To a solution of 2-bromo-5-cyclopropyl-4-(cyclopropylmethoxy)pyridine (1.15 g, 3.65 mmol, Eq: 1.00) in Dioxane (25 mL) under an argon atmosphere was added copper (I) cyanide (1.31 g, 14.6 mmol, Eq: 4.0), tetraethylammonium cyanide (570 mg, 3.65 mmol, Eq: 1.00), dppf (323 mg, 583 μmol, Eq: 0.16) and Pd₂(dba)₃ (134 mg, 146 μmol, Eq: 0.04). The resulting reaction mixture was stirred at 110° C. for 4 h. Reaction mixture was filtered over a pad of Celite, and the filtrate was poured into a separatory funnel. After dilution with ethyl acetate, extraction with aqueous NaHCO₃ 1M, the organic phase was collected, dried and evaporated down to dryness. Flash chromatography with a 50 g SiO₂ column, and an eluent mixture of heptane and ethyl acetate gave 392 mg of the desired product (Yield 50%). MS (ESI, m/z): 215.3 (MH⁺).

e) 5-cyclopropyl-4-(cyclopropylmethoxy)picolinic acid

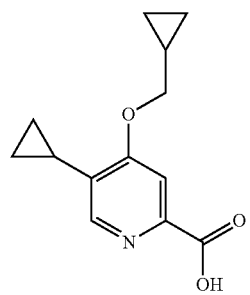 [SMILES: O=C(O)c1cc(OCC2CC2)c(C2CC2)cn1]

To a solution of 5-cyclopropyl-4-(cyclopropylmethoxy) picolinonitrile (200 mg, 933 μmol, Eq: 1.00) in water (4 mL) was added potassium hydroxide (786 mg, 14.0 mmol, Eq: 15.0). The reaction was stirred at 110° C. overnight and monitored by TLC. KOH was neutralized using HCl aqueous solution and the pH was adjusted to 1-2. Afterwards an extraction with DCM/MeOH (4:1) was made and the organic phase was collected, dried and the solvent evaporated. The crude material was purified by MPLC ISCO on SiO₂ column giving 200 mg of compound as a white powder (Yield 92%). MS (ESI, m/z): 234.6 (MH⁺).

f) 5-[5-cyclopropyl-4-(cyclopropylmethoxy)pyridin-2-yl]-3-methyl-1,2,4-oxadiazole

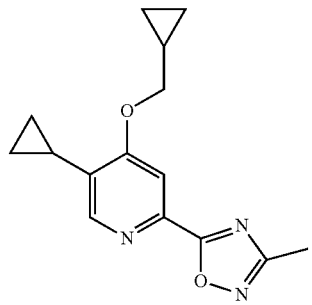 [SMILES: Cc1noc(-c2cc(OCC3CC3)c(C3CC3)cn2)n1]

In a micro-wave vial with DMF (1.5 mL), 5-cyclopropyl-4-(cyclopropylmethoxy)picolinic acid (46.7 mg, 200 μmol, Eq: 1.00) was combined with CDI (32.4 mg, 200 μmol, Eq: 1.0). The reaction mixture was stirred for 30 min at room temperature under Argon. N'-hydroxyacetimidamide (CAS 22059-22-9) (14.8 mg, 200 μmol, Eq: 1.0) was added. The reaction mixture was stirred for 1 h, and then heated to 130° C. with microwave for another 1 h. The reaction was controlled by LC-MS which showed complete conversion. The reaction mixture was directly purified by preparative HPLC without any work-up. MS (ESI, m/z): 272.5 (MH+).

Example 2

5-[5-cyclopropyl-4-(cyclopropylmethoxy)pyridin-2-yl]-3-phenyl-1,2,4-oxadiazole

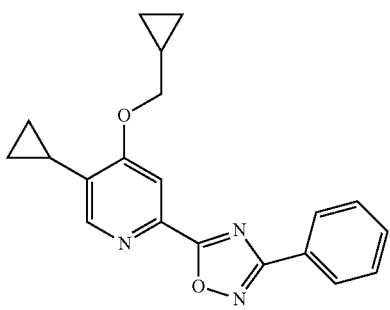 [SMILES: c1ccc(-c2noc(-c3cc(OCC4CC4)c(C4CC4)cn3)n2)cc1]

The title compound was synthesized in analogy to Example 1f, using 5-cyclopropyl-4-(cyclopropylmethoxy) picolinic acid and N'-hydroxybenzimidamide (CAS 613-92-3) as starting materials, and directly purified by preparative HPLC without any work-up. MS (ESI, m/z): 334.5 (MH+).

Example 3

3-cyclopropyl-5-[5-cyclopropyl-4-(cyclopropylmethoxy)pyridin-2-yl]-1,2,4-oxadiazole

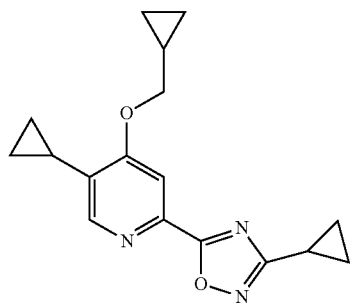 [SMILES: c1c(-c2nc(C3CC3)no2)ncc(C2CC2)c1OCC1CC1]

The title compound was synthesized in analogy to Example 1f, using 5-cyclopropyl-4-(cyclopropylmethoxy) picolinic acid and N'-hydroxycyclopropanecarboximidamide (CAS 51285-13-3) as starting materials, and directly purified by preparative HPLC without any work-up. MS (ESI, m/z): 298.5 (MH+).

Example 4

3-cyclopentyl-5-[5-cyclopropyl-4-(cyclopropylmethoxy)pyridin-2-yl]-1,2,4-oxadiazole

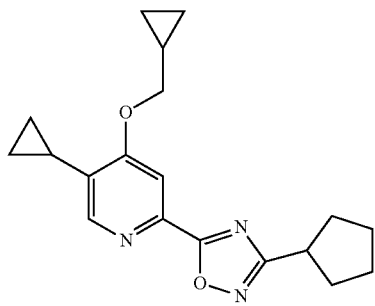 [SMILES: c1c(-c2nc(C3CCCC3)no2)ncc(C2CC2)c1OCC1CC1]

The title compound was synthesized in analogy to Example 1f, using 5-cyclopropyl-4-(cyclopropylmethoxy) picolinic acid and N'-hydroxycyclopentanecarboximidamide (CAS 99623-12-8) as starting materials, and directly purified by preparative HPLC without any work-up. MS (ESI, m/z): 326.3 (MH+).

Example 5

3-benzyl-5-[5-cyclopropyl-4-(cyclopropylmethoxy) pyridin-2-yl]-1,2,4-oxadiazole

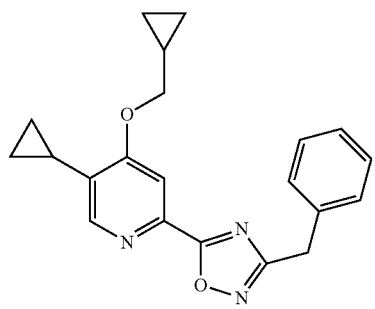 [SMILES: c1ccc(Cc2noc(-c3cc(OCC4CC4)c(C4CC4)cn3)n2)cc1]

The title compound was synthesized in analogy to Example 1f, using 5-cyclopropyl-4-(cyclopropylmethoxy) picolinic acid and N'-hydroxy-2-phenylacetimidamide (CAS 19227-11-3) as starting materials, and directly purified by preparative HPLC without any work-up. MS (ESI, m/z): 348.2 (MH+).

Example 6

3-tert-butyl-5-[5-cyclopropyl-4-(cyclopropyl-methoxy)pyridin-2-yl]-1,2,4-oxadiazole

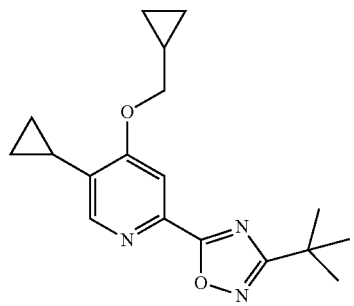 [SMILES: CC(C)(C)c1noc(-c2cc(OCC3CC3)c(C3CC3)cn2)n1]

The title compound was synthesized in analogy to Example 1f, using 5-cyclopropyl-4-(cyclopropylmethoxy)picolinic acid and N'-hydroxypivalimidamide (CAS 42956-75-2) as starting materials, and directly purified by preparative HPLC without any work-up. MS (ESI, m/z): 314.2 (MH+).

Example 7

3-cyclopropyl-5-[5-cyclopropyl-4-(2,2,2-trifluoroethoxy)pyridin-2-yl]-1,2,4-oxadiazole a) 3-bromo-4-(2,2,2-trifluoroethoxy)pyridine

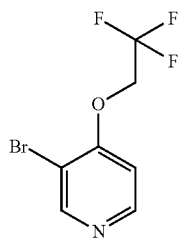

To a solution of 3-bromo-4-chloropyridine (CAS 36953-42-1) (25 g, 130 mmol, Eq: 1.00) in DMF (333 mL) was added 2,2,2-trifluoroethanol (CAS 75-89-8) (19.5 g, 195 mmol, Eq: 1.5) and potassium tert-butoxide (21.9 g, 195 mmol, Eq: 1.5). The reaction was stirred overnight at 110° C. The solvent was partially evaporated and partitioned between NaHCO₃ aqueous saturated solution and ethyl acetate. The organic layer was dried over Na₂SO₄ and evaporated. Product used as a crude (85% yield). MS (ESI, m/z): 257.3 (MH+).

b) 3-cyclopropyl-4-(2,2,2-trifluoroethoxy)pyridine

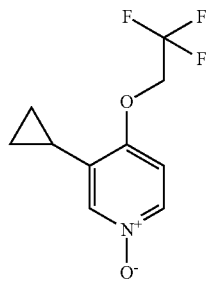 [SMILES: [O-][n+]1ccc(OCC(F)(F)F)c(C2CC2)c1]

To a solution of 3-bromo-4-(2,2,2-trifluoroethoxy)pyridine (28.44 g, 88.9 mmol, Eq: 1.00) in a mixture of toluene (275 mL) and water (32.5 mL) was added potassium cyclopropyltrifluoroborate (CAS 1065010-87-8) (14.5 g, 97.8 mmol, Eq: 1.1), palladium (II) acetate (798 mg, 3.55 mmol, Eq: 0.04), butyldi-1-Adamantylphosphine (1.27 g, 3.55 mmol, Eq: 0.04) and Cs₂CO₃ (72.4 g, 222 mmol, Eq: 2.5) under an argon atmosphere. The reaction mixture was stirred over night at 115° C. and controlled by TLC. The reaction mixture was extracted with ethyl acetate and water. The organic phase was dried over Na₂SO₄ and evaporated down to dryness. The crude material was purified by MPLC ISCO on SiO₂ column with a gradient heptane in ethyl acetate giving yellow viscous oil (Yield 72%). MS (ESI, m/z): 218.5 (MH+).

c) 3-cyclopropyl-4-(2,2,2-trifluoroethoxy)pyridine 1-oxide

To a solution of 3-cyclopropyl-4-(2,2,2-trifluoroethoxy)pyridine (13.89 g, 64 mmol, Eq: 1.00) in DCM (355 mL) was added m-CPBA (16.6 g, 95.9 mmol, Eq: 1.5). Reaction was stirred overnight at RT. Extraction with NaHCO₃ saturated aqueous solution and DCM. Organic layer was dried on Na₂SO₄ and evaporated. Column on SiO₂ using MPLC ISCO with a gradient DCM/MeOH (Yield 68%). MS (ESI, m/z): 234.5 (MH+).

d) 5-cyclopropyl-4-(2,2,2-trifluoroethoxy)picolinonitrile

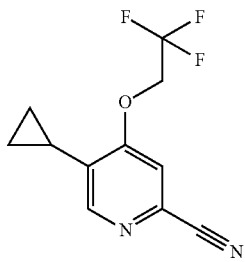 [SMILES: N#Cc1cc(OCC(F)(F)F)c(C2CC2)cn1]

3-cyclopropyl-4-(2,2,2-trifluoroethoxy)pyridine 1-oxide (10.20 g, 43.7 mmol, Eq: 1.00) was dissolved in DCM (163 mL). Trimethylsilanecarbonitrile (CAS 7677-24-9) (5.64 g, 7.11 mL, 56.9 mmol, Eq: 1.3) was then added dropwise followed by dimethylcarbamic chloride (7.06 g, 6.03 mL, 65.6 mmol, Eq: 1.5). The reaction mixture was stirred at room temperature over night. Saturated aqueous NaHCO$_3$ (20 mL) was added with stirring. The reaction mixture was poured into DCM and extracted with H$_2$O. The organic layers were dried over Na$_2$SO$_4$ and concentrated in vacuo. The crude material was purified by flash chromatography on SiO$_2$ using MPLC ISCO with a gradient heptane in ethyl acetate (Yield 64%). MS (ESI, m/z): 243.5 (MH+).

e) 5-cyclopropyl-4-(2,2,2-trifluoroethoxy)picolinic acid

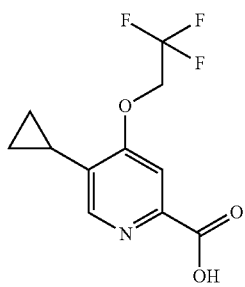 [SMILES: O=C(O)c1cc(OCC(F)(F)F)c(C2CC2)cn1]

5-cyclopropyl-4-(2,2,2-trifluoroethoxy)picolinonitrile (6.87 g, 28.4 mmol, Eq: 1.00) was dissolved in HCl 25% aqueous sol (170 mL, 1.4 mol, Eq: 50.0). Reaction was heated at 110° C. After 3 h reaction was complete. Reaction was cooled down to RT. HCl was neutralized using 6M NaOH aqueous solution followed by NaOH pellets. Then the pH was adjusted to 1-2 with HCl 2M. The precipitate formed was filtered off to give title compound (Yield 99%). MS (ESI, m/z): 262.5 (MH+).

f) 3-cyclopropyl-5-[5-cyclopropyl-4-(2,2,2-trifluoroethoxy)pyridin-2-yl]-1,2,4-oxadiazole

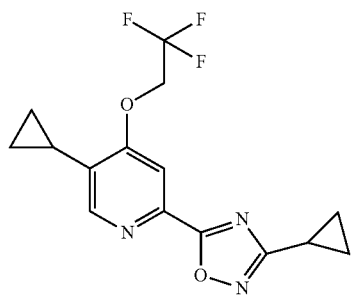 [SMILES: FC(F)(F)COc1cc(-c2nc(C3CC3)no2)ncc1C1CC1]

To a solution of 5-cyclopropyl-4-(2,2,2-trifluoroethoxy) picolinic acid (50 mg, 191 µmol, Eq: 1.00) in dry DMF (1.5 mL) was added CDI (34.1 mg, 211 µmol, Eq: 1.1) and reaction stirred for 30 min at RT N'-hydroxycyclopropanecarboximidamide (CAS 51285-13-3) (211 µmol, Eq: 1.1) was added, stirred for 1 h at RT and after that overnight at 120° C. The reaction mixture was controlled by LC-MS. The reaction was directly purified by preparative HPLC without any further work-up. MS (ESI, m/z): 326 (MH+).

Example 8

5-[5-cyclopropyl-4-(2,2,2-trifluoroethoxy)pyridin-2-yl]-3-(trifluoromethyl)-1,2,4-oxadiazole

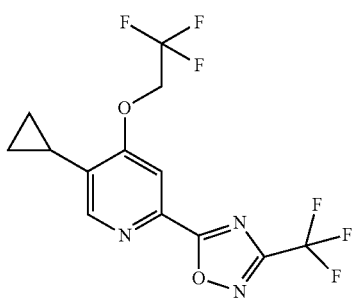 [SMILES: FC(F)(F)COc1cc(-c2nc(C(F)(F)F)no2)ncc1C1CC1]

The title compound was synthesized in analogy to Example 7f, using 5-cyclopropyl-4-(2,2,2-trifluoroethoxy) picolinic acid and 2,2,2-trifluoro-N'-hydroxyacetimidamide (CAS 4314-35-6) as starting materials, and directly purified by preparative HPLC without any further work-up. MS (ESI, m/z): 354 (MH+).

Example 9

5-cyclopropyl-3-[5-cyclopropyl-4-(cyclopropyl-methoxy)pyridin-2-yl]-1,2,4-oxadiazole a) 5-cyclopropyl-4-(cyclopropylmethoxy)-N'-hydroxypicolinimidamide

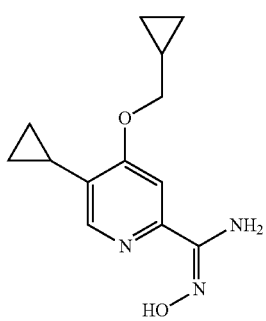 [SMILES: N/C(=N/O)c1cc(OCC2CC2)c(C2CC2)cn1]

To a solution of 5-cyclopropyl-4-(cyclopropylmethoxy) picolinonitrile (synthesis described previously as Example 1d) (390 mg, 1.82 mmol, Eq: 1.00) in EtOH (4 mL) was added hydroxylamine hydrochloride (126 mg, 1.82 mmol, Eq: 1.00) and triethylamine (184 mg, 254 µL, 1.82 mmol, Eq: 1.00). The reaction mixture was stirred at 70° C. for 4 h and controlled by LC-MS which showed complete conversion to the desired product. The reaction mixture was diluted with ethyl acetate, poured into a separatory funnel, washed with water, and the organic phase dried over $Na_2SO_4$ and evaporated down to dryness. Flash chromatography with a 20 g $SiO_2$ column, eluent mixture of DCM and MeOH gave 418 mg of the desired product (Yield 88%). MS (ESI, m/z): 248.2 (MH+).

b) 5-cyclopropyl-3-[5-cyclopropyl-4-(cyclopropyl-methoxy)pyridin-2-yl]-1,2,4-oxadiazole

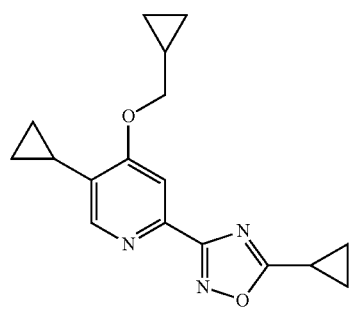 [SMILES: c1c(-c2noc(C3CC3)n2)ncc(C2CC2)c1OCC1CC1]

To a solution of cyclopropanecarboxylic acid (CAS 1759-53-1) (179 µmol, Eq: 1.05) in dry DMF (1.0 mL) was added CDI (28.9 mg, 179 µmol, Eq: 1.05) and the resulting reaction mixture was stirred at RT for 45 min, followed by addition of 5-cyclopropyl-4-(cyclopropylmethoxy)-N'-hydroxypicolinimidamide (42.0 mg, 170 µmol, Eq: 1.00). The reaction was stirred at RT for 2 h and controlled by LC-MS which showed complete consumption of the starting material to produce the intermediate. The reaction was then heated at 130° C. in a micro-wave for 45 min, controlled by LC-MS. The reaction was directly purified by preparative HPLC without any work-up. MS (ESI, m/z): 298.4 (MH+).

Example 10

5-tert-butyl-3-[5-cyclopropyl-4-(cyclopropyl-methoxy)pyridin-2-yl]-1,2,4-oxadiazole

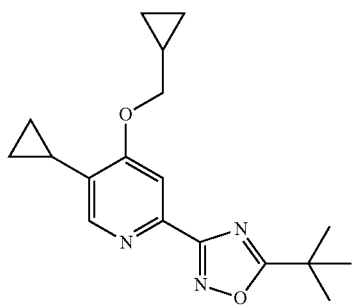 [SMILES: CC(C)(C)c1nc(-c2cc(OCC3CC3)c(C3CC3)cn2)no1]

The title compound was synthesized in analogy to Example 9b, using pivalic acid (CAS 75-98-9) and 5-cyclopropyl-4-(cyclopropylmethoxy)-N'-hydroxypicolinimidamide as starting materials, and directly purified by preparative HPLC without any work-up. MS (ESI, m/z): 354 (MH+).

Example 11

2-[5-cyclopropyl-4-(cyclopropylmethoxy)pyridin-2-yl]-4,4-diethyl-5H-1,3-oxazole a) 5-cyclopropyl-4-(cyclopropylmethoxy)-N-(3-(hydroxymethyl)pentan-3-yl)picolinamide

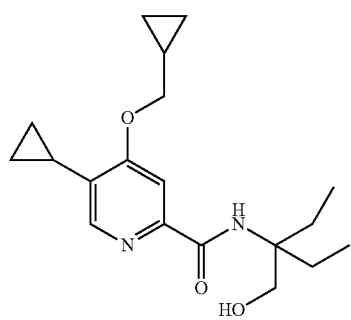 [SMILES: CCC(CC)(CO)NC(=O)c1cc(OCC2CC2)c(C2CC2)cn1]

To a solution of 5-cyclopropyl-4-(cyclopropylmethoxy) picolinic acid (previously described as Example 1e) (50 mg, 0.214 mmol, Eq: 1.00) in DCM (2 mL) was added 4-(4,6-dimethoxy[1.3.5]triazin-2-yl)-4-methylmorpholinium chloride hydrate (CAS 3945-69-5) (69.5 mg, 0.236 mmol, Eq: 1.1). The reaction was stirred 30 min at RT. Then 2-amino-2-ethylbutan-1-ol (27.6 mg, 0.236 mmol, Eq: 1.1) (CAS 39884-49-6) was added and the reaction stirred at RT overnight. LC-MS showed reaction was complete. Extraction with $NaHCO_3$ saturated aqueous solution and column-ing on $SiO_2$ with a gradient heptane/ethyl acetate gave 30 mg of the title compound (Yield 42%). MS (ESI, m/z): 333.3 (MH+).

b) 2-[5-cyclopropyl-4-(cyclopropylmethoxy)pyridin-2-yl]-4,4-diethyl-5H-1,3-oxazole

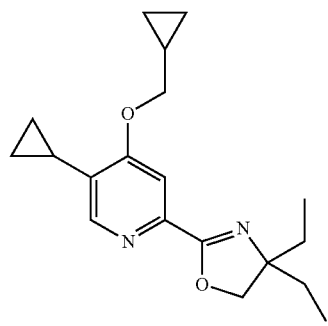 [SMILES: CCC1(CC)COC(c2cc(OCC3CC3)c(C3CC3)cn2)=N1]

To a solution of 5-cyclopropyl-4-(cyclopropylmethoxy)-N-(3-(hydroxymethyl)pentan-3-yl)picolinamide (34 mg, 102 μmol, Eq: 1.00) (carefully dried) in dry THF was added Burgess reagent (25.6 mg, 107 μmol, Eq: 1.05). Reaction was stirred at RT under argon overnight. LC-MS showed reaction was complete. Evaporation of the solvent and extraction with NaHCO$_3$ saturated aqueous solution and ethyl acetate. Organic layer was dried on Na$_2$SO$_4$ and evaporated. Column on SiO$_2$ with a gradient heptane/ethyl acetate (Yield 62%). MS (ESI, m/z): 315.2 (MH+).

Example 12

3-[5-cyclopropyl-4-(cyclopropylmethoxy)pyridin-2-yl]-5-(methoxymethyl)-1,2,4-oxadiazole

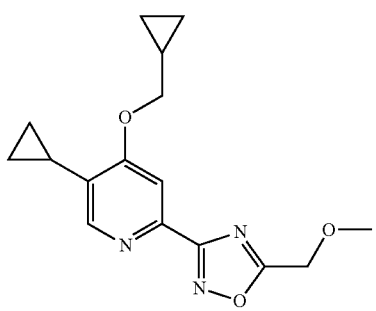 [SMILES: COCc1nc(-c2cc(OCC3CC3)c(C3CC3)cn2)no1]

The title compound was synthesized in a similar manner as Example 9b, using 5-cyclopropyl-4-(cyclopropylmethoxy)-N'-hydroxypicolinimidamide with potassium carbonate (Eq: 1.0) and 2-methoxyacetyl chloride (CAS 38870-89-2) as starting materials and, directly purified by preparative HPLC without any work-up. MS (ESI, m/z): 302.3 (MH+).

Example 13

3-[5-cyclopropyl-4-(cyclopropylmethoxy)pyridin-2-yl]-5-ethyl-1,2,4-oxadiazole

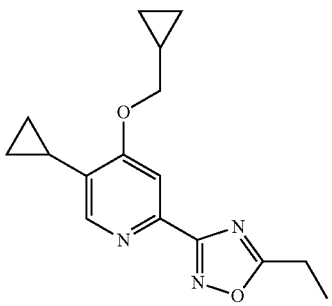 [SMILES: CCc1nc(-c2cc(OCC3CC3)c(C3CC3)cn2)no1]

The title compound was synthesized in a similar manner as Example 9b, using 5-cyclopropyl-4-(cyclopropylmethoxy)-N'-hydroxypicolinimidamide with potassium carbonate (Eq: 1.0) and propionyl chloride (CAS 79-03-8) as starting materials, and directly purified by preparative HPLC without any work-up. MS (ESI, m/z): 286.2 (MH+).

Example 14

3-[5-cyclopropyl-4-(cyclopropylmethoxy)pyridin-2-yl]-5-propan-2-yl-1,2,4-oxadiazole

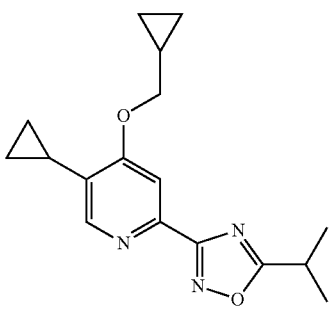 [SMILES: CC(C)c1nc(-c2cc(OCC3CC3)c(C3CC3)cn2)no1]

The title compound was synthesized in a similar manner as Example 9b, using 5-cyclopropyl-4-(cyclopropylmethoxy)-N'-hydroxypicolinimidamide with potassium carbonate (Eq: 1.0) and isobutyryl chloride (CAS 79-30-1) as starting materials, and directly purified by preparative HPLC without any work-up. MS (ESI, m/z): 300.3 (MH+).

Example 15

3-cyclopropyl-5-[5-(3,3-difluoroazetidin-1-yl)-4-(2,2,2-trifluoroethoxy)pyridin-2-yl]-1,2,4-oxadiazole a) 3-bromo-4-(2,2,2-trifluoroethoxy)pyridine 1-oxide

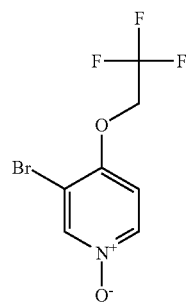 [SMILES: [O-][n+]1ccc(OCC(F)(F)F)c(Br)c1]

To a solution of 3-bromo-4-(2,2,2-trifluoroethoxy)pyridine (previously described as Example 7a) (21 g, 67.3 mmol, Eq: 1.00) in DCM (400 mL) was added by portions m-CPBA (19.6 g, 87.4 mmol, Eq: 1.3). The reaction mixture was then stirred over the week-end at RT and monitored by LC-MS. Reaction mixture was poured into a separatory funnel and extracted with aqueous NaHCO₃ 1M. Aqueous phase was back-extracted with a mixture of ethyl acetate and organic phases were combined, dried over Na₂SO₄ and evaporated down to dryness. Flash chromatography with a 330 g SiO₂ column, eluent mixture of DCM and MeOH giving 16.2 g of the desired product (Yield 88%). MS (ESI, m/z): 272.3 (M).

b) 5-bromo-4-(2,2,2-trifluoroethoxy)picolinonitrile

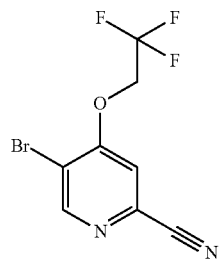 [SMILES: N#Cc1cc(OCC(F)(F)F)c(Br)cn1]

3-bromo-4-(2,2,2-trifluoroethoxy)pyridine 1-oxide (21.5 g, 79 mmol, Eq: 1.00) was combined with DCM (344 mL). Trimethylsilanecarbonitrile (11.8 g, 14.8 mL, 119 mmol, Eq: 1.5) was then added dropwise followed by dimethylcarbamic chloride (12.7 g, 10.9 mL, 119 mmol, Eq: 1.5). The reaction mixture was stirred at room temperature over night. Saturated aqueous NaHCO₃ (20 mL) was added with stirring. The reaction mixture was poured into DCM and extracted with H₂O. The organic layers were dried over Na₂SO₄ and concentrated in vacuo. The crude material was purified by flash chromatography on SiO₂ using MPLC ISCO with a eluent gradient of heptane/ethyl acetate (Yield 27%). MS (ESI, m/z): 281.3 (M).

c) 5-(3,3-difluoroazetidin-1-yl)-4-(2,2,2-trifluoroethoxy)picolinonitrile

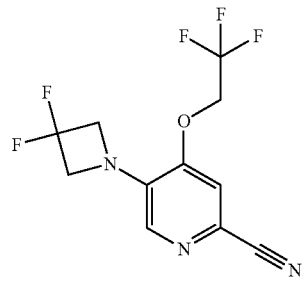 [SMILES: N#Cc1cc(OCC(F)(F)F)c(N2CC(F)(F)C2)cn1]

To a solution of 5-bromo-4-(2,2,2-trifluoroethoxy)picolinonitrile (587 mg, 2.09 mmol, Eq: 1.00) in dry toluene (10.4 mL) in a schlenk tube was added 3,3-difluoroazetidine hydrochloride (CAS 288315-03-7) (298 mg, 2.3 mmol, Eq: 1.1), Cs2CO3 (1.36 g, 4.18 mmol, Eq: 2.0), Pd(OAc)₂ (46.9 mg, 209 µmol, Eq: 0.1) and BINAP (130 mg, 209 µmol, Eq: 0.1). The reaction mixture was heated to 120° C. and stirred for 1 h. Reaction mixture filtered over a pad of Celite, diluted with ethyl acetate, organic phase extracted with aqueous saturated NaHCO₃, dried over Na₂SO₄ and evaporated down to dryness. The crude material was purified by flash chromatography (SiO₂, 50 g, gradient ethyl acetate in heptane) giving 480 mg (Yield 78%) of the desired compound. MS (ESI, m/z): 294.2 (MH+).

d) 5-(3,3-difluoroazetidin-1-yl)-4-(2,2,2-trifluoroethoxy)picolinic acid

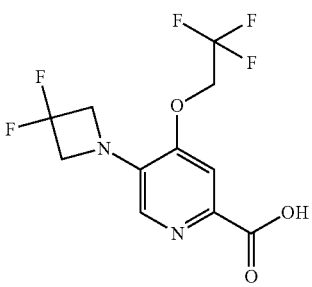 [SMILES: O=C(O)c1cc(OCC(F)(F)F)c(N2CC(F)(F)C2)cn1]

To a solution of 5-(3,3-difluoroazetidin-1-yl)-4-(2,2,2-trifluoroethoxy)picolinonitrile (680 mg, 2.32 mmol, Eq: 1.00) in EtOH (7.73 mL) in a schlenk tube was added KOH 4M aqueous solution (651 mg, 11.6 mmol, Eq: 5.0). The reaction mixture was heated to 105° C. and stirred for 2 h. The reaction mixture was poured in a separatory funnel with a mixture of ethyl acetate and HCl 6.9M (2.69 mL, 18.6 mmol, Eq: 8.0) and water, extraction, the organic phase were collected, dried over Na₂SO₄ and evaporated down to give 397 mg of the desired product as an off-white solid (Yield 54%). MS (ESI, m/z): 311.2 (MH–).

e) 3-cyclopropyl-5-[5-(3,3-difluoroazetidin-1-yl)-4-(2,2,2-trifluoroethoxy)pyridin-2-yl]-1,2,4-oxadiazole

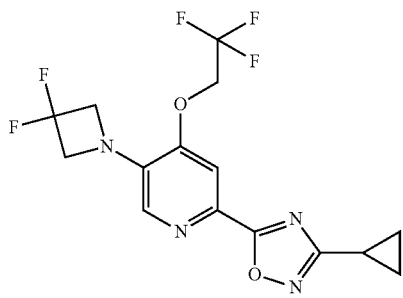 [SMILES: FC(F)(F)COc1cc(-c2nc(C3CC3)no2)ncc1N1CC(F)(F)C1]

In a 5 mL sealed vial, 5-(3,3-difluoroazetidin-1-yl)-4-(2,2,2-trifluoroethoxy)picolinic acid (100 mg, 320 µmol, Eq: 1.00) and CDI (54.5 mg, 336 µmol, Eq: 1.05) were combined with DMF (1.5 mL). The reaction mixture was stirred at room temp for 30 min. N'-hydroxycyclopropanecarboximidamide (CAS 51285-13-3) (336 µmol, Eq: 1.05) was added and the mixture was stirred at room temp for 1 h. The reaction mixture was then heated to 120° C. for 4 h. The reaction mixture was poured into EtOAc and extracted with saturated NaHCO$_3$ aqueous solution. The organic layers were dried over Na$_2$SO$_4$ and concentrated in vacuo. The crude material was purified by flash chromatography (SiO$_2$, 10 g, with a gradient ethyl acetate in heptane) to give 33.6 mg of the title compound (Yield 27%). MS (ESI, m/z): 377.4 (MH+).

Example 16

5-[5-(3,3-difluoroazetidin-1-yl)-4-(2,2,2-trifluoroethoxy)pyridin-2-yl]-3-methyl-1,2,4-oxadiazole

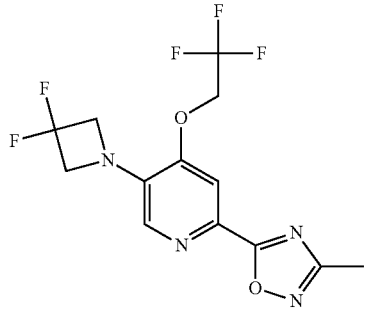 [SMILES: Cc1noc(-c2cc(OCC(F)(F)F)c(N3CC(F)(F)C3)cn2)n1]

The title compound was synthesized in analogy to Example 15e, using 5-(3,3-difluoroazetidin-1-yl)-4-(2,2,2-trifluoroethoxy)picolinic acid and N'-hydroxyacetimidamide (CAS 22059-22-9) as starting materials, and directly purified by flash chromatography (SiO$_2$, 10 g, gradient ethyl acetate in heptane) giving 26 mg of desired compound (Yield 23%). MS (ESI, m/z): 351.2 (MH+).

Example 17

3-tert-butyl-5-[5-(3,3-difluoroazetidin-1-yl)-4-(2,2,2-trifluoroethoxy)pyridin-2-yl]-1,2,4-oxadiazole

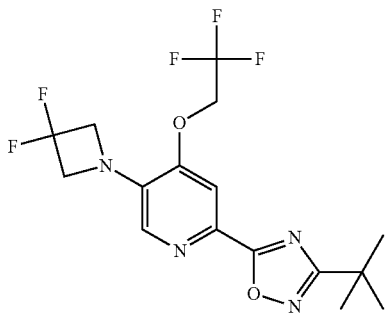 [SMILES: CC(C)(C)c1noc(-c2cc(OCC(F)(F)F)c(N3CC(F)(F)C3)cn2)n1]

The title compound was synthesized in analogy to Example 15e, using 5-(3,3-difluoroazetidin-1-yl)-4-(2,2,2-trifluoroethoxy)picolinic acid and N'-hydroxypivalimidamide (CAS 42956-75-2) as starting materials, and directly purified by flash chromatography (SiO$_2$, 10 g, gradient ethyl acetate in heptane giving 55 mg of desired compound (Yield 44%). MS (ESI, m/z): 393.3 (MH+).

Example 18

[3-[5-cyclopropyl-4-(cyclopropylmethoxy)pyridin-2-yl]-1,2,4-oxadiazol-5-yl]methanol

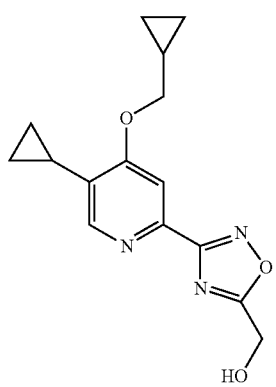 [SMILES: OCc1nc(-c2cc(OCC3CC3)c(C3CC3)cn2)no1]

The title compound was synthesized in a similar manner as Example 9b, using 5-cyclopropyl-4-(cyclopropylmethoxy)-N'-hydroxypicolinimidamide with potassium carbonate (Eq: 1.00) and 2-methoxyacetyl chloride (CAS 38870-89-2) as starting materials and after microwave heating was followed by addition of NaOH 4M aqueous solution (Eq: 1.5) Reaction was stirred overnight at 80° C. and directly purified by preparative HPLC without any work-up. MS (ESI, m/z): 288.1 (MH+).

Example 19

3-[5-cyclopropyl-4-(cyclopropylmethoxy)pyridin-2-yl]-5-(trifluoromethyl)-1,2,4-oxadiazole

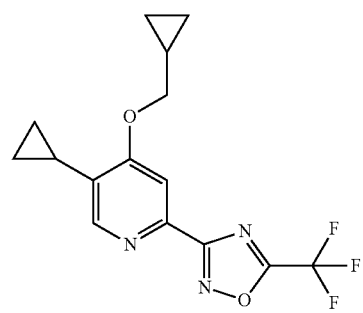 [SMILES: FC(F)(F)c1nc(-c2cc(OCC3CC3)c(C3CC3)cn2)no1]

The title compound was synthesized in a similar manner as Example 9b, using 5-cyclopropyl-4-(cyclopropyl-methoxy)-N'-hydroxypicolinimidamide with triethylamine (Eq: 1.1) and 2,2,2-trifluoroacetic anhydride (CAS 407-25-0) as starting materials in DCM and heated at 70° C. with microwave. Solvent was removed in vacuo, residue redissolved in DMF and directly purified by preparative HPLC to give the desired compound. MS (ESI, m/z): 326.2 (MH+).

Example 20

(4S)-4-tert-butyl-2-[5-cyclopropyl-4-(cyclopropyl-methoxy)pyridin-2-yl]-4,5-dihydro-1,3-oxazole

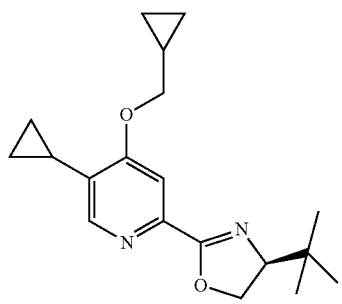 [SMILES: CC(C)(C)[C@H]1COC(c2cc(OCC3CC3)c(C3CC3)cn2)=N1]

The title compound was synthesized in analogy to Example 11, using 5-cyclopropyl-4-(cyclopropylmethoxy) picolinic acid (previously described as Example 1e) and (S)-2-amino-3,3-dimethylbutan-1-ol (CAS 112245-13-3) as starting materials for the first step. MS (ESI, m/z): 315.2 (MH+).

Example 21

2-[5-cyclopropyl-4-(cyclopropylmethoxy)pyridin-2-yl]-4-ethyl-4,5-dihydro-1,3-oxazole

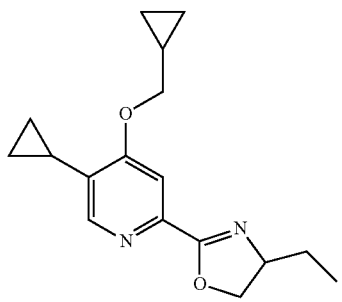 [SMILES: CCC1COC(c2cc(OCC3CC3)c(C3CC3)cn2)=N1]

The title compound was synthesized in analogy to Example 11, using 5-cyclopropyl-4-(cyclopropylmethoxy) picolinic acid (previously described as Example 1e) and 2-aminobutan-1-ol (CAS 96-20-8) as starting materials for the first step. MS (ESI, m/z): 287.2 (MH+).

Example 22

2-[5-cyclopropyl-4-(cyclopropylmethoxy)pyridin-2-yl]-3-oxa-1-azaspiro[4.5]dec-1-ene

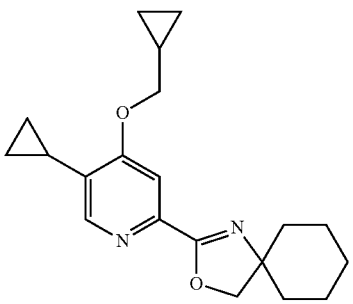 [SMILES: c1c(C2=NC3(CCCCC3)CO2)ncc(C2CC2)c1OCC1CC1]

The title compound was synthesized in analogy to Example 11, using 5-cyclopropyl-4-(cyclopropylmethoxy) picolinic acid (previously described as Example 1e) and (1-aminocyclohexyl)methanol (CAS 4313-56-8) as starting materials for the first step. MS (ESI, m/z): 327.3 (MH+).

Example 23

1-[3-[5-cyclopropyl-4-(cyclopropylmethoxy)pyridin-2-yl]-1,2,4-oxadiazol-5-yl]cyclopropan-1-ol

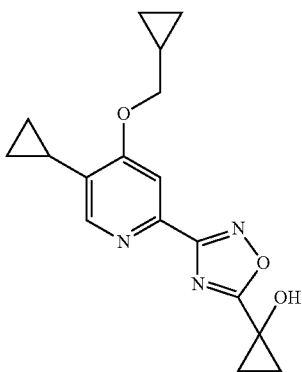 [SMILES: OC1(c2nc(-c3cc(OCC4CC4)c(C4CC4)cn3)no2)CC1]

The title compound was synthesized in analogy to Example 9b, using 1-hydroxycyclopropanecarboxylic acid (CAS 17994-25-1) and 5-cyclopropyl-4-(cyclopropylmethoxy)-N'-hydroxypicolinimidamide as starting materials, and directly purified by preparative HPLC without any work-up. MS (ESI, m/z): 314.0 (MH+).

Example 24

3-[5-cyclopropyl-4-(cyclopropylmethoxy)pyridin-2-yl]-5-(1-methylcyclopropyl)-1,2,4-oxadiazole

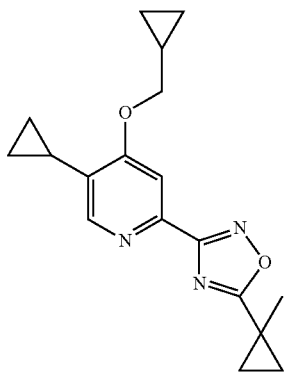 [SMILES: CC1(c2nc(-c3cc(OCC4CC4)c(C4CC4)cn3)no2)CC1]

The title compound was synthesized in analogy to Example 9b, using 1-methylcyclopropanecarboxylic acid (CAS 6914-76-7) and 5-cyclopropyl-4-(cyclopropylmethoxy)-N'-hydroxypicolinimidamide as starting materials, and directly purified by preparative HPLC without any work-up. MS (ESI, m/z): 312.1 (MH+).

Example 25

1-[3-[5-cyclopropyl-4-(cyclopropylmethoxy)pyridin-2-yl]-1,2,4-oxadiazol-5-yl]cyclopropane-1-carboxamide

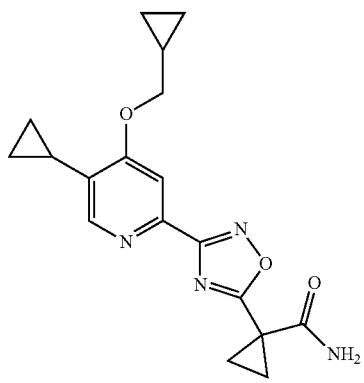 [SMILES: NC(=O)C1(c2nc(-c3cc(OCC4CC4)c(C4CC4)cn3)no2)CC1]

The title compound was synthesized in analogy to Example 9b, using 1-carbamoylcyclopropanecarboxylic acid (CAS 6914-74-5) and 5-cyclopropyl-4-(cyclopropylmethoxy)-N'-hydroxypicolinimidamide as starting materials, and directly purified by preparative HPLC without any work-up. MS (ESI, m/z): 341.1 (MH+).

Example 26

2-[3-[5-cyclopropyl-4-(cyclopropylmethoxy)pyridin-2-yl]-1,2,4-oxadiazol-5-yl]propan-2-ol

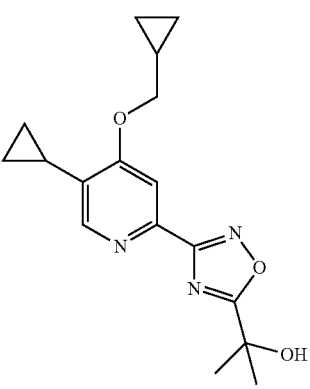 [SMILES: CC(C)(O)c1nc(-c2cc(OCC3CC3)c(C3CC3)cn2)no1]

The title compound was synthesized in analogy to Example 9b, using 2-hydroxy-2-methylpropanoic acid (CAS 594-61-6) and 5-cyclopropyl-4-(cyclopropylmethoxy)-N'-hydroxypicolinimidamide as starting materials, and directly purified by preparative HPLC without any work-up. MS (ESI, m/z): 316.2 (MH+).

Example 27

2-[5-cyclopropyl-4-(2,2,2-trifluoroethoxy)pyridin-2-yl]-4,4-diethyl-5H-1,3-oxazole

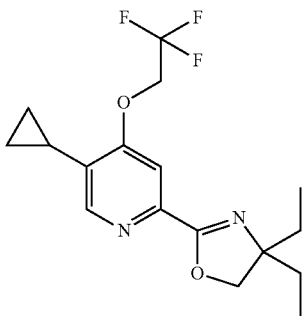 [SMILES: CCC1(CC)COC(c2cc(OCC(F)(F)F)c(C3CC3)cn2)=N1]

The title compound was synthesized in analogy to Example 11, using 5-cyclopropyl-4-(2,2,2-trifluoroethoxy)picolinic acid (previously described as Example 7e) and 2-amino-2-ethylbutan-1-ol (CAS 39884-49-6) as starting materials for the first step. MS (ESI, m/z): 343.2 (MH+).

Example 28

3-[5-cyclopropyl-4-(cyclopropylmethoxy)pyridin-2-yl]-5-(3-methyloxetan-3-yl)-1,2,4-oxadiazole

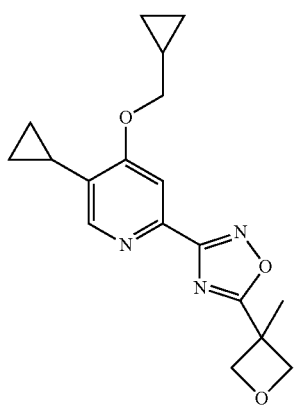 [SMILES: CC1(c2nc(-c3cc(OCC4CC4)c(C4CC4)cn3)no2)COC1]

The title compound was synthesized in analogy to Example 9b, using 3-methyloxetane-3-carboxylic acid (CAS 28562-68-7) and 5-cyclopropyl-4-(cyclopropylmethoxy)-N'-hydroxypicolinimidamide as starting materials, and directly purified by preparative HPLC without any work-up. MS (ESI, m/z): 328.3 (MH+).

Example 29

5-(azetidin-3-yl)-3-[5-cyclopropyl-4-(cyclopropylmethoxy)pyridin-2-yl]-1,2,4-oxadiazole

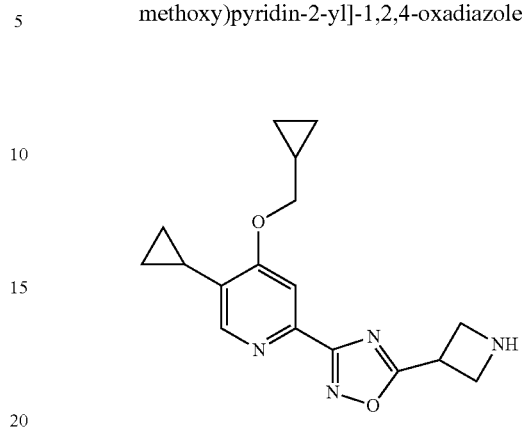

The title compound was synthesized in analogy to Example 9b, using 1-(tert-butoxycarbonyl)azetidine-3-carboxylic acid (CAS 142253-55-2) and 5-cyclopropyl-4-(cyclopropylmethoxy)-N'-hydroxypicolinimidamide as starting materials followed by deprotection of the Boc group by evaporation of the DMF, crude redissolved in TFA. The reaction was stirred at RT for 30 min, volatiles were removed in vacuo and residue was redissolved in ethyl acetate. Organic phase was extracted with aqueous NaOH 1M, dried over $Na_2SO_4$ and evaporated down to dryness. Crude was purified by preparative HPLC. MS (ESI, m/z): 313.1 (MH+).

Example 30

2-[5-(3,3-difluoroazetidin-1-yl)-4-(2,2,2-trifluoroethoxy)pyridin-2-yl]-4,4-diethyl-5H-1,3-oxazole

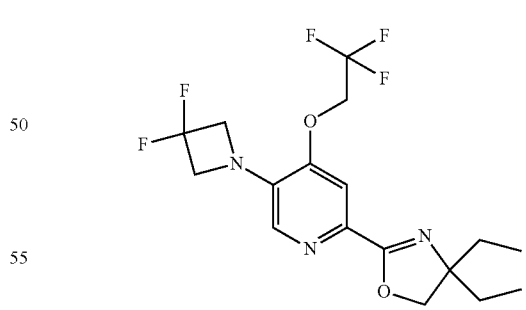

The title compound was synthesized in a similar manner as Example 11, using 5-(3,3-difluoroazetidin-1-yl)-4-(2,2,2-trifluoroethoxy)picolinic acid (previously described as Example 15d) and 2-amino-2-ethylbutan-1-ol (CAS 39884-49-6) as starting materials for the first step. MS (ESI, m/z): 394.0 (MH+).

Example 31

2-[5-cyclopropyl-4-(2,2,2-trifluoroethoxy)pyridin-2-yl]-3-oxa-1-azaspiro[4.5]dec-1-ene

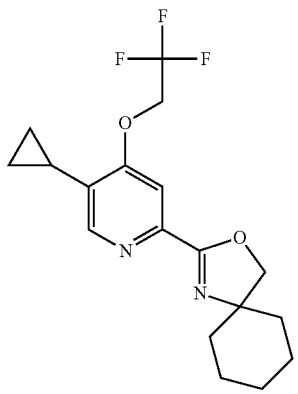 [SMILES: FC(F)(F)COc1cc(C2=NC3(CCCCC3)CO2)ncc1C1CC1]

The title compound was synthesized in analogy to Example 11, using 5-cyclopropyl-4-(2,2,2-trifluoroethoxy)picolinic acid (previously described as Example 7e) and (1-aminocyclohexyl)methanol (CAS 4313-56-8) as starting materials for the first step. MS (ESI, m/z): 355.5 (MH+).

Example 32

5-tert-butyl-3-[4-(cyclopropylmethoxy)-5-(3,3-difluoroazetidin-1-yl)pyridin-2-yl]-1,2,4-oxadiazole a) 3-bromo-4-(cyclopropylmethoxy)pyridine 1-oxide

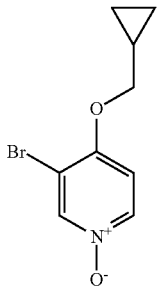

In a 250 mL pear-shaped flask, 3-bromo-4-(cyclopropylmethoxy)pyridine, previously described as Example 1a, (3.7 g, 16.2 mmol, Eq: 1.00) was combined with DCM (81.1 mL) to give a colorless solution. m-CPBA (5.45 g, 24.3 mmol, Eq: 1.5) was added. The reaction mixture was stirred at room temperature for 2 h. The reaction mixture was poured into 250 mL DCM and extracted with 1M NaHCO₃. The organic layers were dried over Na₂SO₄ and concentrated in vacuo. The crude material was purified by flash chromatography (SiO₂, 120 g, gradient MeOH in DCM) giving 3.39 g of the title compound as a white solid (Yield 85%). MS (ESI, m/z): 244.2 (M).

b) 5-bromo-4-(cyclopropylmethoxy)picolinonitrile

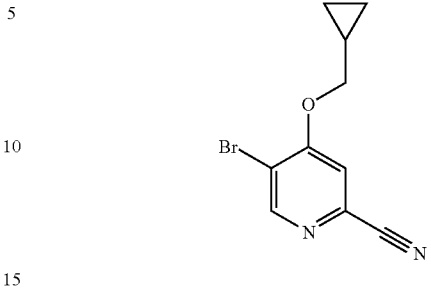

To a solution of 3-bromo-4-(cyclopropylmethoxy)pyridine 1-oxide (9.5 g, 38.9 mmol, Eq: 1.00) in dry DCM (160 mL) cooled down to 0° C. and under argon atmosphere was slowly added TMS-CN (5.79 g, 7.83 mL, 58.4 mmol, Eq: 1.5) followed by addition of dimethylcarbamoyl chloride (6.28 g, 5.37 mL, 58.4 mmol, Eq: 1.5). The reaction mixture was then stirred at RT overnight and monitored by LC-MS which showed complete consumption of the starting material. Addition of aqueous Na₂CO₃ 2M solution and mixture was stirred for 10 min, then poured into a separatory funnel, addition of water and extraction. Organic phase collected, dried over Na₂SO₄ and evaporated down to dryness. Flash chromatography with a 120 g SiO₂ column, eluent mixture of heptane and ethyl acetate giving 3.52 g of the desired isomer (Yield 36%). MS (ESI, m/z): 253.4 (M).

c) 5-bromo-4-(cyclopropylmethoxy)-N'-hydroxypicolinimidamide

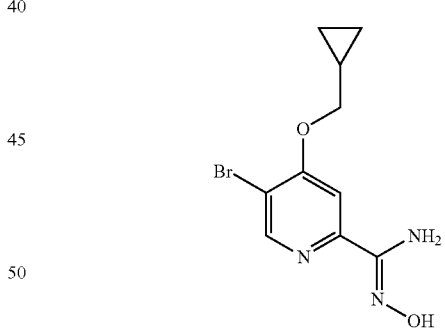

To a solution of 5-bromo-4-(cyclopropylmethoxy)picolinonitrile (0.75 g, 2.96 mmol, Eq: 1.00) in EtOH (8 mL) was added hydroxylamine hydrochloride (309 mg, 4.44 mmol, Eq: 1.5) and triethylamine (450 mg, 620 μL, 4.44 mmol, Eq: 1.5). The reaction mixture was then stirred at 70° C. for 45 min under microwave radiation and reaction monitored by TLC (eluent: ethyl acetate). Reaction mixture was poured into a separatory funnel, diluted with ethyl acetate, extracted with aqueous NaHCO₃ 1M. Organic phase dried over Na₂SO₄ and evaporated down to dryness. Flash chromatography with a 50 g SiO₂ column, eluent mixture of heptane and ethyl acetate giving 482 mg of the desired product (Yield 57%). MS (ESI, m/z): 286.3 (M).

d) 3-(5-bromo-4-(cyclopropylmethoxy)pyridin-2-yl)-5-tert-butyl-1,2,4-oxadiazole

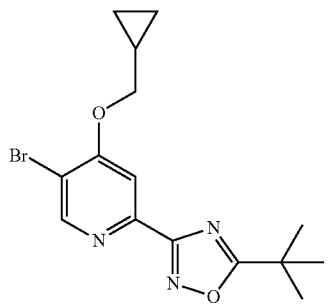 [SMILES: CC(C)(C)c1nc(-c2cc(OCC3CC3)c(Br)cn2)no1]

To a solution of 5-bromo-4-(cyclopropylmethoxy)-N'-hydroxypicolinimidamide (2.1 g, 7.34 mmol, Eq: 1.00) in dry DMF (25 mL) under argon atmosphere at 0° C. was added potassium carbonate (1.12 g, 8.07 mmol, Eq: 1.1) followed by slow addition of pivaloyl chloride (CAS 3282-30-2) (929 mg, 948 μL, 7.71 mmol, Eq: 1.05). The resulting reaction was stirred for 15 min at 0° C. and then stirred for 30 min at RT, reaction was monitored by LC-MS. The reaction was then stirred at 130° C. under microwave radiation for 30 min and controlled by LC-MS which showed complete conversion to the desired product. Removal of DMF in vacuo, residue redissolved in ethyl acetate and solution was poured into a separatory funnel. Extraction with aqueous NaHCO$_3$ 1M, organic phase dried over Na$_2$SO$_4$ and evaporated down to dryness. Flash chromatography with a 70 g SiO$_2$ column, eluent mixture of heptane and ethyl acetate giving 2.4 g of the desired product (Yield 93%). MS (ESI, m/z): 352.4 (M).

e) 5-tert-butyl-3-[4-(cyclopropylmethoxy)-5-(3,3-difluoroazetidin-1-yl)pyridin-2-yl]-1,2,4-oxadiazole

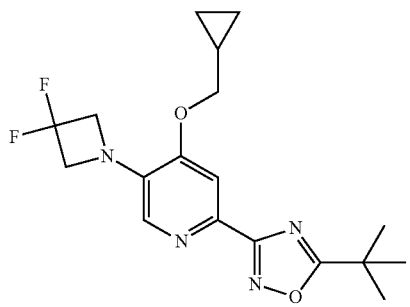 [SMILES: CC(C)(C)c1nc(-c2cc(OCC3CC3)c(N3CC(F)(F)C3)cn2)no1]

To a solution of 3-(5-bromo-4-(cyclopropylmethoxy)pyridin-2-yl)-5-tert-butyl-1,2,4-oxadiazole (0.06 g, 170 μmol, Eq: 1.00) in dry toluene (1 mL) under argon atmosphere was added 3,3-difluoroazetidine hydrochloride (CAS 288315-03-7) (24.3 mg, 187 μmol, Eq: 1.1), Pd(OAc)$_2$ (3.82 mg, 17.0 μmol, Eq: 0.1), BINAP (10.6 mg, 17.0 μmol, Eq: 0.1) and Cs$_2$CO$_3$ (111 mg, 341 μmol, Eq: 2.0). The reaction mixture was stirred at 130° C. for 60 min under microwave radiation and monitored by LC-MS. The reaction mixture was filtered over a pad of Celite, filtrate was evaporated down and dissolved in 1 mL DMSO. Purification was done by preparative HPLC without any prior work-up. MS (ESI, m/z): 365.5 (MH+).

Example 33

5-tert-butyl-3-[5-cyclopropyl-4-(2,2,2-trifluoroethoxy)pyridin-2-yl]-1,2,4-oxadiazole a) 5-cyclopropyl-N'-hydroxy-4-(2,2,2-trifluoroethoxy)picolinimidamide

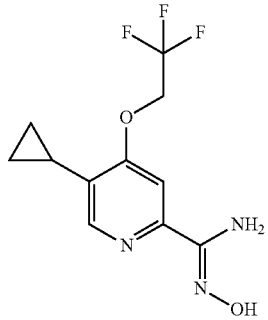 [SMILES: N/C(=N\O)c1cc(OCC(F)(F)F)c(C2CC2)cn1]

To a solution of 5-cyclopropyl-4-(2,2,2-trifluoroethoxy)picolinonitrile, previously described as Example 7d, (1.62 g, 6.69 mmol, Eq: 1.00) in EtOH (13.0 mL) the following was added hydroxylamine hydrochloride (465 mg, 6.69 mmol, Eq: 1.0) and triethylamine (677 mg, 932 μL, 6.69 mmol, Eq: 1.0). The reaction was stirred for 3 h at 70° C. and monitered with LC-MS. Another 0.5 Eq. of Hydroxylamine hydrochloride (232 mg) and triethylamine (465 μL) were added as complete conversion had not taken place. The reaction was stirred for a further 3 h at 70° C. The reaction mixture was poured into a separating funnel, ethyl acetate was added and the mixture was extracted with aqueous NaHCO$_3$ 1M. The organic phase was dried over Na$_2$SO$_4$ and concentrated in vacuo. The crude material was purified by flash chromatography on SiO$_2$, 20 g, gradient ethyl acetate in heptane giving 650 mg of the title compound as a white powder (yield 35%). MS (ESI, m/z): 276.5 (MH+).

b) 5-tert-butyl-3-[5-cyclopropyl-4-(2,2,2-trifluoroethoxy)pyridin-2-yl]-1,2,4-oxadiazole

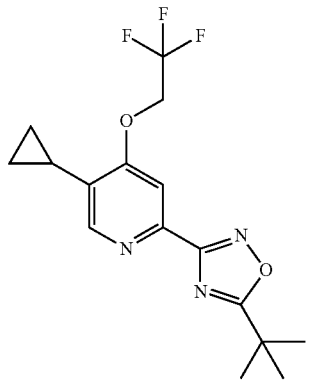 [SMILES: CC(C)(C)c1nc(-c2cc(OCC(F)(F)F)c(C3CC3)cn2)no1]

To a solution of 5-cyclopropyl-N'-hydroxy-4-(2,2,2-trifluoroethoxy)picolinimidamide (0.080 g, 291 μmol, Eq: 1.00) in dry DMF (1.29 mL) under argon atmosphere was added K$_2$CO$_3$ (40.2 mg, 291 μmol, Eq: 1.0) followed by pivaloyl chloride (CAS 3282-30-2) (35.0 mg, 35.8 μL, 291

μmol, Eq: 1.0). The reaction was stirred at RT for 45 min and controlled by LC-MS which showed complete conversion to the intermediate. The reaction mixture was stirred overnight at 120° C. and controlled by LC-MS which showed complete conversion to the desired product. The reaction mixture was diluted with ethyl acetate, poured into a separatory funnel and extracted with water. The organic phase was dried over Na₂SO₄ and evaporated down to dryness. The crude material was purified by flash chromatography (SiO₂, 10 g, gradient ethyl acetate in heptane) giving 55 mg of the title compound as a light yellow waxy solid (Yield 55%). MS (ESI, m/z): 342.5 (MH+).

Example 34

3-[5-cyclopropyl-4-(2,2,2-trifluoroethoxy)pyridin-2-yl]-5-(1-methylcyclopropyl)-1,2,4-oxadiazole

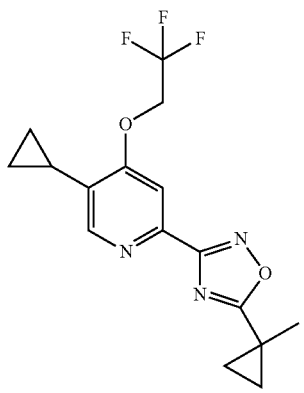 [SMILES: CC1(c2nc(-c3cc(OCC(F)(F)F)c(C4CC4)cn3)no2)CC1]

The title compound was synthesized in analogy to Example 9b, using 1-methylcyclopropanecarboxylic acid (CAS 6914-76-7) and 5-cyclopropyl-N'-hydroxy-4-(2,2,2-trifluoroethoxy)picolinimidamide, described as Example 33a, as starting materials, and directly purified by preparative HPLC without any work-up. MS (ESI, m/z): 340.4 (MH+).

Example 35

1-[6-(5-tert-butyl-1,2,4-oxadiazol-3-yl)-4-(cyclopropylmethoxy)pyridin-3-yl]-6-oxa-1-azaspiro[3.3]heptane

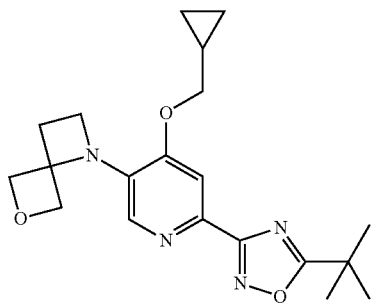 [SMILES: CC(C)(C)c1nc(-c2cc(OCC3CC3)c(N3CCC34COC4)cn2)no1]

The title compound was synthesized in analogy to Example 32e, using 3-(5-bromo-4-(cyclopropylmethoxy) pyridin-2-yl)-5-tert-butyl-1,2,4-oxadiazole and 6-oxa-1-azaspiro[3.3]heptane hemioxalate (CAS 1359655-43-8) as starting materials, and purified by preparative HPLC. MS (ESI, m/z): 371.4 (MH+).

Example 36

3-[5-cyclopropyl-4-(2,2,2-trifluoroethoxy)pyridin-2-yl]-5-propan-2-yl-1,2,4-oxadiazole

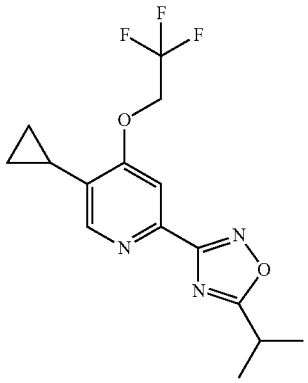 [SMILES: CC(C)c1nc(-c2cc(OCC(F)(F)F)c(C3CC3)cn2)no1]

The title compound was synthesized in analogy to Example 33b, using 5-cyclopropyl-N'-hydroxy-4-(2,2,2-trifluoroethoxy)picolinimidamide and isobutyryl chloride (CAS 79-30-1) as starting materials, and purified by purified by flash chromatography. MS (ESI, m/z): 328.1 (MH+).

Example 37

1-[3-[5-cyclopropyl-4-(2,2,2-trifluoroethoxy)pyridin-2-yl]-1,2,4-oxadiazol-5-yl]cyclopropan-1-ol

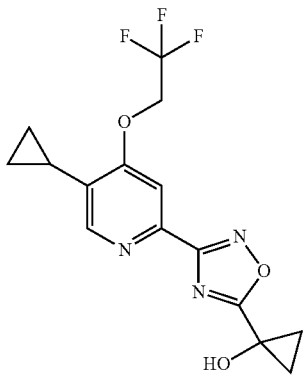 [SMILES: OC1(c2nc(-c3cc(OCC(F)(F)F)c(C4CC4)cn3)no2)CC1]

The title compound was synthesized in analogy to Example 9b, using 1-hydroxycyclopropanecarboxylic acid (CAS 17994-25-1) and 5-cyclopropyl-N'-hydroxy-4-(2,2,2-trifluoroethoxy)picolinimidamide (described as Example 33a) as starting materials, and directly purified by preparative HPLC without any work-up. MS (ESI, m/z): 342.1 (MH+).

Example 38

3-[5-cyclopropyl-4-(2,2,2-trifluoroethoxy)pyridin-2-yl]-5-(3-methyloxetan-3-yl)-1,2,4-oxadiazole

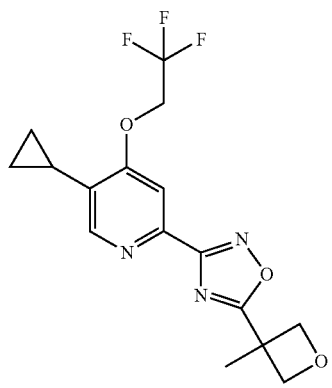 [SMILES: CC1(c2nc(-c3cc(OCC(F)(F)F)c(C4CC4)cn3)no2)COC1]

The title compound was synthesized in analogy to Example 9b, using 3-methyloxetane-3-carboxylic acid (CAS 28562-68-7) and 5-cyclopropyl-N'-hydroxy-4-(2,2,2-trifluoroethoxy)picolinimidamide (described as Example 33a) as starting materials, and purified by purified by flash chromatography. MS (ESI, m/z): 356.5 (MH+).

Example 39

3-[5-cyclopropyl-4-(2,2,2-trifluoroethoxy)pyridin-2-yl]-1,2,4-oxadiazole

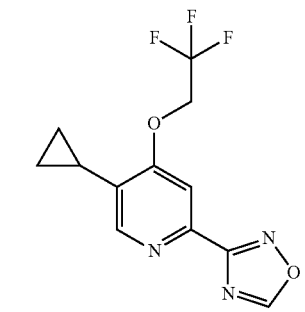 [SMILES: FC(F)(F)COc1cc(-c2ncon2)ncc1C1CC1]

5-cyclopropyl-N'-hydroxy-4-(2,2,2-trifluoroethoxy)picolinimidamide, described as Example 33a, (60 mg, 218 μmol, Eq: 1.00) was combined with DCM (2.6 mL) and treated with triethyl orthoformate (129 mg, 145 μL, 872 μmol, Eq: 4.0) under Nitrogen. The resulting solution was then treated with boron trifluoride etherate (3.09 mg, 2.76 μL, 21.8 μmol, Eq: 0.1) and allowed to stire for 2 h at RT. 0.5 more equivalents of triethyl orthoformate (16.1 mg) and 0.1 equivalents of boron triflouride etherate (0.773 mg) were added and the mixture left to stir overnight. The mixture was brought up to a basic pH with NaHCO₃ and extracted with DCM. The aqueous layer was then extracted with ethyl acetate two times. The organic layers were combined, dried and concentrated in vacuo. The crude material was purified by flash chromatography (SiO₂, 10 g, gradient ethyl acetate in heptane) giving 48 mg of the title compound as a white solid (Yield 77%). MS (ESI, m/z): 286.4 (MH+).

Example 40

3-tert-butyl-5-[5-cyclopropyl-4-(2,2,2-trifluoroethoxy)pyridin-2-yl]-1,2,4-oxadiazole

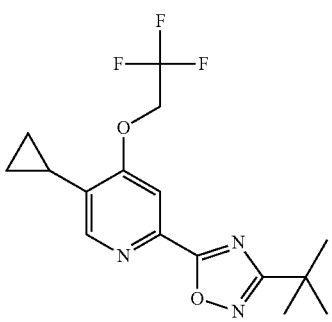 [SMILES: CC(C)(C)c1noc(-c2cc(OCC(F)(F)F)c(C3CC3)cn2)n1]

The title compound was synthesized in analogy to Example 7f, using 5-cyclopropyl-4-(2,2,2-trifluoroethoxy) picolinic acid and N'-hydroxypivalimidamide (CAS 42956-75-2) as starting materials, and directly purified by preparative HPLC without any work-up. MS (ESI, m/z): 342.5 (MH+).

Example 41

2-[5-cyclopropyl-4-(2,2,2-trifluoroethoxy)pyridin-2-yl]-5,5-dimethyl-4H-1,3-oxazole

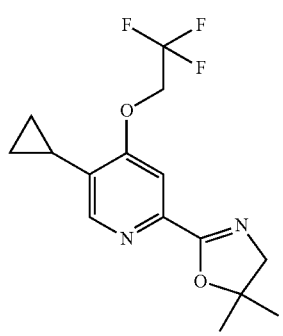 [SMILES: CC1(C)CN=C(c2cc(OCC(F)(F)F)c(C3CC3)cn2)O1]

The title compound was synthesized in a similar manner as Example 11, using 5-cyclopropyl-4-(2,2,2-trifluoroethoxy)picolinic acid (previously described as Example 7e) and 1-amino-2-methylpropan-2-ol (CAS 2854-16-2) as starting materials for the first step. The second step differs as follow: To a solution of 5-cyclopropyl-N-(2-hydroxy-2-methylpropyl)-4-(2,2,2-trifluoroethoxy)picolinamide (60 mg, 0.181 mmol, Eq: 1.00) in DCM (900 μL) was added methanesulfonic acid (59 μL, 0.9 mmol, Eq: 5.0). Reaction was heated at 40° C. 2 h. LC-MS showed reaction was complete. Extraction with DCM/NaHCO₃ saturated aqueous solution Organic layer was dried on MgSO₄ and evaporated. Column on SiO₂ with a gradient heptane/ethyl acetate. MS (ESI, m/z): 315.5 (MH⁺) to give 5.9 mg of the title compound as colorless viscous oil.

Example 42

5-[5-cyclopropyl-4-(2,2,2-trifluoroethoxy)pyridin-2-yl]-3-propan-2-yl-1,2,4-oxadiazole

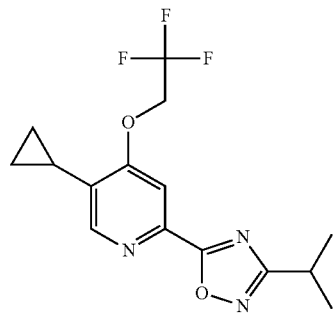 [SMILES: CC(C)c1noc(-c2cc(OCC(F)(F)F)c(C3CC3)cn2)n1]

The title compound was synthesized in analogy to Example 7f, using 5-cyclopropyl-4-(2,2,2-trifluoroethoxy)picolinic acid and N'-hydroxyisobutyrimidamide (CAS 35613-84-4) as starting materials, and directly purified by preparative HPLC without any work-up. MS (ESI, m/z): 328.4 (MH+).

Example 43

5-tert-butyl-3-[4-(cyclopropylmethoxy)-5-methylsulfonylpyridin-2-yl]-1,2,4-oxadiazole a) 5-tert-butyl-3-(4-(cyclopropylmethoxy)-5-(methylthio)pyridin-2-yl)-1,2,4-oxadiazole

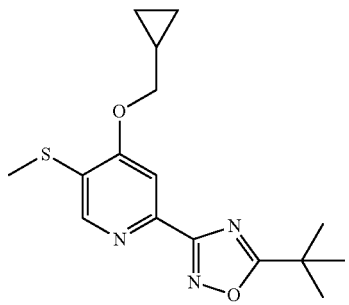 [SMILES: CSc1cnc(-c2noc(C(C)(C)C)n2)cc1OCC1CC1]

To a solution of 3-(5-bromo-4-(cyclopropylmethoxy)pyridin-2-yl)-5-tert-butyl-1,2,4-oxadiazole, previously described as Example 32d, (0.08 g, 227 µmol, Eq: 1.00) in dry DMF (1.5 mL) under argon atmosphere was added methanethiol, sodium salt (CAS 5188-07-8) (19.4 mg, 273 µmol, Eq: 1.2) and the resulting reaction mixture was stirred at 100° C. overnight and controlled by TLC. Reaction mixture poured into a separatory funnel, dilution with ethylcetate, extraction with aqueous NaHCO₃ 1M. The aqueous phase was back-extracted with ethyl acetate, organic phase combined, dried over Na₂SO₄ and evaporated down to dryness. Flash chromatography with a 10 g SiO₂ column, eluent mixture of heptane and ethyl acetate gave 49 mg of the desired product (Yield 67%). MS (ESI, m/z): 319.9 (MH+).

b) 5-tert-butyl-3-[4-(cyclopropylmethoxy)-5-methylsulfonylpyridin-2-yl]-1,2,4-oxadiazole

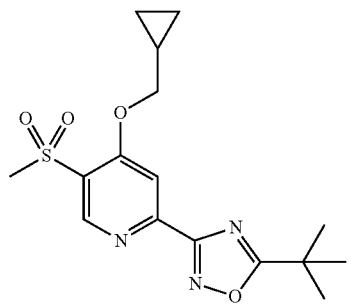 [SMILES: CC(C)(C)c1nc(-c2cc(OCC3CC3)c(S(C)(=O)=O)cn2)no1]

To a solution of 5-tert-butyl-3-(4-(cyclopropylmethoxy)-5-(methylthio)pyridin-2-yl)-1,2,4-oxadiazole (0.045 g, 141 µmol, Eq: 1.00) in DCM (1 mL) was added m-CPBA (63.1 mg, 282 µmol, Eq: 2.0). The reaction mixture was stirred at RT overnight and controlled by LC-MS. Only partial conversion to the sulfone and no more starting material but major product is the sulfoxide. Addition of m-CPBA (12.2 mg, 70.4 µmol, Eq: 0.5) to the reaction mixture was stirred at RT for 2 h, control by LC-MS showed change in conversion but not total. The reaction was stopped anyway. Evaporation of the volatiles and residue was redissolved in DMSO for purification by preparative HPLC without any work-up giving 18.3 mg of the desired product (Yield 37%). MS (ESI, m/z): 352.5 (MH+).

Example 44

5-tert-butyl-3-[5-(3,3-difluoroazetidin-1-yl)-4-(2,2,2-trifluoroethoxy)pyridin-2-yl]-1,2,4-oxadiazole a) 5-(3,3-difluoroazetidin-1-yl)-N'-hydroxy-4-(2,2,2-trifluoroethoxy)picolinimidamide

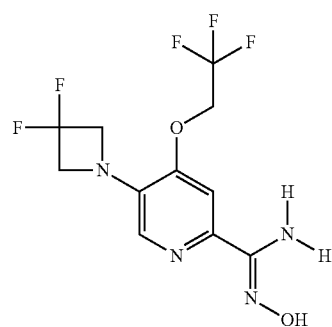 [SMILES: N/C(=N\O)c1cc(OCC(F)(F)F)c(N2CC(F)(F)C2)cn1]

To a solution of 5-(3,3-difluoroazetidin-1-yl)-4-(2,2,2-trifluoroethoxy)picolinonitrile, previously described as Example 15c, (1 g, 3.41 mmol, Eq: 1.00) in EtOH (16.6 mL) was added hydroxylamine hydrochloride (261 mg, 156 µL, 3.75 mmol, Eq: 1.1) and triethylamine (380 mg, 524 µL, 3.75 mmol, Eq: 1.1). The reaction mixture was heated up to 70° C. and left for half an hour. LC-MS showed the reaction was complete. The reaction mixture was poured into a separatory funnel, ethyl acetate was added and the mixture was extracted with aqueous saturated NaHCO₃ 1M. The organic phase was dried over Na₂SO₄ and evaporated down to dryness to give 1.09 g of the desired compound as a white powder (yield 98%). MS (ESI, m/z): 327.2 (MH+).

b) 5-tert-butyl-3-[5-(3,3-difluoroazetidin-1-yl)-4-(2,2,2-trifluoroethoxy)pyridin-2-yl]-1,2,4-oxadiazole

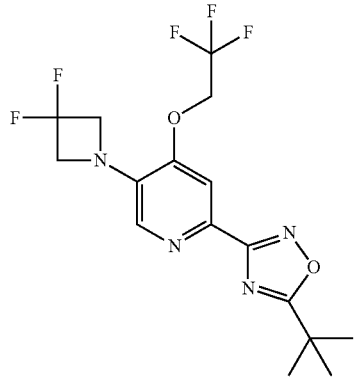 [SMILES: CC(C)(C)c1nc(-c2cc(OCC(F)(F)F)c(N3CC(F)(F)C3)cn2)no1]

To a solution of 5-(3,3-difluoroazetidin-1-yl)-N'-hydroxy-4-(2,2,2-trifluoroethoxy)picolinimidamide (0.08 g, 245 µmol, Eq: 1.00) in dry DMF (1.09 mL) under argon atmosphere was added K₂CO₃ (37.3 mg, 270 µmol, Eq: 1.1) followed by pivaloyl chloride (CAS 3282-30-2) (32.5 mg, 33.2 µL, 270 µmol, Eq: 1.1). The reaction was stirred at RT for 45 min and controlled by LC-MS which showed complete conversion to the intermediate. The reaction mixture was stirred overnight at 120° C. and controlled by LC-MS which showed complete conversion to the desired product. The reaction mixture was diluted with ethyl acetate, poured into a separatory funnel and extracted with water. The organic phase was dried over Na₂SO₄ and evaporated down to dryness. The crude material was purified by flash chromatography (SiO₂, gradient ethyl acetate in heptane) giving 44 mg of the title compound as a white powder (Yield 45%). MS (ESI, m/z): 393.1 (MH+).

Example 45

3-[5-(3,3-difluoroazetidin-1-yl)-4-(2,2,2-trifluoroethoxy)pyridin-2-yl]-5-propan-2-yl-1,2,4-oxadiazole

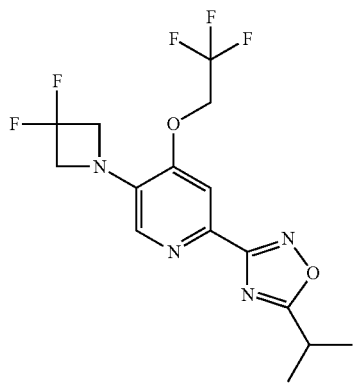 [SMILES: CC(C)c1nc(-c2cc(OCC(F)(F)F)c(N3CC(F)(F)C3)cn2)no1]

The title compound was synthesized in analogy to Example 44b, using 5-(3,3-difluoroazetidin-1-yl)-N'-hydroxy-4-(2,2,2-trifluoroethoxy)picolinimidamide and isobutyryl chloride (CAS 79-30-1) as starting materials, and purified by purified by flash chromatography. MS (ESI, m/z): 379.1 (MH+).

Example 46

1-[3-[5-(3,3-difluoroazetidin-1-yl)-4-(2,2,2-trifluoroethoxy)pyridin-2-yl]-1,2,4-oxadiazol-5-yl]cyclopropan-1-ol

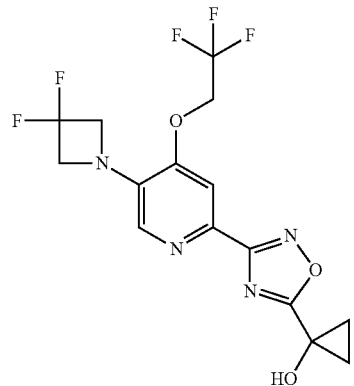 [SMILES: OC1(c2nc(-c3cc(OCC(F)(F)F)c(N4CC(F)(F)C4)cn3)no2)CC1]

To a solution of 1-hydroxycyclopropanecarboxylic acid (CAS 17994-25-1) (27.5 mg, 270 µmol, Eq: 1.1) in DMF (1.44 mL) was added CDI (43.7 mg, 270 µmol, Eq: 1.1) and the resulting reaction mixture was stirred at RT for 45 min, followed by the addition of 5-(3,3-difluoroazetidin-1-yl)-N'-hydroxy-4-(2,2,2-trifluoroethoxy)picolinimidamide, previously described as Example 44a, (80 mg, 245 µmol, Eq: 1.00). The reaction was then stirred at RT for 2 h and monitored by LC-MS which showed complete consumption of the starting material to form the intermediate. The reaction mixture was then heated to 130° C. and left to stir overnight. The reaction was diluted with ethyl acetate and extracted with water. The organic layers were dried over Na₂SO₄ and concentrated in vacuo. The crude material was purified by flash chromatography (SiO₂, 10 g, gradient ethyl acetate in heptane) giving 41.7 mg of the title compound as a white powder (Yield 43%). MS (ESI, m/z): 393.4 (MH+).

Example 47

3-[5-(3,3-difluoroazetidin-1-yl)-4-(2,2,2-trifluoroethoxy)pyridin-2-yl]-5-(3-methyloxetan-3-yl)-1,2,4-oxadiazole

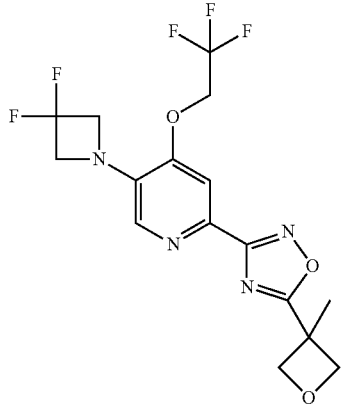 [SMILES: CC1(c2nc(-c3cc(OCC(F)(F)F)c(N4CC(F)(F)C4)cn3)no2)COC1]

The title compound was synthesized in analogy to Example 46, using 3-methyloxetane-3-carboxylic acid (CAS 28562-68-7) and 5-(3,3-difluoroazetidin-1-yl)-N'-hydroxy-4-(2,2,2-trifluoroethoxy)picolinimidamide as starting materials, and purified by purified by flash chromatography. MS (ESI, m/z): 407.5 (MH+).

Example 48

5-tert-butyl-3-[5-cyclopropyl-4-[(2S)-1,1,1-trifluoropropan-2-yl]oxypyridin-2-yl]-1,2,4-oxadiazole a) 2,4-dichloro-5-cyclopropylpyridine

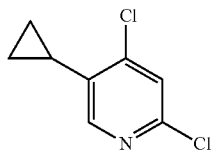 [SMILES: Clc1cc(Cl)c(C2CC2)cn1]

To a solution of 5-bromo-2,4-dichloropyridine (CAS 849937-96-8) (22.95 g, 96.1 mmol, Eq: 1.00) in Toluene (352 mL) and Water (48.0 mL) was added Pd(OAc)₂ (431 mg, 1.92 mmol, Eq: 0.02), butyldi-1-adamantylphosphine (1.03 g, 2.88 mmol, Eq: 0.03), potassium cyclopropyltrifluoroborate (CAS 1065010-87-8) (14.9 g, 101 mmol, Eq: 1.05) and Cs₂CO₃ (62.6 g, 192 mmol, Eq: 2.0). The resulting reaction mixture was stirred at 110° C. overnight and controlled by TLC. The reaction was found to be only partially complete so 0.5 more equivalents (7.5 g) of potassium cyclopropyltrifluororate were added (3 times). Reaction mixture concentrated in vacuo then diluted with ethyl acetate and the solution poured into a separatory funnel. Extraction with aqueous saturated NaHCO₃, organic phase dried over NaSO₄ and evaporated down to dryness. Flash chromatography with a 330 g SiO₂ column, eluent mixture of heptane and ethyl acetate giving 7.39 g of the desired product (Yield 40%). MS (ESI, m/z): 188.2 (M).

b) 4-chloro-5-cyclopropylpicolinonitrile

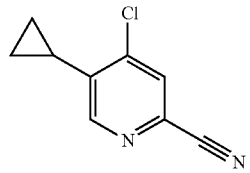 [SMILES: N#Cc1cc(Cl)c(C2CC2)cn1]

To a solution of 2,4-dichloro-5-cyclopropylpyridine (7.35 g, 39.1 mmol, Eq: 1.00) dissolved in dry DMF (130 mL), dppf (1.73 g, 3.13 mmol, Eq: 0.08) was added followed by dicyanozinc (2.75 g, 23.5 mmol, Eq: 0.6) and Pd₂dba₃ (1.95 mmol, Eq: 0.05). Reaction was stirred at 100° C. for 2 h, controlled by TLC. Reaction mixture filtered on a pad of Celite, filtrate diluted with ethyl acetate, extraction with water, aqueous phase back-extracted with ethyl acetate, organic phase dried over Na₂SO₄ and concentrated in vacuo. Purification with a 330 g SiO₂ column, eluent mixture of Heptane and EtOAc giving 6.82 g of the title compound as a yellow solid (Yield 97%). MS (ESI, m/z): 179.2 (MH+).

c) 4-chloro-5-cyclopropyl-N'-hydroxypicolinimidamide

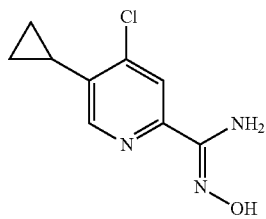 [SMILES: N/C(=N\O)c1cc(Cl)c(C2CC2)cn1]

To a solution of 4-chloro-5-cyclopropylpicolinonitrile (3.2 g, 17.9 mmol, Eq: 1.00) in EtOH (120 mL) was added hydroxylamine hydrochloride (1.87 g, 26.9 mmol, Eq: 1.5) and triethylamine (5 mL, 35.8 mmol, Eq: 2.0). The reaction was heated at 90° C. and monitered with LC-MS. The reaction mixture was poured into a separating funnel, diluted with DCM and the mixture extracted with aqueous NaHCO₃ saturated solution. The organic phase was dried over Na₂SO₄ and concentrated in vacuo to give a white crystalline solid (Yield 96%). MS (ESI, m/z): 212.5 (MH+).

d) 5-tert-butyl-3-(4-chloro-5-cyclopropylpyridin-2-yl)-1,2,4-oxadiazole

To a solution of 4-chloro-5-cyclopropyl-N'-hydroxypicolinimidamide (3.64 g, 17.2 mmol, Eq: 1.00) in dry DMF (115 mL) was added pivaloyl chloride (CAS 3282-30-2) (2.7 g, 2.75 mL, 22.4 mmol, Eq: 1.3) and triethylamine (4.79 mL, 34.4 mmol, Eq: 2.0). The reaction was stirred at RT 30 min. LC-MS showed formation of the intermediate. Reaction mixture was then heated at 110° C. overnight. Solvent was partially evaporated the crude extracted with ethyl acetate and NaHCO₃ aqueous saturated solution. Organic layer was dried on Na₂SO₄ and evaporated. Column on SiO₂ column using MPLC ISCO with a gradient ethyl acetate in heptane gave the title product as yellow viscous oil (Yield 77%). MS (ESI, m/z): 278.6 (MH+).

e) 5-tert-butyl-3-[5-cyclopropyl-4-[(2S)-1,1,1-trifluoropropan-2-yl]oxypyridin-2-yl]-1,2,4-oxadiazole

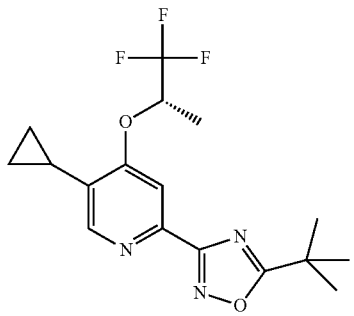 [SMILES: C[C@H](Oc1cc(-c2noc(C(C)(C)C)n2)ncc1C1CC1)C(F)(F)F]

To a solution of 5-tert-butyl-3-(4-chloro-5-cyclopropylpyridin-2-yl)-1,2,4-oxadiazole (0.05 g, 180 μmol, Eq: 1.00) in dry DMF (1.5 mL) was added (S)-1,1,1-trifluoropropan-2-ol (CAS 3539-97-7) (30.8 mg, 270 μmol, Eq: 1.5) followed by NaH (10.8 mg, 270 μmol, Eq: 1.5). The reaction mixture was stirred at RT for 15 min, then stirred under microwave radiation for 30 min at 100° C. and monitored by LC-MS. The reaction mixture was quenched with water and directly purified by preparative HPLC without any work-up giving 44.2 mg of the desired product (Yield 69%). MS (ESI, m/z): 356.5 (MH+).

Example 49

5-tert-butyl-3-[5-cyclopropyl-4-[(2R)-1,1,1-trifluoropropan-2-yl]oxypyridin-2-yl]-1,2,4-oxadiazole

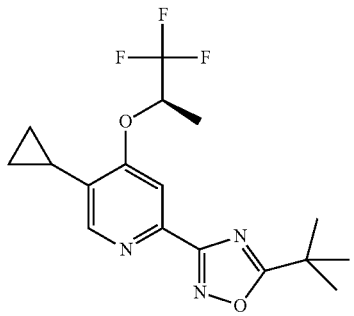 [SMILES: C[C@@H](Oc1cc(-c2noc(C(C)(C)C)n2)ncc1C1CC1)C(F)(F)F]

The title compound was synthesized in analogy to Example 48e, using 5-tert-butyl-3-(4-chloro-5-cyclopropylpyridin-2-yl)-1,2,4-oxadiazole and (R)-1,1,1-trifluoropropan-2-ol (75% in TBME) (CAS 17628-73-8) as starting materials, and purified by preparative HPLC without any work-up. MS (ESI, m/z): 356.5 (MH+).

Example 50

3-[5-(3,3-difluoroazetidin-1-yl)-4-(2,2,2-trifluoroethoxy)pyridin-2-yl]-5-(1-methylcyclopropyl)-1,2,4-oxadiazole

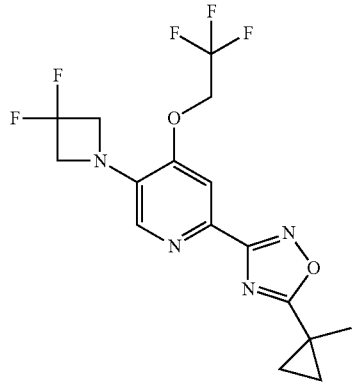 [SMILES: CC1(c2nc(-c3cc(OCC(F)(F)F)c(N4CC(F)(F)C4)cn3)no2)CC1]

The title compound was synthesized in analogy to Example 46, using 1-methylcyclopropanecarboxylic acid (CAS 6914-76-7) and 5-(3,3-difluoroazetidin-1-yl)-N'-hydroxy-4-(2,2,2-trifluoroethoxy)picolinimidamide as starting materials, and purified by purified by flash chromatography. MS (ESI, m/z): 391.1 (MH+).

Example 51

3-tert-butyl-5-[5-cyclopropyl-4-[(2R)-1,1,1-trifluoropropan-2-yl]oxypyridin-2-yl]-1,2,4-oxadiazole a) 4-chloro-3-cyclopropylpyridine

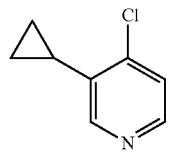

To a solution of 3-bromo-4-chloropyridine (7.1 g, 36.9 mmol, Eq: 1.00) in toluene/water (153 mL/18 mL) was added Potassium Cyclopropyltrifluoroborate (CAS 1065010-87-8) (8.41 g, 38.7 mmol, Eq: 1.05), palladium (II) acetate (331 mg, 1.48 mmol, Eq: 0.04), cesium carbonate (30.1 g, 92.2 mmol, Eq: 2.5) and Butyldi-1-Adamantylphosphine (661 mg, 1.84 mmol, Eq: 0.05). Reaction was stirred at 115° C. overnight under argon. LC-MS showed product. Extraction with water/ethyl acetate (3 times). Organic layer was dried on MgSO₄ and evaporated. Column on SiO₂ with a gradient heptane/ethyl acetate gave 3.8 g of the desired compound as a yellow oil (Yield 67%). MS (ESI, m/z): 154.0 (MH+).

b) 4-Chloro-5-cyclopropyl-pyridine-2-carboxylic acid

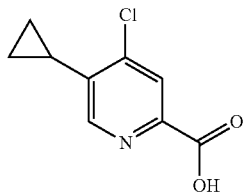 [SMILES: O=C(O)c1cc(Cl)c(C2CC2)cn1]

To a solution of N,N-Dimethylethanolamine (2.18 g, 2.46 mL, 24.4 mmol, Eq: 2.5) in Hexane at −15° C. under argon was slowly added BuLi 1.6M in Hexane (30.5 mL, 48.8 mmol, Eq: 5.0). The reaction was stirred at −15° C. during 20 min. The reaction was cooled down to −78° C. before addition of 4-chloro-3-cyclopropylpyridine (1.5 g, 9.77 mmol, Eq: 1.0). Reaction was stirred 1 h at −78° C. before pellets of dry ice addition. The reaction was slowly allowed to reach −20° C. LC-MS confirmed product formation. Reaction was quenched with water and stirred 5 min. Extraction with HCl 4M aqueous solution and ethyl acetate (3 times). Organic layer was dried on MgSO$_4$ and evaporated to give yellow oil. Diethyl ether was poured on the crude, giving a white suspension, and placed in the fridge. Filtration and washed with ether. Mother liquor was concentrated and again ether was added. Precipitate was filtered and dried under high vacuum giving 850 mg of title compound as white powder (Yield 44%). MS (ESI, m/z): 196.0 (MH−).

c) 3-tert-butyl-5-(4-chloro-5-cyclopropylpyridin-2-yl)-1,2,4-oxadiazole

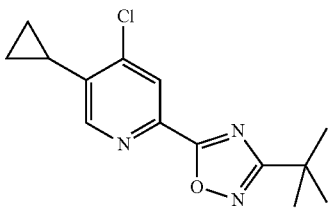 [SMILES: CC(C)(C)c1noc(-c2cc(Cl)c(C3CC3)cn2)n1]

To a solution of 4-chloro-5-cyclopropylpicolinic acid (300 mg, 1.52 mmol, Eq: 1.00) in dry DMF (6 mL) was added CDI (369 mg, 2.28 mmol, Eq: 1.5) and reaction stirred for 30 min at RT. N'-hydroxypivalimidamide (CAS 42956-75-2) (265 mg, 2.28 mmol, Eq: 1.5) was then added, stirred for 1 h at RT and heated to 100° C. over night. The reaction mixture was controlled by LC-MS. The reaction mixture was concentrated and the residue was dissolved in ethyl acetate. The extraction was accomplished with 1M NaHCO$_3$, dried over Na$_2$SO$_4$ and concentrated. The crude material was purified by flash chromatography (SiO$_2$, 10 g, eluent: heptane/ethyl acetate) giving 100 mg of the title compound as light yellow liquid (Yield 23%). MS (ESI, m/z): 278.4 (MH+).

d) 3-tert-butyl-5-[5-cyclopropyl-4-[(2R)-1,1,1-trifluoropropan-2-yl]oxypyridin-2-yl]-1,2,4-oxadiazole

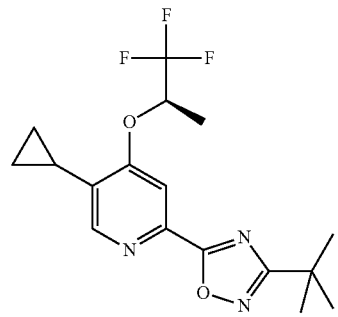 [SMILES: C[C@@H](Oc1cc(-c2nc(C(C)(C)C)no2)ncc1C1CC1)C(F)(F)F]

To a solution of 3-tert-butyl-5-(4-chloro-5-cyclopropylpyridin-2-yl)-1,2,4-oxadiazole (48 mg, 173 μmol, Eq: 1.00) in dry DMF (100 mL) were added (R)-1,1,1-trifluoropropan-2-ol (84.5 mg, 518 μmol, Eq: 3.0) (CAS 17628-73-8) and NaH (20.7 mg, 518 μmol, Eq: 3.0) and reaction stirred at RT for 30 min. The reaction mixture was then heated to 100° C. for 30 min in the microwave. The reaction was directly purified by preparative HPLC without any work-up giving the title compound as a white solid. MS (ESI, m/z): 356.3 (MH+).

Example 52

3-tert-butyl-5-[5-cyclopropyl-4-[(2S)-1,1,1-trifluoropropan-2-yl]oxypyridin-2-yl]-1,2,4-oxadiazole

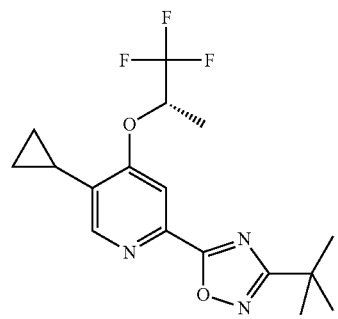 [SMILES: C[C@H](Oc1cc(-c2nc(C(C)(C)C)no2)ncc1C1CC1)C(F)(F)F]

The title compound was synthesized in analogy to Example 51d, using 3-tert-butyl-5-(4-chloro-5-cyclopropylpyridin-2-yl)-1,2,4-oxadiazole and (S)-1,1,1-trifluoropropan-2-ol (CAS 3539-97-7) as starting materials, and purified by preparative HPLC without any work-up. MS (ESI, m/z): 356.4 (MH+).

Example 53

5-tert-butyl-3-[5-cyclopropyl-4-[(4-fluorophenyl)methoxy]pyridin-2-yl]-1,2,4-oxadiazole

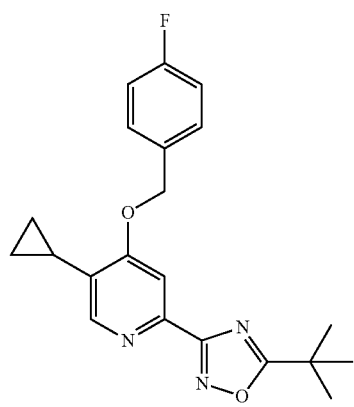 [SMILES: CC(C)(C)c1nc(-c2cc(OCc3ccc(F)cc3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and (4-fluorophenyl)methanol (CAS 459-56-3) as starting materials, and purified by preparative HPLC without any work-up. MS (ESI, m/z): 368.6 (MH+).

Example 54

5-tert-butyl-3-[5-cyclopropyl-4-(oxetan-3-yloxy)pyridin-2-yl]-1,2,4-oxadiazole

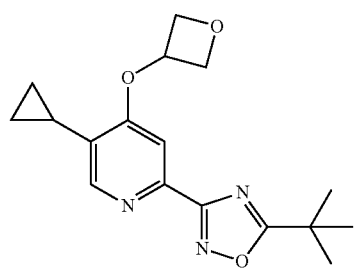 [SMILES: CC(C)(C)c1nc(-c2cc(OC3COC3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and oxetan-3-ol (CAS 7748-36-9) as starting materials, and purified by preparative HPLC without any work-up. MS (ESI, m/z): 316.5 (MH+).

Example 55

5-tert-butyl-3-[5-cyclopropyl-4-[(3-methyloxetan-3-yl)methoxy]pyridin-2-yl]-1,2,4-oxadiazole

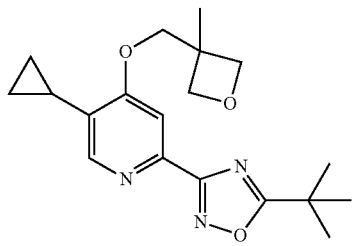 [SMILES: CC1(COc2cc(-c3noc(C(C)(C)C)n3)ncc2C2CC2)COC1]

The title compound was synthesized in analogy to Example 48e, using 5-tert-butyl-3-(4-chloro-5-cyclopropylpyridin-2-yl)-1,2,4-oxadiazole and (3-methyloxetan-3-yl)methanol (CAS 3143-02-0) as starting materials, and purified by preparative HPLC without any work-up. MS (ESI, m/z): 344.5 (MH+).

Example 56

5-tert-butyl-3-[5-cyclopropyl-4-(oxolan-2-ylmethoxy)pyridin-2-yl]-1,2,4-oxadiazole

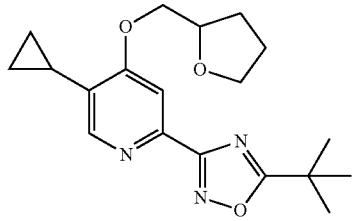 [SMILES: CC(C)(C)c1nc(-c2cc(OCC3CCCO3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and (tetrahydrofuran-2-yl)methanol (CAS 97-99-4) as starting materials, and purified by preparative HPLC without any work-up. MS (ESI, m/z): 344.6 (MH+).

Example 57

5-tert-butyl-3-[5-cyclopropyl-4-[[(2S)-1-methylpyrrolidin-2-yl]methoxy]pyridin-2-yl]-1,2,4-oxadiazole

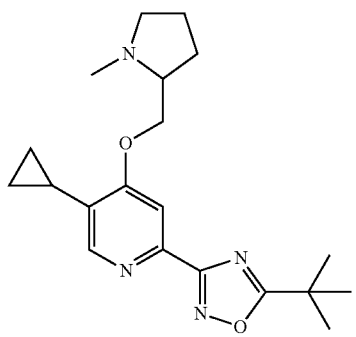 [SMILES: CN1CCCC1COc1cc(-c2noc(C(C)(C)C)n2)ncc1C1CC1]

The title compound was synthesized in analogy to Example 48e, using 5-tert-butyl-3-(4-chloro-5-cyclopropylpyridin-2-yl)-1,2,4-oxadiazole and (S)-(1-methylpyrrolidin-2-yl)methanol (CAS 34381-71-0) as starting materials, and purified by preparative HPLC without any work-up. MS (ESI, m/z): 357.2 (MH+).

Example 58

5-tert-butyl-3-[5-cyclopropyl-4-(oxetan-2-ylmethoxy)pyridin-2-yl]-1,2,4-oxadiazole

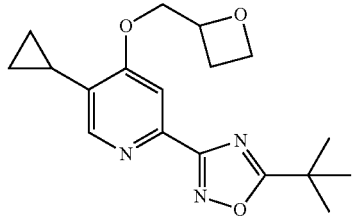 [SMILES: CC(C)(C)c1nc(-c2cc(OCC3CCO3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and oxetan-2-ylmethanol (CAS 61266-70-4) as starting materials, and purified by preparative HPLC without any work-up. MS (ESI, m/z): 330.5 (MH+).

Example 59

5-tert-butyl-3-[5-cyclopropyl-4-(1-methylpyrrolidin-3-yl)oxypyridin-2-yl]-1,2,4-oxadiazole

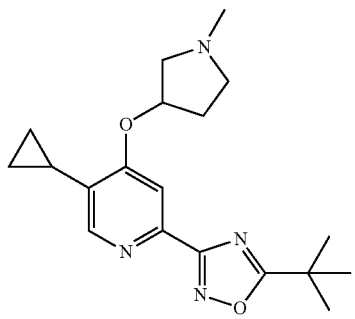 [SMILES: CN1CCC(Oc2cc(-c3noc(C(C)(C)C)n3)ncc2C2CC2)C1]

The title compound was synthesized in analogy to Example 48e, using 5-tert-butyl-3-(4-chloro-5-cyclopropylpyridin-2-yl)-1,2,4-oxadiazole and 1-methylpyrrolidin-3-ol (CAS 13220-33-2) as starting materials, and purified by preparative HPLC without any work-up. MS (ESI, 111/Z): 343.5 (MH+).

Example 60

3-[3-[5-cyclopropyl-4-(cyclopropylmethoxy)pyridin-2-yl]-1,2,4-oxadiazol-5-yl]oxetan-3-amine a) N-(3-(3-(5-cyclopropyl-4-(cyclopropylmethoxy)pyridin-2-yl)-1,2,4-oxadiazol-5-yl)oxetan-3-yl)-2,2,2-trifluoroacetamide

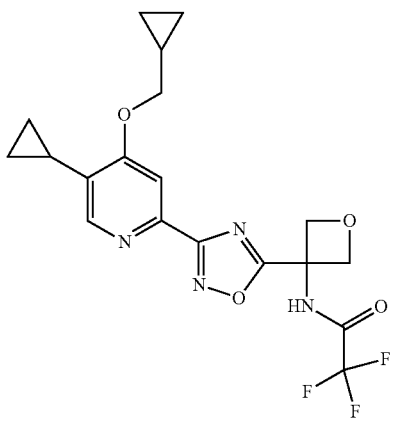 [SMILES: O=C(NC1(c2nc(-c3cc(OCC4CC4)c(C4CC4)cn3)no2)COC1)C(F)(F)F]

The title compound was synthesized in analogy to Example 9b, using 3-(2,2,2-trifluoroacetamido)oxetane-3-carboxylic acid (CAS 1392072-19-3) and 5-cyclopropyl-4-(cyclopropylmethoxy)-N'-hydroxypicolinimidamide as starting materials. DMF was evaporated, residue redissolved in ethyl acetate and poured into a separatory funnel, extraction with aqueous NaHCO₃ 1M, organic phase dried over Na₂SO₄ and evaporated down to dryness. Flash chromatography with SiO₂ column, eluent mixture of heptane and ethyl acetate. MS (ESI, m/z): 425.2 (MH+).

b) 3-[3-[5-cyclopropyl-4-(cyclopropylmethoxy)pyridin-2-yl]-1,2,4-oxadiazol-5-yl]oxetan-3-amine

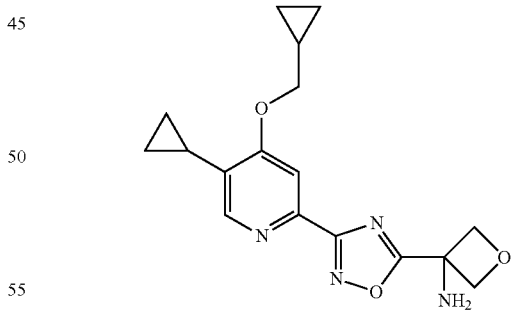

To a solution of N-(3-(3-(5-cyclopropyl-4-(cyclopropylmethoxy)pyridin-2-yl)-1,2,4-oxadiazol-5-yl)oxetan-3-yl)-2,2,2-trifluoroacetamide (0.06 g, 141 µmol, Eq: 1.00) in ammonia 7N in MeOH (1.01 mL, 7.07 mmol, Eq: 50.0) was stirred at 100° C. for 30 min under microwave radiation and reaction was monitored by LC-MS. When the reaction was completed, volatiles were removed in vacuo and the residue was resdissolved in DMF. Purification was done by preparative HPLC without any work-up procedure and gave 9 mg of the desired product. MS (ESI, m/z): 329.4 (MH+).

Example 61

5-tert-butyl-3-[5-cyclopropyl-4-(4-fluorophenoxy)pyridin-2-yl]-1,2,4-oxadiazole

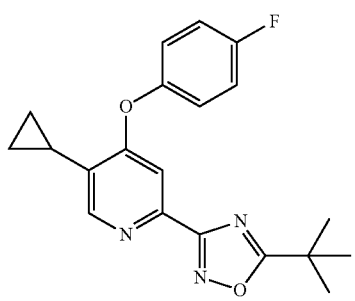 [SMILES: CC(C)(C)c1nc(-c2cc(Oc3ccc(F)cc3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and 4-fluorophenol (CAS 371-41-5) as starting materials, and purified by preparative HPLC without any work-up. MS (ESI, m/z): 354.5 (MH+).

Example 62

5-tert-butyl-3-[5-cyclopropyl-4-(oxolan-3-yloxy)pyridin-2-yl]-1,2,4-oxadiazole

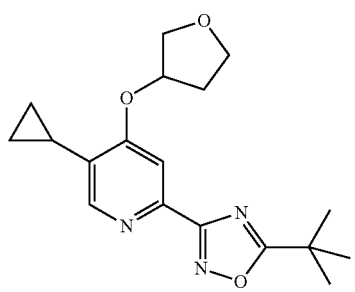 [SMILES: CC(C)(C)c1nc(-c2cc(OC3CCOC3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and tetrahydrofuran-3-ol (CAS 453-20-3) as starting materials, and purified by preparative HPLC without any work-up. MS (ESI, m/z): 330.5 (MH+).

Example 63

5-tert-butyl-3-[5-cyclopropyl-4-(oxan-4-yloxy)pyridin-2-yl]-1,2,4-oxadiazole

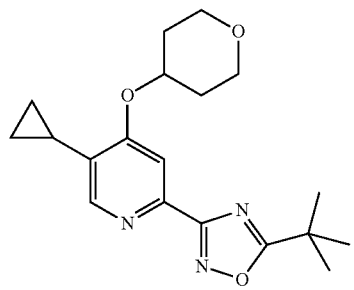 [SMILES: CC(C)(C)c1nc(-c2cc(OC3CCOCC3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and tetrahydro-2H-pyran-4-ol (CAS 2081-44-9) as starting materials, and purified by preparative HPLC without any work-up. MS (ESI, m/z): 344.5 (MH+).

Example 64

2-(5-tert-butyl-1H-imidazol-2-yl)-5-(3,3-difluoroazetidin-1-yl)-4-(2,2,2-trifluoroethoxy)pyridine a) 5-(3,3-difluoroazetidin-1-yl)-4-(2,2,2-trifluoroethoxy)picolinimidamide

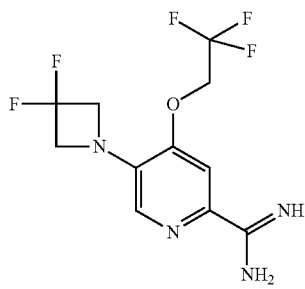 [SMILES: N=C(N)c1cc(OCC(F)(F)F)c(N2CC(F)(F)C2)cn1]

To a solution of ammonium chloride (47.4 mg, 887 µmol, Eq: 2) in toluene (0.56 mL) was added at 0° C. for 10 minutes trimethylaluminum (443 µL, 887 µmol, Eq: 2.0). Reaction was then brought at RT for 20 minutes. 5-(3,3-difluoroazetidin-1-yl)-4-(2,2,2-trifluoroethoxy)picolinonitrile (130 mg, 443 µmol, Eq: 1.00), previously described as Example 15c, dissolved in toluene was then added and the reaction mixture heated up to 80° C. and stirred for 1 h. The reaction mixture was then cooled down to RT, quenched with water and poured into a DCM/silica slurry. This was then filtered and washed through with methanol to give 250 mg of a yellow solid. The crude material was purified by flash chromatography on SiO$_2$, 10 g, gradient methanol in DCM giving 21 mg of the title compound as light yellow powder (Yield 15%). MS (ESI, m/z): 311.4 (MH+).

b) 2-(5-tert-butyl-1H-imidazol-2-yl)-5-(3,3-difluoro-azetidin-1-yl)-4-(2,2,2-trifluoroethoxy)pyridine

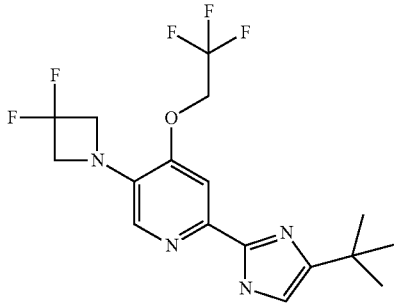 [SMILES: CC(C)(C)c1c[nH]c(-c2cc(OCC(F)(F)F)c(N3CC(F)(F)C3)cn2)n1]

5-(3,3-difluoroazetidin-1-yl)-4-(2,2,2-trifluoroethoxy)picolinimidamide (20 mg, 64.5 μmol, Eq: 1.00), 1-bromo-3,3-dimethylbutan-2-one (24.2 mg, 18.2 μL, 135 μmol, Eq: 2.1) and DBU (49.1 mg, 48.6 μL, 322 μmol, Eq: 5.0) were combined with Ethanol (0.77 mL). The reaction mixture was heated up to 115° C. and stirred overnight. The crude material was purified by preparative HPLC giving 5 mg of the title compound as white powder (Yield 19%). MS (ESI, m/z): 391.5 (MH+).

Example 65

5-tert-butyl-2-[5-cyclopropyl-4-(cyclopropyl-methoxy)pyridin-2-yl]-1,3-oxazole a) 5-cyclopropyl-4-(cyclopropylmethoxy)-N-(2-hydroxy-3,3-dimethylbutyl)picolinamide

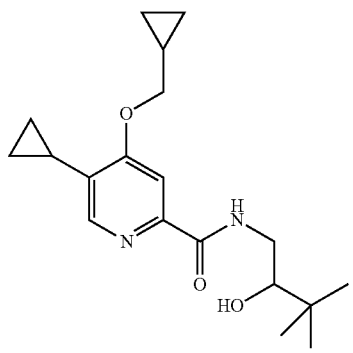 [SMILES: CC(C)(C)C(O)CNC(=O)c1cc(OCC2CC2)c(C2CC2)cn1]

To a solution of 5-cyclopropyl-4-(cyclopropylmethoxy) picolinic acid, previously described as Example 1e, (200 mg, 0.857 mmol, Eq: 1.00) in 8.5 mL DCM was added HATU (158 mg, 1.03 mmol, Eq: 1.2) and DIPEA (449 μL, 2.57 mmol, Eq: 3.0). Reaction was stirred 15 min at 40° C., then 1-amino-3,3-dimethylbutan-2-ol hydrochloride (158 mg, 1.03 mmol, Eq: 1.2) (CAS 1438-15-9) was added. Reaction was stirred 2 h at 40° C. Extraction with DCM/NaHCO₃ saturated aqueous solution. Organic layer was dried on sodium sulfate and evaporated. Column on SiO₂ with a gradient heptane/ethyl acetate gave 126 mg of the title compound as colorless viscous oil (Yield 44%). MS (ESI, m/z): 333.5 (MH+).

b) 5-cyclopropyl-4-(cyclopropylmethoxy)-N-(3,3-dimethyl-2-oxobutyl)picolinamide

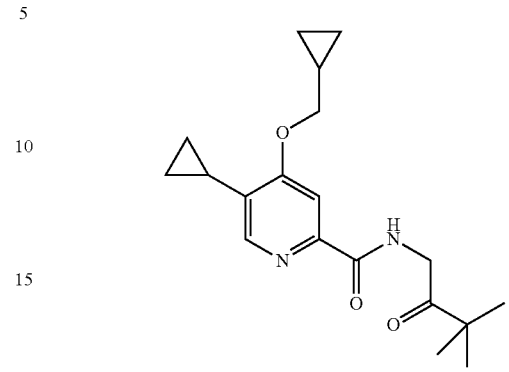

To a solution of 5-cyclopropyl-4-(cyclopropylmethoxy)-N-(2-hydroxy-3,3-dimethylbutyl)picolinamide (125 mg, 0.376 mmol, Eq: 1.00) in DCM (3.8 mL) was added Dess-Martin periodinane (181 mg, 0.414 mmol, Eq: 1.1) and the reaction was stirred overnight at RT. LC-MS showed reaction was complete. Sodium thiosulfate solution was added to the crude and stirred for 10 min before extraction with NaHCO₃ saturated aqueous solution and DCM. Column on SiO₂ with a gradient heptane/ethyl acetate gave 116 mg of the title compound as white waxy solid (Yield 93%). MS (ESI, m/z): 331.5 (MH+).

c) 5-tert-butyl-2-[5-cyclopropyl-4-(cyclopropyl-methoxy)pyridin-2-yl]-1,3-oxazole

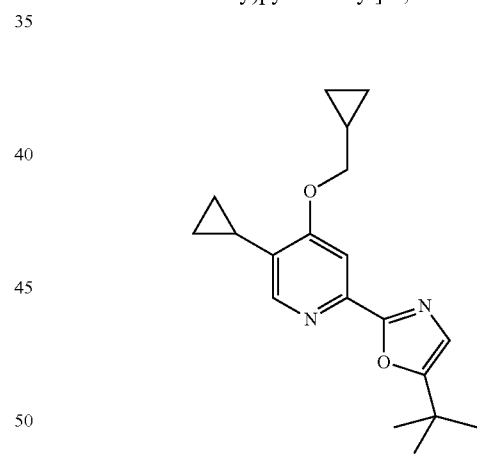

Hexachloroethane was dissolved in anhydrous acetonitrile. Then 5-cyclopropyl-4-(cyclopropylmethoxy)-N-(3,3-dimethyl-2-oxobutyl)picolinamide was dissolved in Acetonitrile and added. The reaction mixture was cooled to 0° C. and triethylamine followed by triphenylphosphine were added. The ice bath was removed and the reaction mixture was stirred for 2 hours. LC-MS showed some SM left. Another 3 Eq. hexachloroethane, triethylamine and finally triphenylphosphine were added at 0° C. Acetonitrile was evaporated and the crude extracted with DCM/brine 3 times. Organic layer was dried on Na₂SO₄ and evaporated. Column on SiO₂ with a gradient heptane/ethyl acetate to give 14 mg of the title compound (Yield 60%). MS (ESI, m/z): 313.5 (MH+).

Example 66

2-[5-cyclopropyl-4-(2,2,2-trifluoroethoxy)pyridin-2-yl]-4-methyl-4-propan-2-yl-1H-imidazol-5-one

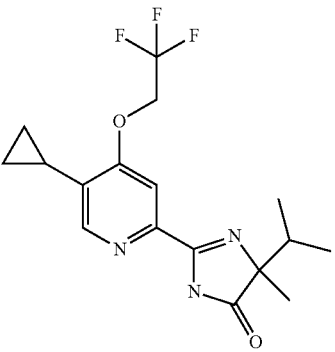 [SMILES: CC(C)C1(C)N=C(c2cc(OCC(F)(F)F)c(C3CC3)cn2)NC1=O]

5-cyclopropyl-4-(2,2,2-trifluoroethoxy)picolinic acid, previously described as Example 7e, (100 mg, 383 µmol, Eq: 1.00) in 1,2-Dichloroethane (1.91 mL) had thionyl chloride (68.3 mg, 41.9 µL, 574 µmol, Eq: 1.5) added to it. The reaction mixture was heated up to 90° C. and left to reflux for 3 h. The reaction mixture was concentrated in vacuo. Product was used immediately in the next step and dissolved in THF (526 µL). A mixture of 2-amino-2,3-dimethylbutanamide (46.6 mg, 358 µmol, Eq: 1.00) and triethylamine (36.2 mg, 49.8 µL, 358 µmol, Eq: 1.0) in 130 µL of tetrahydrofuran was added and the reaction stirred at 4 h at RT. The reaction mixture was poured into water, extracted with ethyl acetate and the organic layers combined, dried, and concentrated in vacuo to give a solid which was used immediately in the next step and dissolved in THF (536 µL). This was added to a solution of potassium hydroxide (40.3 mg, 718 µmol, Eq: 2.0) and water (15 µL) and the reaction was refluxed for 2 hours. The mixture was poured into water and extracted with ethyl acetate. The organic layers were combined before being dried on Na$_2$SO$_4$ and concentrated in vacuo. The crude material was purified by flash chromatography (SiO$_2$, 10 g, gradient ethyl acetate in heptane) giving 43 mg of the title compound as a white solid (Yield 34%). MS (ESI, m/z): 356.1 (MH+).

Example 67

5-tert-butyl-3-[5-methylsulfonyl-4-(2,2,2-trifluoroethoxy)pyridin-2-yl]-1,2,4-oxadiazole a) 2-(5-tert-butyl-1,2,4-oxadiazol-3-yl)-5-(methylsulfonyl)pyridin-4-ol

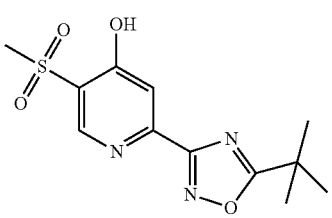 [SMILES: CC(C)(C)c1nc(-c2cc(O)c(S(C)(=O)=O)cn2)no1]

To a solution of 5-tert-butyl-3-(4-(cyclopropylmethoxy)-5-(methylsulfonyl)pyridin-2-yl)-1,2,4-oxadiazole, described as Example 43, (330 mg, 939 µmol, Eq: 1.00) in dry DCM (5 ml) under an argon atmosphere was added BBr$_3$ 1M solution in DCM (1.88 mL, 1.88 mmol, Eq: 2.0). The reaction mixture was stirred at RT overnight and monitored by LC-MS until complete conversion. The reaction mixture was quenched by addition of water, stirred for 10 min and the mixture was then poured into a separatory funnel and pH was adjusted to 7 and extracted with DCM and then ethyl acetate. All the organic layers were dried over Na$_2$SO$_4$ and evaporated down to dryness giving 140 mg of the title compound as white solid (Yield 50%). MS (ESI, m/z): 296.4 (MH−).

b) 5-tert-butyl-3-[5-methylsulfonyl-4-(2,2,2-trifluoroethoxy)pyridin-2-yl]-1,2,4-oxadiazole

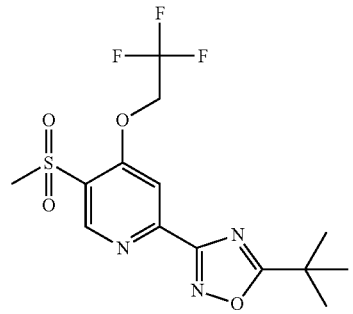 [SMILES: CC(C)(C)c1nc(-c2cc(OCC(F)(F)F)c(S(C)(=O)=O)cn2)no1]

To a solution of 2-(5-tert-butyl-1,2,4-oxadiazol-3-yl)-5-(methylsulfonyl)pyridin-4-ol (40 mg, 135 µmol, Eq: 1.00) in DMF (1 mL) was added Cs2CO3 (65.7 mg, 202 µmol, Eq: 1.5) and 2,2,2-trifluoroethyl trifluoromethanesulfonate (CAS 6226-25-1) (62.4 mg, 38.8 µL, 269 µmol, Eq: 2.0). Reaction was heated at 90° C. during 1.5 h in the microwave and purified by preparative HPLC without any work-up. MS (ESI, m/z): 380.5 (MH+).

Example 68

2-[5-cyclopropyl-4-(2,2,2-trifluoroethoxy)pyridin-2-yl]-4-ethyl-4-methyl-1H-imidazol-5-one

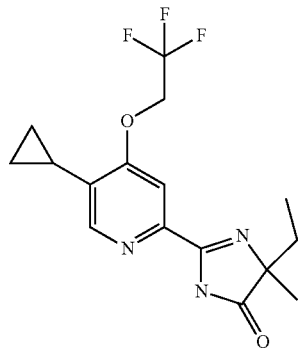 [SMILES: CCC1(C)N=C(c2cc(OCC(F)(F)F)c(C3CC3)cn2)NC1=O]

The title compound was synthesized in a similar manner as Example 66, using 5-cyclopropyl-4-(2,2,2-trifluoroethoxy)picolinic acid (Eq: 1.0), previously described as Example 7e, with CDI (Eq: 1.1), DIPEA (Eq: 2.2) and 1-amino-2-methyl-1-oxobutan-2-aminium chloride (CAS 18305-22-1) as starting materials for the amide coupling step. MS (ESI, m/z): 342.1 (MH+).

Example 69

2-[5-cyclopropyl-4-(2,2,2-trifluoroethoxy)pyridin-2-yl]-4-methyl-4-(2-methylpropyl)-1H-imidazol-5-one

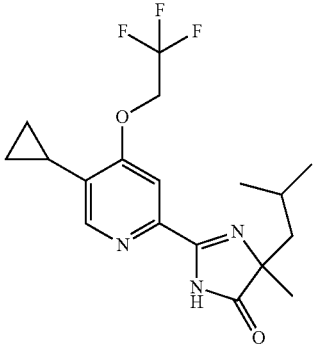 [SMILES: CC(C)CC1(C)N=C(c2cc(OCC(F)(F)F)c(C3CC3)cn2)NC1=O]

The title compound was synthesized in analogy to Example 68, using 5-cyclopropyl-4-(2,2,2-trifluoroethoxy) picolinic acid (Eq: 1.0), previously described as Example 7e, with CDI (Eq: 1.1), DIPEA (Eq: 2.2) and 2-amino-2,4-dimethylpentanamide (CAS 113509-60-7) as starting materials for the amide coupling step. MS (ESI, m/z): 370.5 (MH+).

Example 70

5-tert-butyl-3-[5-chloro-4-(2,2,2-trifluoroethoxy)pyridin-2-yl]-1,2,4-oxadiazole a) 2,5-dichloro-4-(2,2,2-trifluoroethoxy)pyridine

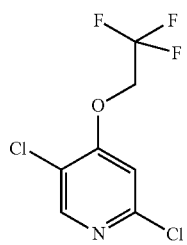 [SMILES: FC(F)(F)COc1cc(Cl)ncc1Cl]

To a solution of 2,5-dichloropyridin-4-ol (CAS 847664-65-7) (5 g, 30.5 mmol, Eq: 1.00) in DMF (51 mL) was added cesium carbonate (14.9 g, 45.7 mmol, Eq: 1.5) and 2,2,2-trifluoroethyl trifluoromethanesulfonate (6.59 mL, 45.7 mmol, Eq: 1.5). Reaction was heated at 90° C. overnight. Reaction was filtered to remove Cs$_2$CO$_3$ (cake washed with ethyl acetate) and solvent evaporated. Extraction of the crude using ethyl acetate/water. Organic layer was dried on Na$_2$SO$_4$ and evaporated. Column on SiO$_2$ using MPLC Isco with a gradient heptane/ethyl acetate gave 6.64 g of title compound as off-white solid (Yield 88%). MS (ESI, m/z): 246.3 (MH+).

b) 5-chloro-4-(2,2,2-trifluoroethoxy)picolinonitrile

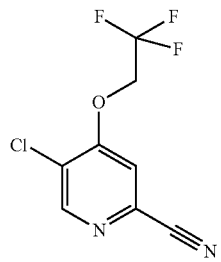 [SMILES: N#Cc1cc(OCC(F)(F)F)c(Cl)cn1]

2,5-dichloro-4-(2,2,2-trifluoroethoxy)pyridine (4 g, 16.3 mmol, Eq: 1.00), Dicyanozinc (2.1 g, 17.9 mmol, Eq: 1.1), 1,1'-bis(diphenylphosphino)ferrocene (721 mg, 1.3 mmol, Eq: 0.08) and Pd$_2$(dba)$_3$ (744 mg, 0.813 mmol, Eq: 0.05) were combined in DMF and the reaction heated at 100° C. 2 days. Evaporation of the solvent, extraction with ethyl acetate/NaHCO$_3$ saturated aqueous solution Organic layer dried on sodium sulfate and evaporated. Column on SiO$_2$ with MPLC Isco with a gradient heptane/ethyl acetate gave 2.1 g of title compound as white solid (Yield 54%). MS (ESI, m/z): 237.3 (MH+).

c) 5-chloro-N-hydroxy-4-(2,2,2-trifluoroethoxy)picolinimidamide

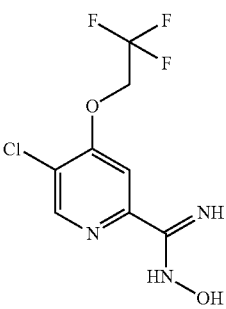 [SMILES: N=C(NO)c1cc(OCC(F)(F)F)c(Cl)cn1]

To a solution of 5-chloro-4-(2,2,2-trifluoroethoxy)picolinonitrile (200 mg, 0.845 mmol, Eq: 1.00) in EtOH (5.6 mL) was added hydroxylamine hydrochloride (65 mg, 0.93 mmol, Eq: 1.1) and triethylamine (128 mg, 177 μL, 1.27 mmol, Eq: 1.5). The reaction was heated with microwave 30 min at 80° C. and monitered with LC-MS. The reaction mixture was poured into a separating funnel, DCM was added and the mixture was extracted with aqueous NaHCO$_3$ saturated solution. The organic phase was dried over Na$_2$SO$_4$ and concentrated in vacuo to give 223 mg of title compound as white powder (Yield 97%). MS (ESI, m/z): 270.4 (MH+).

d) 5-tert-butyl-3-[5-chloro-4-(2,2,2-trifluoroethoxy)pyridin-2-yl]-1,2,4-oxadiazole

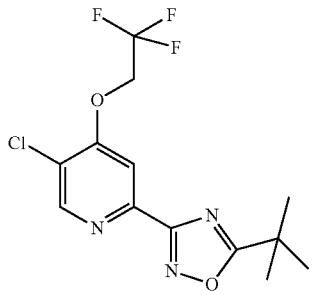 [SMILES: CC(C)(C)c1nc(-c2cc(OCC(F)(F)F)c(Cl)cn2)no1]

To a solution of 5-chloro-N-hydroxy-4-(2,2,2-trifluoroethoxy)picolinimidamide (0.1 g, 371 µmol, Eq: 1.00) in dry DMF (2.5 mL) under argon atmosphere was added DIPEA (130 µL, 742 µmol, Eq: 2.0) followed by pivaloyl chloride (CAS 3282-30-2) (53.7 mg, 54.8 µL, 445 µmol, Eq: 1.2). The reaction was stirred at RT for 45 min and controlled by LC-MS which showed complete conversion to the intermediate. The reaction mixture was heated with microwave 30 min at 120° C. and controlled by LC-MS which showed complete conversion to the desired product. The solvent was evaporated and the crude diluted with ethyl acetate, poured into a separatory funnel and extracted with NaHCO$_3$ aqueous saturated solution. The organic phase was dried over Na$_2$SO$_4$ and evaporated down to dryness. The crude material was purified by flash chromatography (SiO$_2$, 20 g, gradient ethyl acetate in heptane) gave 92 mg of the title compound as white powder (Yield 73%). MS (ESI, m/z): 336.4 (MH+).

Example 71

3-[5-chloro-4-(2,2,2-trifluoroethoxy)pyridin-2-yl]-5-cyclopropyl-1,2,4-oxadiazole

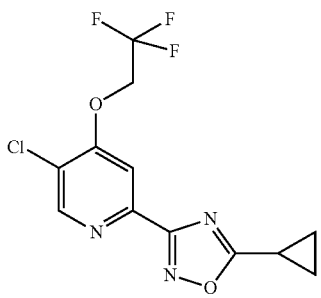 [SMILES: FC(F)(F)COc1cc(-c2noc(C3CC3)n2)ncc1Cl]

The title compound was synthesized in analogy to Example 70d, using 5-chloro-N-hydroxy-4-(2,2,2-trifluoroethoxy)picolinimidamide and cyclopropanecarboxylic acid (CAS 1759-53-1) as starting materials, with HATU (Eq: 1.2) and DIPEA (Eq: 2.0), and heated with microwave 30 min at 120° C. MS (ESI, m/z): 320.4 (MH+).

Example 72

5-cyclopropyl-3-[5-cyclopropyl-4-(2,2,2-trifluoroethoxy)pyridin-2-yl]-1,2,4-oxadiazole

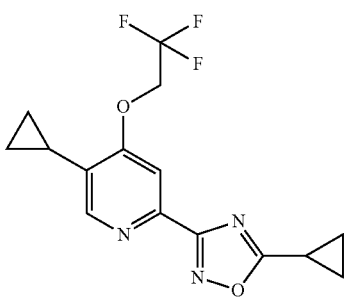 [SMILES: FC(F)(F)COc1cc(-c2noc(C3CC3)n2)ncc1C1CC1]

The title compound was synthesized in analogy to Example 33b, using 5-cyclopropyl-N'-hydroxy-4-(2,2,2-trifluoroethoxy)picolinimidamide and cyclopropanecarbonyl chloride (CAS 4023-34-1) as starting materials, and purified by purified by flash chromatography. MS (ESI, 111/Z): 326.6 (MH+).

Example 73

1-[2-(5-tert-butyl-1,2,4-oxadiazol-3-yl)-5-cyclopropylpyridin-4-yl]pyrrolidin-3-ol

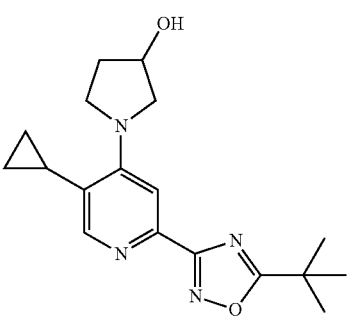 [SMILES: CC(C)(C)c1nc(-c2cc(N3CCC(O)C3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and 3-pyrrolidinol (CAS 40499-83-0) (Eq: 2.0) as starting materials in NMP with K$_2$CO$_3$ (Eq: 3.0), heated 1 h30 at 200° C. with microwave, and purified by preparative HPLC without any work-up. MS (ESI, m/z): 329.6 (MH+).

Example 74

5-tert-butyl-3-[5-cyclopropyl-4-(3,3,4,4-tetrafluoropyrrolidin-1-yl)pyridin-2-yl]-1,2,4-oxadiazole

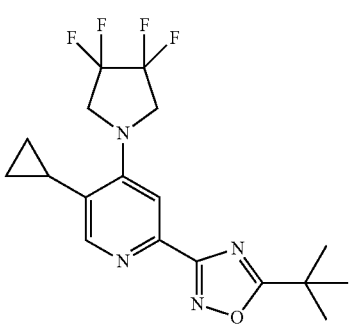 [SMILES: CC(C)(C)c1nc(-c2cc(N3CC(F)(F)C(F)(F)C3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and 3,3,4,4-tetrafluoropyrrolidine hydrochloride (CAS 1810-13-5) (Eq: 2.0) as starting materials in Sulfolane with $K_2CO_3$ (Eq: 3.0), heated 2 h at 180° C. with microwave, and purified by preparative HPLC without any work-up. MS (ESI, m/z): 385.6 (MH+).

Example 75

5-tert-butyl-3-[5-cyclopropyl-4-(4-methylsulfonylphenoxy)pyridin-2-yl]-1,2,4-oxadiazole

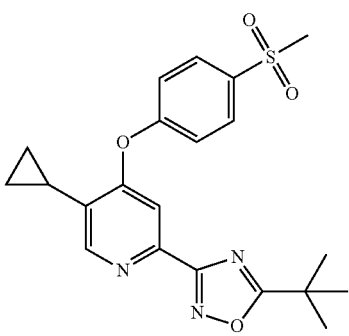 [SMILES: CC(C)(C)c1nc(-c2cc(Oc3ccc(S(C)(=O)=O)cc3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and 4-methylsulfonylphenol (CAS 14763-60-1) (Eq: 1.2) as starting materials in NMP, heated 1 h at 180° C. with microwave, and purified by preparative HPLC without any work-up. MS (ESI, m/z): 414.6 (MH+).

Example 76

7-[2-(5-tert-butyl-1,2,4-oxadiazol-3-yl)-5-cyclopropylpyridin-4-yl]-2-oxa-7-azaspiro[3.4]octane

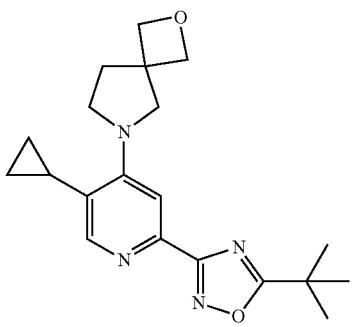 [SMILES: CC(C)(C)c1nc(-c2cc(N3CCC4(COC4)C3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and 2-oxa-6-azaspiro[3.4]octane (CAS 220290-68-6) (Eq: 2.0) as starting materials in NMP with $K_2CO_3$ (Eq: 3.0), heated 1 h30 at 200° C. with microwave, and purified by preparative HPLC without any work-up. MS (ESI, m/z): 355.6 (MH+).

Example 77

5-tert-butyl-3-[5-cyclopropyl-4-(3,3-difluoropyrrolidin-1-yl)pyridin-2-yl]-1,2,4-oxadiazole

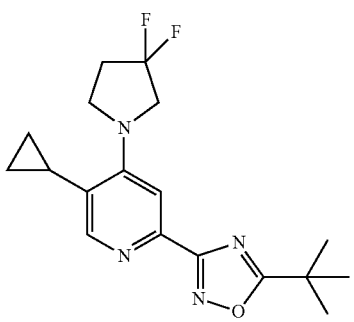 [SMILES: CC(C)(C)c1nc(-c2cc(N3CCC(F)(F)C3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and 3,3-difluoropyrrolidine hydrochloride (CAS 163457-23-6) (Eq: 2.0) as starting materials in Sulfolane with $K_2CO_3$ (Eq: 3.0), heated 30 min at 220° C. with microwave, and purified by preparative HPLC without any work-up. MS (ESI, m/z): 349.6 (MH+).

Example 78

4-[2-(5-tert-butyl-1,2,4-oxadiazol-3-yl)-5-cyclopropylpyridin-4-yl]morpholine

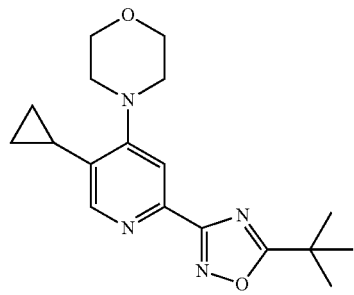 [SMILES: CC(C)(C)c1nc(-c2cc(N3CCOCC3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and morpholine (CAS 110-91-8) (Eq: 1.2) as starting materials in DMSO with CsF (Eq: 1) and triethylamine (Eq: 2.0), heated 24 h at 150° C., and purified by preparative HPLC without any work-up. MS (ESI, m/z): 329.6 (MH+).

Example 79

5-tert-butyl-3-(5-cyclopropyl-4-pyrrolidin-1-ylpyridin-2-yl)-1,2,4-oxadiazole

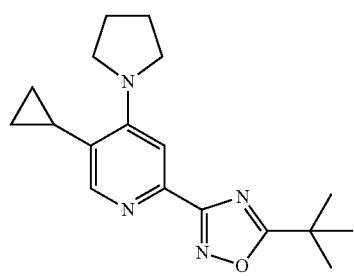 [SMILES: CC(C)(C)c1nc(-c2cc(N3CCCC3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and pyrrolidine (CAS 123-75-1) (Eq: 2) as starting materials in NMP with $K_2CO_3$ (Eq: 3.0), heated 1 h30 at 200° C. with microwave, and purified by preparative HPLC without any work-up. MS (ESI, m/z): 313.3 (MH+).

Example 80

5-tert-butyl-3-(5-cyclopropyl-4-cyclopropylsulfonylpyridin-2-yl)-1,2,4-oxadiazole

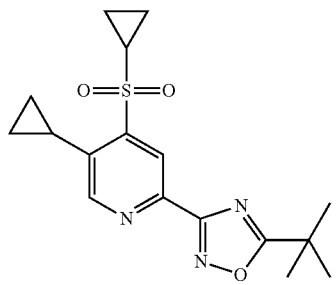 [SMILES: CC(C)(C)c1nc(-c2cc(S(=O)(=O)C3CC3)c(C3CC3)cn2)no1]

To a solution of 5-tert-butyl-3-(4-chloro-5-cyclopropylpyridin-2-yl)-1,2,4-oxadiazole (50 mg, 0.18 mmol), previously described as Example 48d, in DMA (2 mL) in a microwave vial, was added sodium cyclopropanesulfinate (CAS 910209-21-1) (46.1 mg, 0.36 mmol, Eq: 2.0) and DMAP (44 mg, 0.36 mmol, Eq: 2.0). Tube was sealed and reaction heated 2 days at 140° C. DMA was evaporated. Crude was then extracted with ethyl acetate/NaHCO$_3$ aqueous saturated solution. Organic layer was dried on Na$_2$SO$_4$ and evaporated. Column on SiO$_2$ with a gradient ethyl acetate/heptane gave 37 mg of the title compound as colorless viscous oil (Yield 59%). MS (ESI, m/z): 348.6 (MH+).

Example 81

5-tert-butyl-3-[5-cyclopropyl-4-(3-methoxyazetidin-1-yl)pyridin-2-yl]-1,2,4-oxadiazole

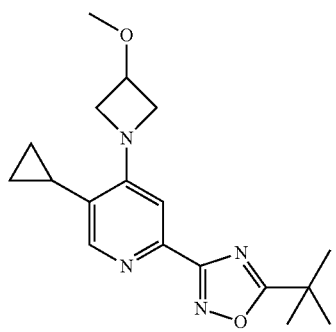 [SMILES: COC1CN(c2cc(-c3noc(C(C)(C)C)n3)ncc2C2CC2)C1]

The title compound was synthesized in analogy to Example 48e, using 5-tert-butyl-3-(4-chloro-5-cyclopropylpyridin-2-yl)-1,2,4-oxadiazole and 3-methoxyazetidine (CAS 110925-17-2) (Eq: 2.0) as starting materials in ethylene glycol with Cs$_2$CO$_3$ (Eq: 3.0), heated 6 h at 100° C., and purified by preparative HPLC after filtration. MS (ESI, m/z): 329.6 (MH+).

Example 82

6-[2-(5-tert-butyl-1,2,4-oxadiazol-3-yl)-5-cyclopropylpyridin-4-yl]-2-oxa-6-azaspiro[3.3]heptane

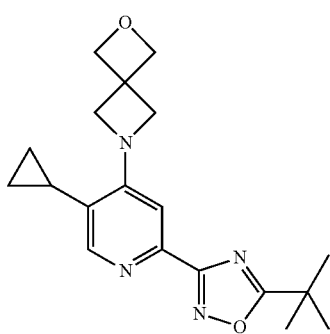 [SMILES: CC(C)(C)c1nc(-c2cc(N3CC4(COC4)C3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and 2-oxa-6-azaspiro[3.3]heptane (CAS 174-78-7) (Eq: 2) as starting materials in ethylene glycol with Cs$_2$CO$_3$ (Eq: 3), heated 6 h at 100° C., and purified by preparative HPLC after filtration. MS (ESI, m/z): 341.6 (MH+).

Example 83

5-tert-butyl-3-[5-cyclopropyl-4-(2-ethoxyethoxy)pyridin-2-yl]-1,2,4-oxadiazole

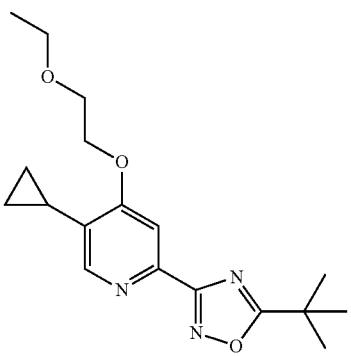 [SMILES: CCOCCOc1cc(-c2noc(C(C)(C)C)n2)ncc1C1CC1]

The title compound was synthesized in analogy to Example 48e, using 5-tert-butyl-3-(4-chloro-5-cyclopropylpyridin-2-yl)-1,2,4-oxadiazole and 2-ethoxyethanol (CAS 110-80-5) as starting materials, and purified by preparative HPLC without any work-up. MS (ESI, m/z): 332.6 (MH+).

Example 84

5-tert-butyl-3-[5-cyclopropyl-4-(1-methoxybutan-2-yloxy)pyridin-2-yl]-1,2,4-oxadiazole

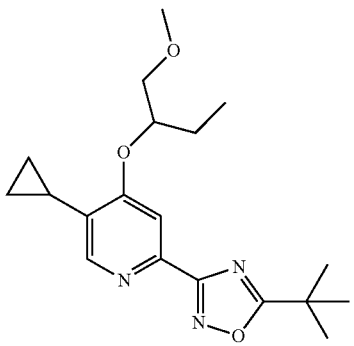 [SMILES: CCC(COC)Oc1cc(-c2noc(C(C)(C)C)n2)ncc1C1CC1]

The title compound was synthesized in analogy to Example 48e, using 5-tert-butyl-3-(4-chloro-5-cyclopropylpyridin-2-yl)-1,2,4-oxadiazole and 1-methoxybutan-2-ol (CAS 53778-73-7) as starting materials, and purified by preparative HPLC without any work-up. MS (ESI, m/z): 346.6 (MH+).

Example 85

5-tert-butyl-3-[5-cyclopropyl-4-[2-[(2-methylpropan-2-yl)oxy]ethoxy]pyridin-2-yl]-1,2,4-oxadiazole

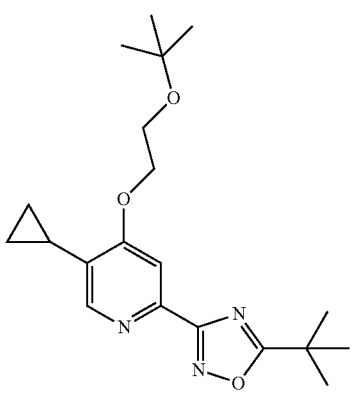 [SMILES: CC(C)(C)OCCOc1cc(-c2noc(C(C)(C)C)n2)ncc1C1CC1]

The title compound was synthesized in analogy to Example 48e, using 5-tert-butyl-3-(4-chloro-5-cyclopropylpyridin-2-yl)-1,2,4-oxadiazole and ethylene glycol mono-tert-butyl ether (CAS 7580-85-0) as starting materials, and purified by preparative HPLC without any work-up. MS (ESI, m/z): 360.7 (MH+).

Example 86

5-tert-butyl-3-[5-cyclopropyl-4-[1-[(2-methylpropan-2-yl)oxy]propan-2-yloxy]pyridin-2-yl]-1,2,4-oxadiazole

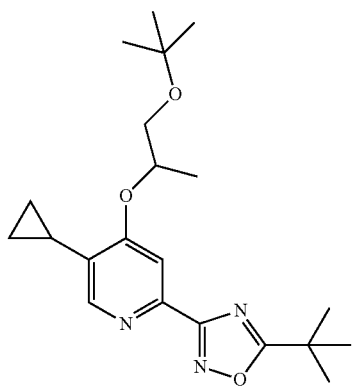 [SMILES: CC(COC(C)(C)C)Oc1cc(-c2noc(C(C)(C)C)n2)ncc1C1CC1]

The title compound was synthesized in analogy to Example 48e, using 5-tert-butyl-3-(4-chloro-5-cyclopropylpyridin-2-yl)-1,2,4-oxadiazole and 1-tert-butoxy-propan-2-ol (CAS 57018-52-7) as starting materials, and purified by preparative HPLC without any work-up. MS (ESI, m/z): 374.8 (MH+).

Example 87

5-tert-butyl-3-[5-cyclopropyl-4-(1-methoxypropan-2-yloxy)pyridin-2-yl]-1,2,4-oxadiazole

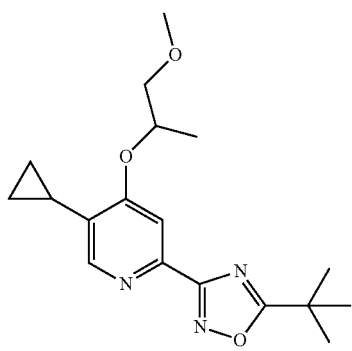 [SMILES: COCC(C)Oc1cc(-c2noc(C(C)(C)C)n2)ncc1C1CC1]

The title compound was synthesized in analogy to Example 48e, using 5-tert-butyl-3-(4-chloro-5-cyclopropylpyridin-2-yl)-1,2,4-oxadiazole and 1-methoxy-propan-2-ol (CAS 107-98-2) as starting materials, and purified by preparative HPLC without any work-up. MS (ESI, m/z): 332.7 (MH+).

Example 88

5-tert-butyl-3-[5-cyclopropyl-4-(oxan-3-yloxy)pyridin-2-yl]-1,2,4-oxadiazole

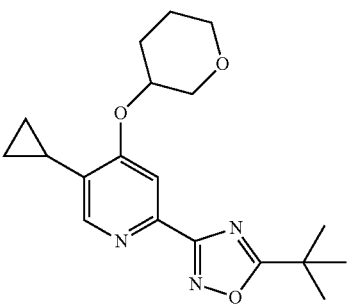 [SMILES: CC(C)(C)c1nc(-c2cc(OC3CCCOC3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and tetrahydro-pyran-3-ol (CAS 19752-84-2) as starting materials, and purified by preparative HPLC without any work-up. MS (ESI, m/z): 344.6 (MH+).

Example 89

5-tert-butyl-3-[5-cyclopropyl-4-(3-methoxybutoxy)pyridin-2-yl]-1,2,4-oxadiazole

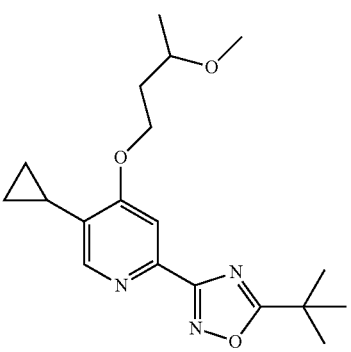 [SMILES: COC(C)CCOc1cc(-c2noc(C(C)(C)C)n2)ncc1C1CC1]

The title compound was synthesized in analogy to Example 48e, using 5-tert-butyl-3-(4-chloro-5-cyclopropylpyridin-2-yl)-1,2,4-oxadiazole and 3-methoxy-butanol (CAS 2517-43-3) as starting materials, and purified by preparative HPLC without any work-up. MS (ESI, m/z): 346.6 (MH+).

Example 90

5-tert-butyl-3-[5-cyclopropyl-4-(oxetan-3-yl-methoxy)pyridin-2-yl]-1,2,4-oxadiazole

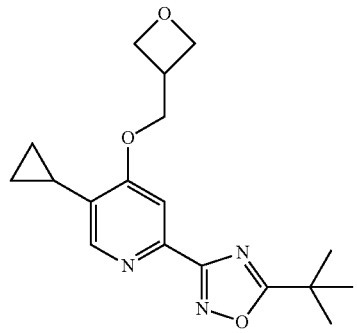 [SMILES: CC(C)(C)c1nc(-c2cc(OCC3COC3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and 3-oxetanemethanol (CAS 6246-06-6) as starting materials, and purified by preparative HPLC without any work-up. MS (ESI, m/z): 330.6 (MH+).

Example 91

5-cyclopropyl-3-[5-cyclopropyl-4-[(2S)-1,1,1-trifluoropropan-2-yl]oxypyridin-2-yl]-1,2,4-oxadiazole

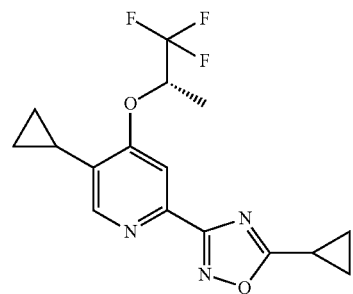 [SMILES: C[C@H](Oc1cc(-c2noc(C3CC3)n2)ncc1C1CC1)C(F)(F)F]

The title compound was synthesized in analogy to Example 33b, using (S,Z)-5-cyclopropyl-N'-hydroxy-4-(1,1,1-trifluoropropan-2-yloxy)picolinimidamide (prepared in analogy to Example 33a but with (S)-1,1,1-trifluoropropan-2-ol for the first Example 7a) and isobutyryl chloride (CAS 79-30-1) as starting materials, and purified by purified by flash chromatography. MS (ESI, m/z): 340.1 (MH+).

Example 92

5-tert-butyl-3-[5-cyclopropyl-4-(1-ethylpyrrolidin-3-yl)oxypyridin-2-yl]-1,2,4-oxadiazole

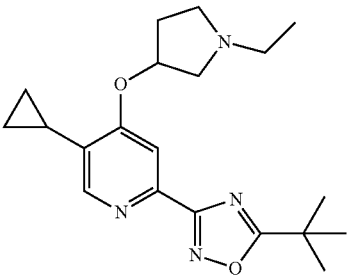 [SMILES: CCN1CCC(Oc2cc(-c3noc(C(C)(C)C)n3)ncc2C2CC2)C1]

The title compound was synthesized in analogy to Example 48e, using 5-tert-butyl-3-(4-chloro-5-cyclopropylpyridin-2-yl)-1,2,4-oxadiazole and 1-ethyl-3-pyrrolidinol (CAS 30727-14-1) as starting materials, and purified by preparative HPLC without any work-up. MS (ESI, m/z): 357.6 (MH+).

Example 93

5-tert-butyl-3-[5-cyclopropyl-4-(1-propan-2-ylpyrrolidin-3-yl)oxypyridin-2-yl]-1,2,4-oxadiazole

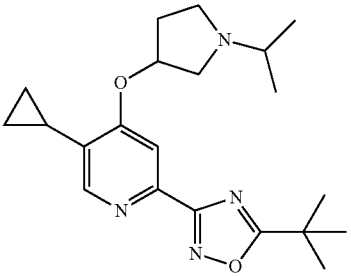 [SMILES: CC(C)N1CCC(Oc2cc(-c3noc(C(C)(C)C)n3)ncc2C2CC2)C1]

The title compound was synthesized in analogy to Example 48e, using 5-tert-butyl-3-(4-chloro-5-cyclopropylpyridin-2-yl)-1,2,4-oxadiazole and 1-isopropyl-pyrrolidinol (CAS 42729-56-6) as starting materials, and purified by preparative HPLC without any work-up. MS (ESI, m/z): 371.7 (MH+).

Example 94

5-tert-butyl-3-[5-cyclopropyl-4-(2-pyrrolidin-1-ylethoxy)pyridin-2-yl]-1,2,4-oxadiazole

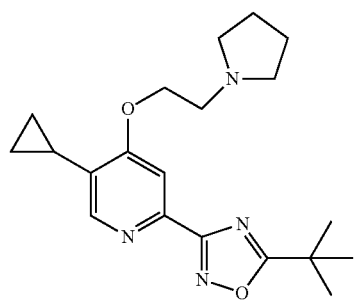 [SMILES: CC(C)(C)c1nc(-c2cc(OCCN3CCCC3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and 1-(2-hydroxyethyl)pyrrolidine (CAS 2955-88-6) as starting materials, and purified by preparative HPLC without any work-up. MS (ESI, m/z): 357.6 (MH+).

Example 95

5-tert-butyl-3-[5-cyclopropyl-4-(2-piperidin-1-ylethoxy)pyridin-2-yl]-1,2,4-oxadiazole

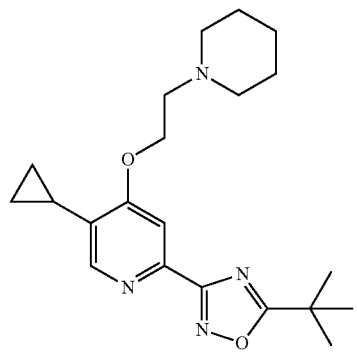 [SMILES: CC(C)(C)c1nc(-c2cc(OCCN3CCCCC3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and 1-(2-hydroxyethyl)piperidine (CAS 3040-44-6) as starting materials, and purified by preparative HPLC without any work-up. MS (ESI, m/z): 371.7 (MH+).

Example 96

5-tert-butyl-3-[5-cyclopropyl-4-(1-piperidin-1-ylpropan-2-yloxy)pyridin-2-yl]-1,2,4-oxadiazole

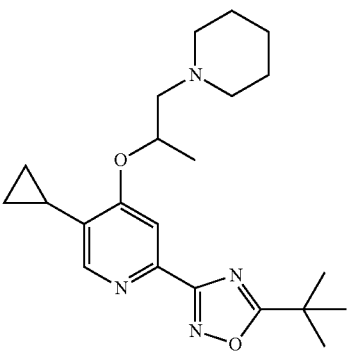 [SMILES: CC(CN1CCCCC1)Oc1cc(-c2noc(C(C)(C)C)n2)ncc1C1CC1]

The title compound was synthesized in analogy to Example 48e, using 5-tert-butyl-3-(4-chloro-5-cyclopropylpyridin-2-yl)-1,2,4-oxadiazole and alpha-methyl-1-piperidineethanol (CAS 934-90-7) as starting materials, and purified by preparative HPLC without any work-up. MS (ESI, m/z): 385.7 (MH+).

Example 97

5-tert-butyl-3-[5-cyclopropyl-4-[(1-methylpiperidin-2-yl)methoxy]pyridin-2-yl]-1,2,4-oxadiazole

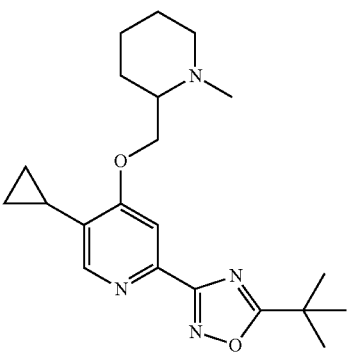 [SMILES: CN1CCCCC1COc1cc(-c2noc(C(C)(C)C)n2)ncc1C1CC1]

The title compound was synthesized in analogy to Example 48e, using 5-tert-butyl-3-(4-chloro-5-cyclopropylpyridin-2-yl)-1,2,4-oxadiazole and 1-methyl-2-piperidinemethanol (CAS 20845-34-5) as starting materials, and purified by preparative HPLC without any work-up. MS (ESI, m/z): 371.7 (MH+).

Example 98

2-tert-butyl-5-[5-cyclopropyl-4-(oxan-4-yloxy)pyridin-2-yl]-1,3,4-oxadiazole a) 5-cyclopropyl-4-(tetrahydro-2H-pyran-4-yloxy)picolinonitrile

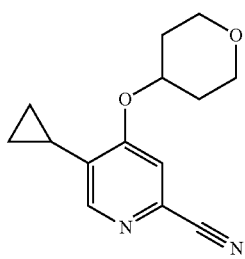 [SMILES: N#Cc1cc(OC2CCOCC2)c(C2CC2)cn1]

To a solution of 4-chloro-5-cyclopropylpicolinonitrile (300 mg, 1.68 mmol, Eq: 1.00), previously described as Example 48b, in dry DMF (11 mL) with tetrahydro-2H-pyran-4-ol (CAS 2081-44-9) (189 mg, 176 µL, 1.85 mmol, Eq: 1.1) was added NaH (60% in oil, 73.9 mg, 1.85 mmol, Eq: 1.1). The reaction was stirred at RT 15 min then 30 min at 110° C. with microwave. The solvent was partially evaporated. Extraction with ethyl acetate/NaHCO₃ saturated aqueous solution Organic layer dried on Na₂SO₄ and evaporated. Column on SiO₂ using MPLC ISCO with a gradient heptane/ethyl acetate gave 245 mg of the title compound as off-white powder (Yield 59%). MS (ESI, m/z): 245.6 (MH+).

b) 5-cyclopropyl-4-(tetrahydro-2H-pyran-4-yloxy)picolinic acid

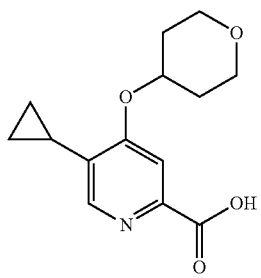 [SMILES: O=C(O)c1cc(OC2CCOCC2)c(C2CC2)cn1]

5-cyclopropyl-4-(tetrahydro-2H-pyran-4-yloxy)picolinonitrile (240 mg, 0.982 mmol, Eq: 1.00) was dissolved in HCl 25% aqueous solution (9 mL). Reaction was heated at 110° C. After 3 h reaction was complete and cooled down to RT. HCl was neutralized using 6M NaOH aqueous solution followed by NaOH pellets. Then pH adjusted to 1-2 with HCl 2M. The precipitate formed was filtered off to give 140 mg of the title compound as light yellow powder (Yield 54%). MS (ESI, m/z): 264.6 (MH+).

c) 5-cyclopropyl-N'-pivaloyl-4-(tetrahydro-2H-pyran-4-yloxy)picolinohydrazide

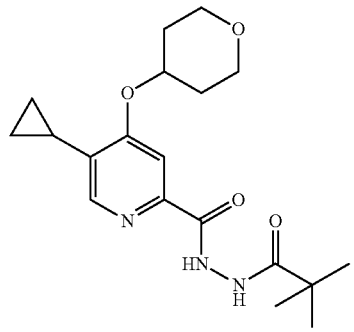 [SMILES: CC(C)(C)C(=O)NNC(=O)c1cc(OC2CCOCC2)c(C2CC2)cn1]

5-cyclopropyl-4-(tetrahydro-2H-pyran-4-yloxy)picolinic acid (70 mg, 266 µmol, Eq: 1.00) in 1,2-Dichloroethane (1.33 mL) had thionyl chloride (47.4 mg, 29.1 µL, 399 µmol, Eq: 1.5) added to it. The reaction mixture was heated up to 90° C. and left to reflux for 3 h. The reaction was complete and the reaction mixture was concentrated in vacuo. The product was used immediately in the next step and dissolved in THF (391 µL) to be reacted with pivalohydrazide (35.0 mg, 292 µmol, Eq: 1.1) and triethylamine (40.4 mg, 55.6 µL, 399 µmol, Eq: 1.5) at RT overnight. The reaction mixture was then diluted with ethyl acetate, poured into NaHCO₃ aqueous solution (1M). It was then extracted with ethyl acetate and the organic layers were combined, dried, and concentrated in vacuo to be used as a crude. MS (ESI, m/z): 362.6 (MH+).

d) 2-tert-butyl-5-[5-cyclopropyl-4-(oxan-4-yloxy)pyridin-2-yl]-1,3,4-oxadiazole

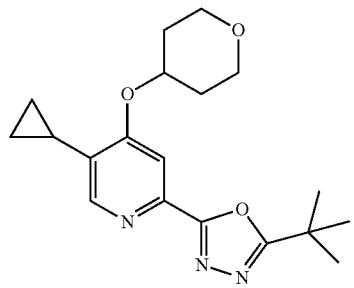 [SMILES: CC(C)(C)c1nnc(-c2cc(OC3CCOCC3)c(C3CC3)cn2)o1]

Trifluoromethanesulfonic anhydride (97.7 mg, 58.5 µL, 346 µmol, Eq: 1.5) was added slowly to a solution of triphenylphosphine oxide (193 mg, 692 µmol, Eq: 3.0) in dry DCM (0.231 mL) at 0° C. The reaction mixture was stirred for 5 minutes at this temperature before it was adjusted to room temperature and 5-cyclopropyl-N'-pivaloyl-4-(tetrahydro-2H-pyran-4-yloxy)picolinohydrazide (83.4 mg, 231 µmol, Eq: 1.00), first azeotropically dried with toluene, was added. The reaction mixture was then stirred for a further 30 minutes at RT before monitoring via LC-MS showed the reaction as complete. The reaction mixture was then diluted with DCM and poured into NaHCO₃ saturated aqueous solution and extracted with DCM. The aqueous layer was then back-extracted with DCM before the organic layers were combined, dried, and concentrated in vacuo. The crude

Example 99

5-tert-butyl-3-[5-cyclopropyl-4-(1-methylpiperidin-3-yl)oxypyridin-2-yl]-1,2,4-oxadiazole

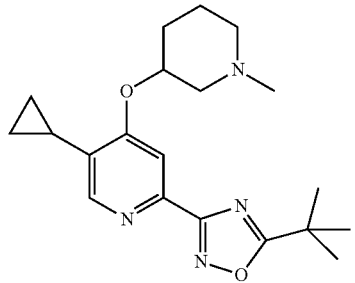 [SMILES: CN1CCCC(Oc2cc(-c3noc(C(C)(C)C)n3)ncc2C2CC2)C1]

The title compound was synthesized in analogy to Example 48e, using 5-tert-butyl-3-(4-chloro-5-cyclopropylpyridin-2-yl)-1,2,4-oxadiazole and 3-hydroxy-N-methylpiperidine (CAS 3554-74-3) as starting materials, and purified by preparative HPLC without any work-up. MS (ESI, m/z): 357.7 (MH+).

Example 100

5-tert-butyl-3-[5-cyclopropyl-4-(1-ethylpiperidin-3-yl)oxypyridin-2-yl]-1,2,4-oxadiazole

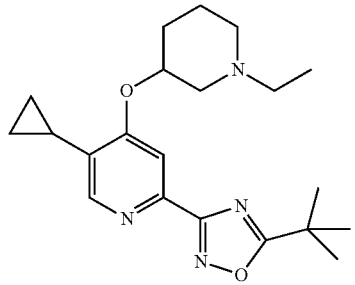 [SMILES: CCN1CCCC(Oc2cc(-c3noc(C(C)(C)C)n3)ncc2C2CC2)C1]

The title compound was synthesized in analogy to Example 48e, using 5-tert-butyl-3-(4-chloro-5-cyclopropylpyridin-2-yl)-1,2,4-oxadiazole and 3-hydroxy-N-ethylpiperidine (CAS 13444-24-1) as starting materials, and purified by preparative HPLC without any work-up. MS (ESI, m/z): 371.7 (MH+).

Example 101

2-[2-(5-tert-butyl-1,2,4-oxadiazol-3-yl)-5-cyclopropylpyridin-4-yl]oxy-N,N-diethylpropan-1-amine

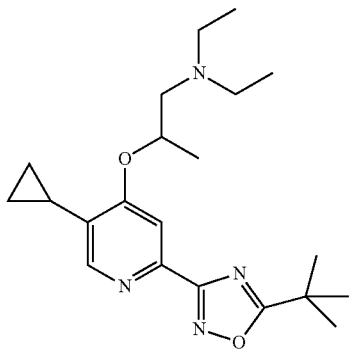 [SMILES: CCN(CC)CC(C)Oc1cc(-c2noc(C(C)(C)C)n2)ncc1C1CC1]

The title compound was synthesized in analogy to Example 48e, using 5-tert-butyl-3-(4-chloro-5-cyclopropylpyridin-2-yl)-1,2,4-oxadiazole and 1-diethylamino-2-propanol (CAS 4402-32-8) as starting materials, and purified by preparative HPLC without any work-up. MS (ESI, m/z): 373.7 (MH+).

Example 102

3-[[2-(5-tert-butyl-1,2,4-oxadiazol-3-yl)-5-cyclopropylpyridin-4-yl]oxymethyl]morpholine

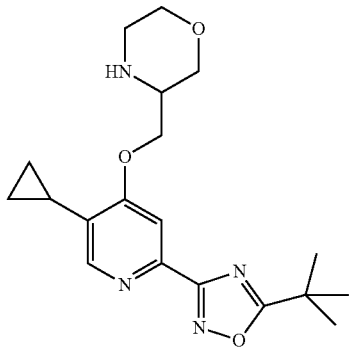 [SMILES: CC(C)(C)c1nc(-c2cc(OCC3COCCN3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and 3-hydroxymethylmorpholine (CAS 103003-01-6) as starting materials, and purified by preparative HPLC without any work-up. MS (ESI, m/z): 359.6 (MH+).

Example 103

4-[2-[2-(5-tert-butyl-1,2,4-oxadiazol-3-yl)-5-cyclopropylpyridin-4-yl]oxyethyl]morpholine

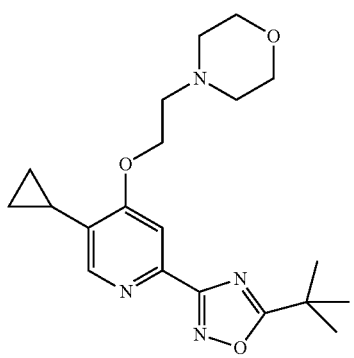 [SMILES: CC(C)(C)c1nc(-c2cc(OCCN3CCOCC3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and N-(2-hydroxyethyl)morpholine (CAS 622-40-2) as starting materials, and purified by preparative HPLC without any work-up. MS (ESI, m/z): 373.7 (MH+).

Example 104

5-tert-butyl-3-(5-cyclopropyl-4-piperidin-3-yloxy-pyridin-2-yl)-1,2,4-oxadiazole

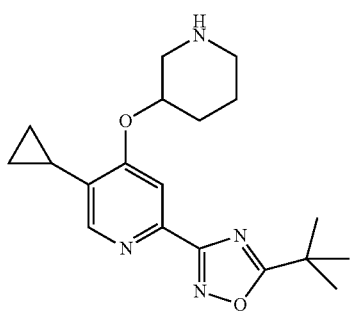 [SMILES: CC(C)(C)c1nc(-c2cc(OC3CCCNC3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and (R,S)-Boc-3-hydroxypiperidine (CAS 85275-45-2) as starting materials. The reaction was then diluted with ethyl acetate and washed with water. Organic layer was dried on Na₂SO₄ and evaporated. Product was used as a crude and directly dissolved in HCl (4M) in dioxane and stirred at RT for 2 h. The reaction mixture was purified by preparative HPLC after evaporation of the solvent. MS (ESI, m/z): 343.7 (MH+).

Example 105

5-tert-butyl-3-[5-cyclopropyl-4-[(3-fluorooxetan-3-yl)methoxy]pyridin-2-yl]-1,2,4-oxadiazole

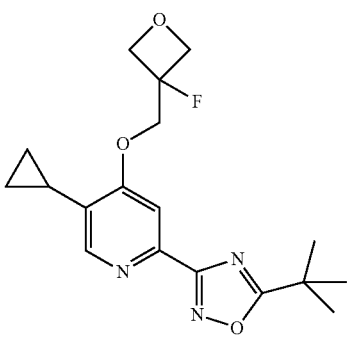 [SMILES: CC(C)(C)c1nc(-c2cc(OCC3(F)COC3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and (3-fluoro-oxetane)methanol (CAS 865451-85-0) as starting materials, and purified by preparative HPLC without any work-up. MS (ESI, m/z): 348.5 (MH+).

Example 106

5-tert-butyl-3-[5-cyclopropyl-4-[(2,5-dimethyl-1,3-oxazol-4-yl)methoxy]pyridin-2-yl]-1,2,4-oxadiazole

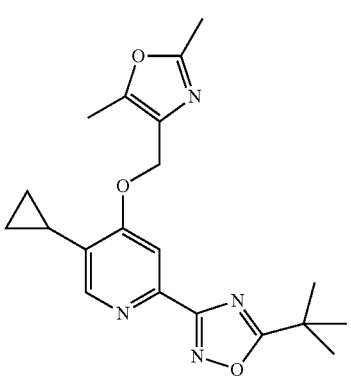 [SMILES: Cc1nc(COc2cc(-c3noc(C(C)(C)C)n3)ncc2C2CC2)c(C)o1]

The title compound was synthesized in analogy to Example 48e, using 5-tert-butyl-3-(4-chloro-5-cyclopropylpyridin-2-yl)-1,2,4-oxadiazole and (2,5-dimethyloxazol-4-yl)methanol (CAS 92901-94-5) as starting materials, and purified by preparative HPLC without any work-up. MS (ESI, m/z): 369.6 (MH+).

Example 107

5-tert-butyl-3-[5-cyclopropyl-4-[(5-methyl-1,2-oxazol-3-yl)methoxy]pyridin-2-yl]-1,2,4-oxadiazole

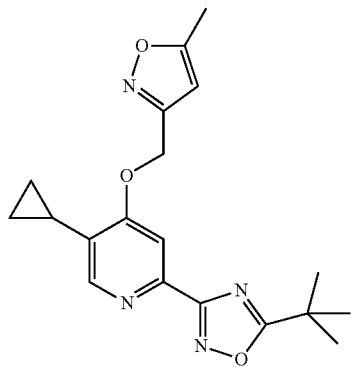 [SMILES: Cc1cc(COc2cc(-c3noc(C(C)(C)C)n3)ncc2C2CC2)no1]

The title compound was synthesized in analogy to Example 48e, using 5-tert-butyl-3-(4-chloro-5-cyclopropylpyridin-2-yl)-1,2,4-oxadiazole and (5-methylisoxazol-3-yl)methanol (CAS 35166-33-7) as starting materials, and purified by preparative HPLC without any work-up. MS (ESI, m/z): 355.6 (MH+).

Example 108

5-tert-butyl-3-[5-cyclopropyl-4-(3-methylsulfonylphenoxy)pyridin-2-yl]-1,2,4-oxadiazole

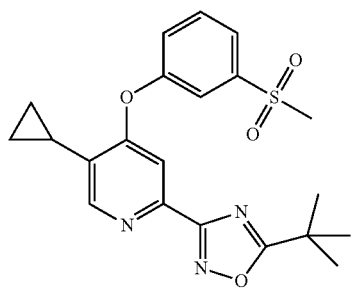 [SMILES: CC(C)(C)c1nc(-c2cc(Oc3cccc(S(C)(=O)=O)c3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and 3-(methylsulfonyl)phenol (CAS 14763-61-2) as starting materials with $Cs_2CO_3$ (Eq: 1.5), and purified by preparative HPLC without any work-up. MS (ESI, m/z): 414.5 (MH+).

Example 109

5-tert-butyl-3-[5-(3-fluorooxetan-3-yl)-4-(oxan-4-yloxy)pyridin-2-yl]-1,2,4-oxadiazole a) 3-(4,6-dichloropyridin-3-yl)oxetan-3-ol

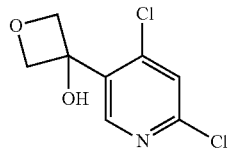 [SMILES: OC1(c2cnc(Cl)cc2Cl)COC1]

To a solution of 5-bromo-2,4-dichloropyridine (15 g, 66.1 mmol, Eq: 1.00) (CAS 849937-96-8) in dry THF (300 mL) cooled down to −15° C. under an argon atmosphere was added isopropyl magnesium chloride, lithium chloride complex (53.4 mL, 69.4 mmol, Eq: 1.05) and the mixture was stirred at −15° C. for 1 h. Slow addition of neat oxetan-3-one (5.24 g, 72.7 mmol, Eq: 1.1) to the reaction mixture cooled at −15° C. and reaction mixture was let to warm up to RT overnight. Reaction was monitored by LC-MS. Reaction was quenched by addition of water and was transferred into a separatory funnel. Dilution with ethyl acetate, extraction with saturated aqueous $NH_4Cl$ and organic phase was collected. Aqueous phase was back-extracted with ethyl acetate; organic phases were combined, dried over $Na_2SO_4$ and evaporated down to dryness. Flash chromatography with a 330 g $SiO_2$ column, eluent mixture of heptane and ethyl acetate gave 10.5 g of the desired product as a white solid (yield 72%). MS (ESI, m/z): 220.4 (MH+).

b) 4-chloro-5-(3-hydroxyoxetan-3-yl)nicolinonitrile

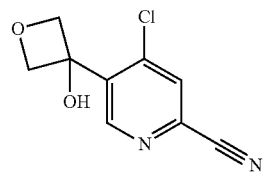 [SMILES: N#Cc1cc(Cl)c(C2(O)COC2)cn1]

To a solution of 3-(4,6-dichloropyridin-3-yl)oxetan-3-ol (5.0 g, 22.7 mmol, Eq: 1.00) in dry DMF (100 mL) under argon atmosphere was added dicyanozinc (1.47 g, 12.5 mmol, Eq: 0.55), dppf (1.26 g, 2.27 mmol, Eq: 0.1) and $Pd_2(dba)_3$ (1.04 g, 1.14 mmol, Eq: 0.05). The reaction mixture was stirred at 100° C. for 2 h and monitored by LC-MS. Evaporation of DMF, residue was diluted with ethyl acetate and poured into a separatory funnel. Extraction with saturated aqueous $NH_4Cl$. Pd colloids were formed and removed by filtration through Celite. Organic phase was collected; aqueous phase was back-extracted with ethyl acetate. Organic phases were combined, dried over $Na_2SO_4$ and evaporated down to dryness. Flash chromatography with a 120 g $SiO_2$ column, eluent mixture of heptane and ethyl acetate gave 4.1 g of the desired product (Yield 86%). MS (ESI, m/z): 209.0 (MH−).

c) 4-chloro-5-(3-fluorooxetan-3-yl)pyridine-2-carbonitrile

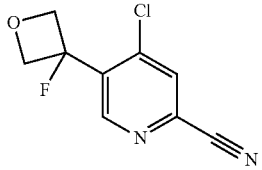 [SMILES: N#Cc1cc(Cl)c(C2(F)COC2)cn1]

To a solution of 4-chloro-5-(3-hydroxyoxetan-3-yl)picolinonitrile (0.2 g, 950 μmol, Eq: 1.00) in dry DCM (6 mL) cooled down to −78° C. was added DAST (161 mg, 132 μL, 997 μmol, Eq: 1.05). The reaction was stirred at −78° C. for 15 min, let to warm up to 0° C. and stirred at 0° C. for 1 h. Reaction was then quenched by addition of aqueous Na₂CO₃ 2M, the mixture was stirred at RT for 15 min and poured into a separatory funnel. Extraction, organic phase was collected, dried over Na₂SO₄ and evaporated down to dryness. Flash chromatography with a 20 g SiO₂ column, eluent mixture of heptane and ethyl acetate gave 184 mg of the desired product (Yield 91%). MS (ESI, m/z): 213.0 (MH+).

d) 4-chloro-5-(3-fluorooxetan-3-yl)-N'-hydroxypyridine-2-carboximidamide

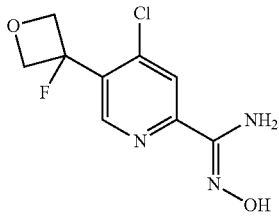 [SMILES: N/C(=N\O)c1cc(Cl)c(C2(F)COC2)cn1]

To a solution of 4-chloro-5-(3-fluorooxetan-3-yl)picolinonitrile (500 mg, 2.35 mmol, Eq: 1.00) in Ethanol (15 mL) was added hydroxylamine hydrochloride (196 mg, 2.82 mmol, Eq: 1.2) and triethylamine (476 mg, 656 μL, 4.7 mmol, Eq: 2.0). The reaction mixture was heated to 50° C. and stirred for 3 hours. Evaporation of volatiles, residue redissolved in ethyl acetate, poured into a separatory funnel and extracted with aqueous NaHCO₃ 1M, The organic layers were dried over Na₂SO₄ and evaporated down to dryness. Flash chromatography with a 20 g SiO₂ column, eluent mixture of heptane and ethyl acetate gave 490 mg of desired compound (Yield 84%). MS (ESI, m/z): 246.4 (MH+).

e) 5-tert-butyl-3-[4-chloro-5-(3-fluorooxetan-3-yl)pyridin-2-yl]-1,2,4-oxadiazole

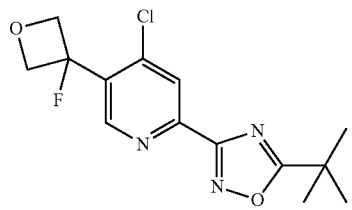 [SMILES: CC(C)(C)c1nc(-c2cc(Cl)c(C3(F)COC3)cn2)no1]

To a solution of 4-chloro-5-(3-fluorooxetan-3-yl)-N'-hydroxypicolinimidamide (490 mg, 1.99 mmol, Eq: 1.00) in dry DMF (7 mL) under argon atmosphere was added K₂CO₃ (358 mg, 2.59 mmol, Eq: 1.3) and slowly pivaloyl chloride (CAS 3282-30-2) (265 mg, 270 μL, 2.19 mmol, Eq: 1.1). The reaction mixture was stirred for 1 h at RT and controlled by LC-MS. The reaction was then stirred at 130° C. for 1 h30 and monitored by LC-MS. The reaction mixture was poured into a separatory funnel, diluted with EtOAc and extracted with aqueous NaHCO₃ 1M. The organic layer was dried over Na₂SO₄ and evaporated down to dryness. Purification by flash chromatography gave 374 mg of the title compound (Yield 54%). MS (ESI, m/z): 312.5 (MH+).

f) 5-tert-butyl-3-[5-(3-fluorooxetan-3-yl)-4-(oxan-4-yloxy)pyridin-2-yl]-1,2,4-oxadiazole

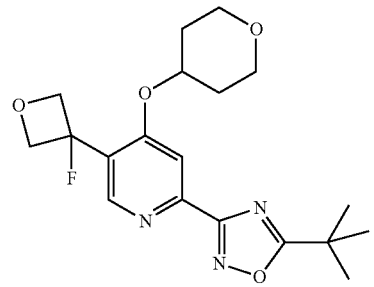 [SMILES: CC(C)(C)c1nc(-c2cc(OC3CCOCC3)c(C3(F)COC3)cn2)no1]

To a solution of 5-tert-butyl-3-(4-chloro-5-(3-fluorooxetan-3-yl)pyridin-2-yl)-1,2,4-oxadiazole (50 mg, 144 μmol, Eq: 1.00) in dry DMF (1 mL) were added NaH (6.35 mg, 159 μmol, Eq: 1.1) and tetrahydropyran-4-ol (16.2 mg, 159 μmol, Eq: 1.1) (CAS 2081-44-9). The reaction was stirred at RT for 15 min and then stirred at 110° C. for 30 min under microwave radiation, reaction was monitored by LC-MS. Reaction was quenched by addition of few drops of water, and mixture was directly purified by preparative HPLC with any work-up procedure giving 43 mg of the title compound. MS (ESI, m/z): 378.6 (MH+).

Example 110

5-tert-butyl-3-[5-(3-fluorooxetan-3-yl)-4-(4-fluorophenoxy)pyridin-2-yl]-1,2,4-oxadiazole

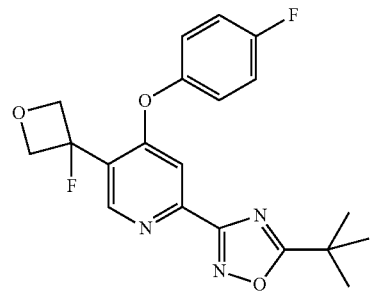 [SMILES: CC(C)(C)c1nc(-c2cc(Oc3ccc(F)cc3)c(C3(F)COC3)cn2)no1]

The title compound was synthesized in analogy to Example 109f, using 5-tert-butyl-3-(4-chloro-5-(3-fluorooxetan-3-yl)pyridin-2-yl)-1,2,4-oxadiazole and 4-fluorophenol (CAS 371-41-5) as starting materials, and purified by preparative HPLC without any work-up. MS (ESI, m/z): 388.5 (MH+).

Example 111

3-[2-[5-cyclopropyl-4-(2,2,2-trifluoroethoxy)pyridin-2-yl]-4-methyl-5H-1,3-oxazol-4-yl]-5-methyl-1,2,4-oxadiazole a) N-(1-(benzyloxy)propan-2-ylidene)-2-methylpropane-2-sulfinamide

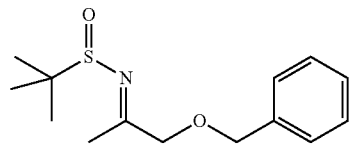 [SMILES: C/C(COCc1ccccc1)=N\S(=O)C(C)(C)C]

To a solution of 1-(benzyloxy)propan-2-one (4.0 g, 21.9 mmol, Eq: 1.00) (CAS 22539-93-1) in dry THF (100 mL) under argon atmosphere was added 2-methylpropane-2-sulfinamide (2.79 g, 23.0 mmol, Eq: 1.05) (CAS 146374-27-8) and Titanium(IV) ethoxide (5.25 g, 4.83 mL, 23.0 mmol, Eq: 1.05). The reaction mixture was stirred at 70° C. overnight. Reaction was cooled down to RT and stirred during quenching by addition of 10 mL of aqueous saturated NaCl solution. The heterogenous mixture was stirred for 20 min, then filtered through a pad of Celite and finally the filtrate was concentrated, diluted with ethyl acetate and extracted with aqueous saturated NaCl solution. Organic phase collected, dried over $Na_2SO_4$ and evaporated down to dryness. Flash chromatography with a 120 g $SiO_2$ column, eluent mixture of heptane and ethyl acetate, gave 2.62 g of the title compound as yellow oil (Yield 45%). MS (ESI, m/z): 268.6 (MH+).

b) N-(1-(benzyloxy)-2-cyanopropan-2-yl)-2-methylpropane-2-sulfinamide

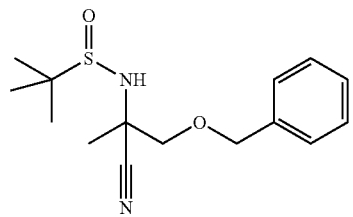 [SMILES: CC(C#N)(COCc1ccccc1)NS(=O)C(C)(C)C]

To a solution of N-(1-(benzyloxy)propan-2-ylidene)-2-methylpropane-2-sulfinamide (2.6 g, 9.72 mmol, Eq: 1.00) in dry THF (45 mL) under argon atmosphere was added CsF (1.62 g, 10.7 mmol, Eq: 1.1) followed by trimethylsilyl cyanide (1.06 g, 1.43 mL, 10.7 mmol, Eq: 1.1). The reaction mixture was stirred at RT overnight and monitored by TLC (ethyl acetate, spray reagent $KMnO_4$). Concentration in vacuo, dilution with ethyl acetate, extraction with water, organic phase was brined before drying over $Na_2SO_4$ and evaporated down to dryness. Flash chromatography with a 70 g $SiO_2$ column, eluent mixture of heptane and ethyl acetate, gave 2.55 g of the desired product (Yield 89%). MS (ESI, m/z): 295.5 (MH+).

c) 3-(benzyloxy)-2-(1,1-dimethylethylsulfinamido)-N'-hydroxy-2-methylpropanimidamide

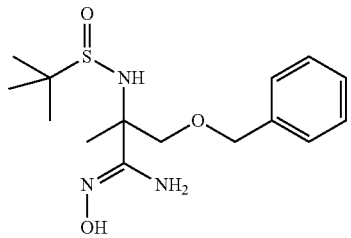 [SMILES: CC(COCc1ccccc1)(NS(=O)C(C)(C)C)/C(N)=N/O]

To a suspension of potassium carbonate (2.44 g, 17.6 mmol, Eq: 1.5) in dry ethanol (40 mL) under argon atmosphere was added hydroxylamine hydrochloride (858 mg, 12.3 mmol, Eq: 1.05) and the mixture was stirred at RT for 20 min. Addition of a solution of N-(1-(benzyloxy)-2-cyanopropan-2-yl)-2-methylpropane-2-sulfinamide (3.46 g, 11.8 mmol, Eq: 1.00) in dry ethanol (30 mL) to the former reaction mixture. The reaction mixture was stirred at 55° C. overnight and monitored by TLC (ethyl acetate, UV 254 nm and spray reagent $KMnO_4$). Evaporation of volatiles, residue suspended in ethyl acetate, extraction with aqueous $Na_2CO_3$ 2M, aqueous phase back-extracted with ethyl acetate, organic phase were combined, dried over $Na_2SO_4$ and evaporated down to dryness. Flash chromatography with a 50 g $SiO_2$ column, eluent mixture of DCM and methanol, gave 3.1 g of the title compound as a white solid (Yield 81%). MS (ESI, m/z): 328.6 (MH+).

d) N-(1-(benzyloxy)-2-(5-methyl-1,2,4-oxadiazol-3-yl)propan-2-yl)-2-methylpropane-2-sulfinamide

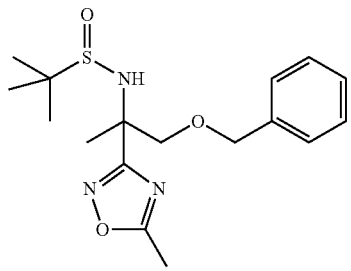 [SMILES: Cc1nc(C(C)(COCc2ccccc2)NS(=O)C(C)(C)C)no1]

To a solution of 3-(benzyloxy)-2-(1,1-dimethylethylsulfinamido)-N'-hydroxy-2-methylpropanimidamide (3.1 g, 9.47 mmol, Eq: 1.00) in dry DMF (50 mL) under argon atmosphere was added potassium carbonate (1.57 g, 11.4 mmol, Eq: 1.2) and acetic anhydride (967 mg, 893 μL, 9.47 mmol, Eq: 1.0). The reaction mixture was stirred at RT for 1 h and was monitored by LC-MS to control the formation of the acetylated intermediate. The reaction was then stirred at 120° C. for 2 h, monitoring was done by LC-MS. Evaporation of volatiles, residue redissolved in ethyl acetate, extraction with aqueous $NaHCO_3$ 1M, aqueous phase back-extracted with ethyl acetate, organic phases were combined, dried over $Na_2SO_4$ and evaporated down to dryness. Flash chromatography with a 120 g $SiO_2$ column, eluent mixture of heptane and ethyl acetate, gave 2.25 g of title compound as yellow oil (Yield 68%). MS (ESI, m/z): 352.6 (MH+).

e) 1-(benzyloxy)-2-(5-methyl-1,2,4-oxadiazol-3-yl)propan-2-amine

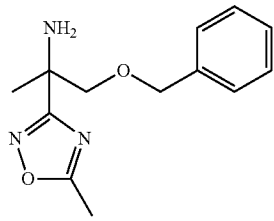 [SMILES: Cc1nc(C(C)(N)COCc2ccccc2)no1]

To a solution of N-(1-(benzyloxy)-2-(5-methyl-1,2,4-oxadiazol-3-yl)propan-2-yl)-2-methylpropane-2-sulfinamide (2.25 g, 6.4 mmol, Eq: 1.00) in MeOH (25 mL) was added HCl 4M in Dioxane (4.8 mL, 19.2 mmol, Eq: 3.0). The reaction mixture was stirred at RT for 1 h and monitored by LC-MS. Evaporation of volatiles, residue redissolved in ethyl acetate, extraction with aqueous Na$_2$CO$_3$ 2M. Aqueous phase was back-extracted with ethyl acetate and organic phases were combined, dried over Na$_2$SO$_4$ and evaporated down to dryness. Flash chromatography with a 50 g SiO$_2$ column, eluent mixture of heptane and ethyl acetate, gave 1.52 g of desired product as light yellow oil (Yield 96%). MS (ESI, m/z): 248.6 (MH+).

f) N-(1-(benzyloxy)-2-(5-methyl-1,2,4-oxadiazol-3-yl)propan-2-yl)-5-cyclopropyl-4-(2,2,2-trifluoroethoxy)picolinamide

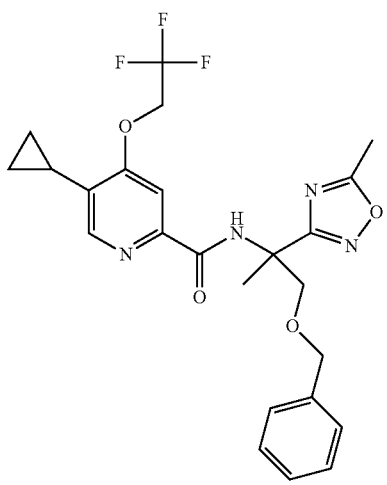 [SMILES: Cc1nc(C(C)(COCc2ccccc2)NC(=O)c2cc(OCC(F)(F)F)c(C3CC3)cn2)no1]

To a solution of 5-cyclopropyl-4-(2,2,2-trifluoroethoxy)picolinic acid (0.4 g, 1.53 mmol, Eq: 1.00), previously described as Example 7e, in dry DMF (10 mL) under argon atmosphere was added TBTU (516 mg, 1.61 mmol, Eq: 1.05) and triethylamine (186 mg, 256 µL, 1.84 mmol, Eq: 1.2). The reaction mixture was stirred at RT for 30 min and 1-(benzyloxy)-2-(5-methyl-1,2,4-oxadiazol-3-yl)propan-2-amine (398 mg, 1.61 mmol, Eq: 1.05) was then added to the reaction. The reaction was then stirred at RT overnight and monitored by LC-MS. Evaporation of DMF. Residue was redissolved in ethyl acetate and extracted with aqueous NaHCO$_3$ 1M. Organic phase dried over Na$_2$SO$_4$ and evaporated down to dryness. Flash chromatography with a 50 g SiO$_2$ column, eluent mixture of heptane and ethyl acetate gave 805 mg of the desired product (Yield 93%). MS (ESI, m/z): 491.5 (MH+).

g) 5-cyclopropyl-N-(1-hydroxy-2-(5-methyl-1,2,4-oxadiazol-3-yl)propan-2-yl)-4-(2,2,2-trifluoroethoxy)picolinamide

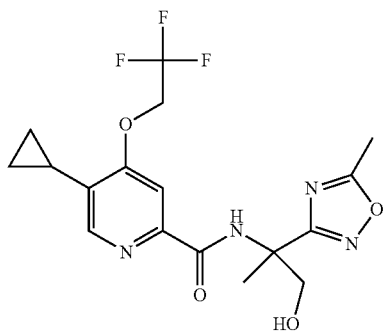 [SMILES: Cc1nc(C(C)(CO)NC(=O)c2cc(OCC(F)(F)F)c(C3CC3)cn2)no1]

To a solution of N-(1-(benzyloxy)-2-(5-methyl-1,2,4-oxadiazol-3-yl)propan-2-yl)-5-cyclopropyl-4-(2,2,2-trifluoroethoxy)picolinamide (0.1 g, 204 µmol, Eq: 1.00) in dry DCM (1 mL) cooled down to 0° C. under argon atmosphere was added BBr$_3$ solution 1.0M in DCM (224 µL, 224 µmol, Eq: 1.1). The reaction mixture was stirred at 0° C. for 15 min and then stirred at RT for 1 h, reaction was monitored by LC-MS. Reaction was diluted with DCM, quenched by addition of aqueous Na$_2$CO$_3$ 2M and mixture was stirred for 10 min. Mixture was poured into a separatory funnel, organic phase was collected, aqueous phase was back-extracted with DCM, organic phases were combined, dried over Na$_2$SO$_4$ and evaporated down to dryness. Flash chromatography with a 10 g SiO$_2$ column, eluent mixture of heptane and ethyl acetate, gave 80 mg of the desired product (Yield 92%). MS (ESI, m/z): 401.5 (MH+).

h) 2-(5-cyclopropyl-4-(2,2,2-trifluoroethoxy)picolinamido)-2-(5-methyl-1,2,4-oxadiazol-3-yl)propyl 4-methylbenzenesulfonate

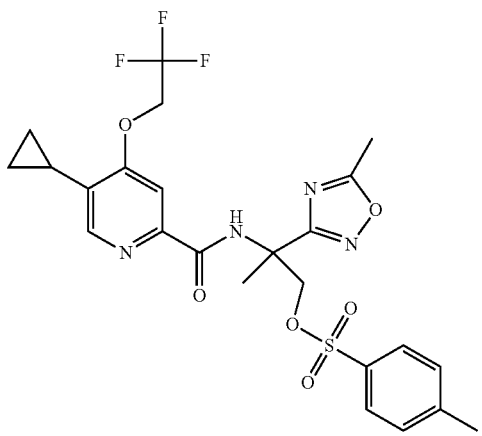 [SMILES: Cc1ccc(S(=O)(=O)OCC(C)(NC(=O)c2cc(OCC(F)(F)F)c(C3CC3)cn2)c2noc(C)n2)cc1]

To a solution of 5-cyclopropyl-N-(1-hydroxy-2-(5-methyl-1,2,4-oxadiazol-3-yl)propan-2-yl)-4-(2,2,2-trifluoroethoxy)picolinamide (0.1 g, 250 µmol, Eq: 1.00) in dry DCM (2 ml) was added DMAP (15.3 mg, 125 µmol, Eq: 0.5), K₂CO₃ (48.3 mg, 350 µmol, Eq: 1.4) followed by addition of 4-methylbenzene-1-sulfonyl chloride (47.6 mg, 250 µmol, Eq: 1.0). The reaction mixture was stirred at RT overnight and monitored by LC-MS. Reaction diluted with DCM and water, poured into a separatory funnel, extracted and organic phase was collected. Organic phase was dried over Na₂SO₄ and evaporated down to dryness. Crude was used for the next step without any purification. MS (ESI, m/z): 555.4 (MH+).

i) 3-(2-(5-cyclopropyl-4-(2,2,2-trifluoroethoxy)pyridin-2-yl)-4-methyl-4,5-dihydrooxazol-4-yl)-5-methyl-1,2,4-oxadiazole

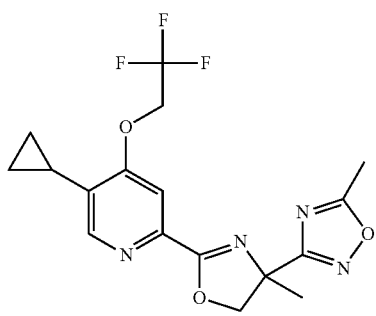 [SMILES: Cc1nc(C2(C)COC(c3cc(OCC(F)(F)F)c(C4CC4)cn3)=N2)no1]

To a solution of 2-(5-cyclopropyl-4-(2,2,2-trifluoroethoxy)picolinamido)-2-(5-methyl-1,2,4-oxadiazol-3-yl)propyl 4-methylbenzenesulfonate (0.06 g, 108 µmol, Eq: 1.00) in dry DMF (1 mL) was added triethylamine (16.4 mg, 22.6 µl, 162 µmol, Eq: 1.5) and 3,3-difluoroazetidine hydrochloride (CAS 288315-03-7) (16.8 mg, 130 µmol, Eq: 1.2). The reaction mixture was stirred at 80° C. for 45 min under microwave radiation and reaction was monitored by LC-MS which showed conversion to a side product from an intramolecular ring closure to an oxazolidine. Reaction was directly purified by preparative HPLC without any purification and gave 6.2 mg of the title compound. MS (ESI, m/z): 383.5 (MH+).

Example 112

5-tert-butyl-3-(6-chloro-5-cyclopropyl-4-(4-fluorobenzyloxy)pyridin-2-yl)-1,2,4-oxadiazole a) 2-(5-tert-butyl-1,2,4-oxadiazol-3-yl)-5-cyclopropyl-4-(4-fluorobenzyloxy)pyridine 1-oxide

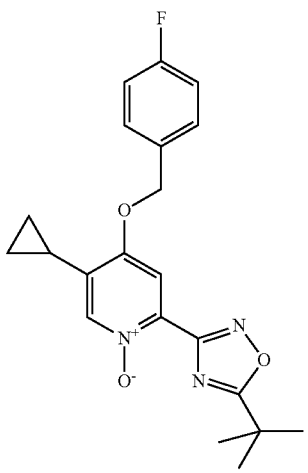 [SMILES: CC(C)(C)c1nc(-c2cc(OCc3ccc(F)cc3)c(C3CC3)c[n+]2[O-])no1]

To a solution of 5-tert-butyl-3-(5-cyclopropyl-4-(4-fluorobenzyloxy)pyridin-2-yl)-1,2,4-oxadiazole (326 mg, 887 µmol, Eq: 1.00), previously described as Example 53, in dry DCM (4.93 mL) was added m-CPBA (459 mg, 1.33 mmol, Eq: 1.5) and the reaction stirred overnight at RT. Extraction with NaHCO₃/DCM. Organic layer was dried on Na₂SO₄ and evaporated. Purification by flash chromatography on SiO₂ column with a gradient DCM and methanol gave 445 mg of the title compound (Yield 78%). MS (ESI, m/z): 384.6 (MH+).

b) 5-tert-butyl-3-(6-chloro-5-cyclopropyl-4-(4-fluorobenzyloxy)pyridin-2-yl)-1,2,4-oxadiazole

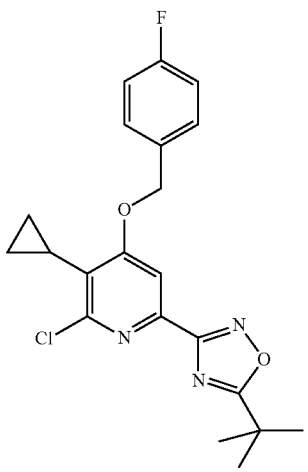 [SMILES: CC(C)(C)c1nc(-c2cc(OCc3ccc(F)cc3)c(C3CC3)c(Cl)n2)no1]

2-(5-tert-butyl-1,2,4-oxadiazol-3-yl)-5-cyclopropyl-4-(4-fluorobenzyloxy)pyridine 1-oxide (123 mg, 321 µmol, Eq: 1.00) was dissolved in a mixture of DCM/DMF: 1/1 (2.8 mL). The mixture was cooled down to 0° C. and oxalyl chloride (204 mg, 139 μL, 1.6 mmol, Eq: 5.0) was slowly added. Reaction was stirred at 0° C. for 30 min and then the temperature was allowed to reach RT and reacted overnight. The reaction was cooled down to 0° C. and quenched by in addition of aqueous Na$_2$CO$_3$ and stirred for 15 min at 0° C. The mixture was diluted with ethyl acetate and extracted with aqueous Na$_2$CO$_3$. Organic phase was collected; aqueous phase was back-extracted with ethyl acetate. Organic phases were combined, dried over Na$_2$SO$_4$ and evaporated down to dryness. The crude material was purified by flash chromatography on SiO$_2$ using MPLC ISCO with a gradient heptane/ethyl acetate giving 15 mg of the title compound as colorless viscous oil. MS (ESI, m/z): 402.5 (MH+).

Example 113

2-tert-butyl-5-[5-cyclopropyl-4-(2,2,2-trifluoroethoxy)pyridin-2-yl]-1,3,4-oxadiazole a) 5-cyclopropyl-N'-pivaloyl-4-(2,2,2-trifluoroethoxy)picolinohydrazide

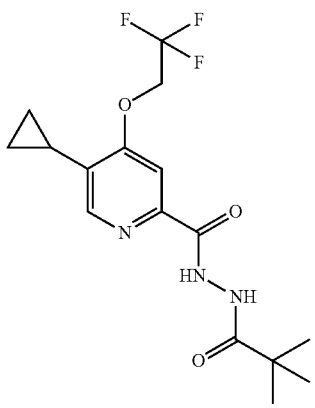 [SMILES: CC(C)(C)C(=O)NNC(=O)c1cc(OCC(F)(F)F)c(C2CC2)cn1]

5-cyclopropyl-4-(2,2,2-trifluoroethoxy)picolinic acid (100 mg, 383 mmol, Eq: 1.00), previously described as Example 7e, in DCM (1.91 mL) had oxalyl chloride (50 μL, 0.574 mmol, Eq: 1.5) and DMF (2 μL, 0.019 mmol, Eq: 0.05) added to it. The reaction was deemed to be complete and the reaction mixture was concentrated in vacuo. The product was used immediately in the next step and dissolved in THF (563 μL) to be reacted with pivalohydrazide (55.0 mg, 459 μmol, Eq: 1.2) (CAS 42826-42-6) and triethylamine (58.1 mg, 80.0 μL, 574 μmol, Eq: 1.5) at RT overnight. The reaction mixture was then diluted with ethyl acetate, poured into NaHCO$_3$ 1M solution. It was then extracted with ethyl acetate and the organic layers were combined, dried, and concentrated in vacuo to give 130 mg of the title compound used as crude (Yield 94%). MS (ESI, m/z): 360.6 (MH+).

b) 2-tert-butyl-5-[5-cyclopropyl-4-(2,2,2-trifluoroethoxy)pyridin-2-yl]-1,3,4-oxadiazole

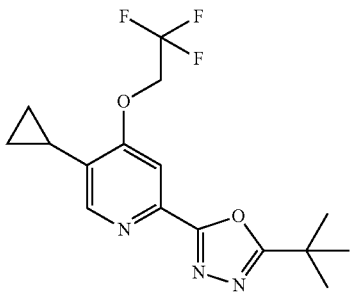 [SMILES: CC(C)(C)c1nnc(-c2cc(OCC(F)(F)F)c(C3CC3)cn2)o1]

Trifluoromethanesulfonic anhydride (153 mg, 91.7 μL, 543 μmol, Eq: 1.5) was added slowly to a solution of triphenylphosphine oxide (302 mg, 1.09 mmol, Eq: 3.0) in dry DCM (0.231 mL) at 0° C. The reaction mixture was stirred for 5 minutes at this temperature before it was adjusted to room temperature and 5-cyclopropyl-N'-pivaloyl-4-(2,2,2-trifluoroethoxy)picolinohydrazide (130 mg, 362 μmol, eq: 1.00) previously azeotropically dried with toluene, was added. The reaction mixture was then stirred for a further 30 minutes at RT before monitoring via LC-MS showed the reaction as complete. The reaction mixture was then diluted with DCM and poured into NaHCO$_3$ saturated aqueous solution and extracted with DCM. The aqueous layer was then back-extracted with DCM before the organic layers were combined, dried, and concentrated in vacuo. The crude material was purified by flash chromatography (SiO$_2$, 10 g, gradient ethyl acetate in heptane) to give 56 mg of the title product as white solid (45% yield). MS (ESI, m/z): 342.6 (MH+).

Example 114

5-tert-butyl-3-[6-chloro-5-cyclopropyl-4-(oxan-4-yloxy)pyridin-2-yl]-1,2,4-oxadiazole a) 2-(5-tert-butyl-1,2,4-oxadiazol-3-yl)-5-cyclopropyl-4-(tetrahydro-2H-pyran-4-yloxy)pyridine 1-oxide

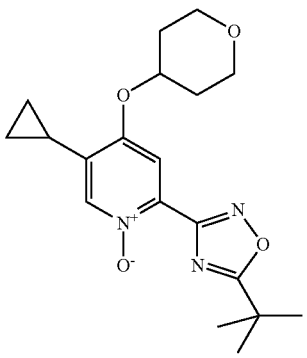 [SMILES: CC(C)(C)c1nc(-c2cc(OC3CCOCC3)c(C3CC3)c[n+]2[O-])no1]

To a solution of 5-tert-butyl-3-(5-cyclopropyl-4-(tetrahydro-2H-pyran-4-yloxy)pyridin-2-yl)-1,2,4-oxadiazole (64 mg, 186 μmol, Eq: 1.00), previously described as Example 63, in dry DCM (1.04 mL) was added m-CPBA (96.5 mg, 280 µmol, Eq: 1.5). The reaction was stirred for 1 h at RT. Extraction NaHCO₃/DCM. Organic layer was dried on Na₂SO₄ and evaporated. Purification by flash chromatography (SiO₂, 70 g, eluent: ethyl acetate/heptane) gave 59 mg of the desired compound (Yield 88%). MS (ESI, m/z): 360.6 (MH+).

b) 5-tert-butyl-3-[6-chloro-5-cyclopropyl-4-(oxan-4-yloxy)pyridin-2-yl]-1,2,4-oxadiazole

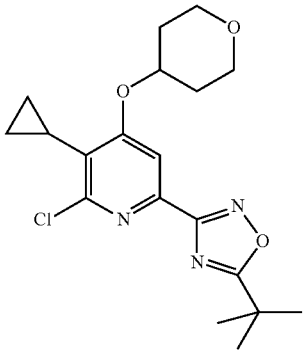 [SMILES: CC(C)(C)c1nc(-c2cc(OC3CCOCC3)c(C3CC3)c(Cl)n2)no1]

2-(5-tert-butyl-1,2,4-oxadiazol-3-yl)-5-cyclopropyl-4-(tetrahydro-2H-pyran-4-yloxy)pyridine 1-oxide (56 mg, 0.156 mmol, Eq: 1.00) was dissolved in a mixture of DCM/DMF: 1/1 (1.3 mL). The mixture was cooled down to 0° C. and oxalyl chloride (98.9 mg, 67.3 µL, 779 µmol, Eq: 5.0) was slowly added. Reaction was stirred at 0° C. for 20 min and then the temperature was allowed to reach RT and reacted overnight. Another 1.5 eq of oxalyl chloride was added and stirred for 1.5 h. The reaction was then cooled down to 0° C. and quenched by addition of aqueous Na₂CO₃ and stirred for 15 min at 0° C. The mixture was diluted with ethyl acetate and extracted with aqueous Na₂CO₃. Organic phase was collected; aqueous phase was back-extracted with ethyl acetate. Organic phases were combined, dried over Na₂SO₄ and evaporated down to dryness. The crude material was purified by flash chromatography (SiO₂, 5 g, ethyl acetate/heptane) giving 21 mg of the title compound as colorless oil (Yield 35%). MS (ESI, m/z): 378.5 (MH+).

Example 115

5-tert-butyl-3-[5-cyclopropyl-4-(2,2-difluoroethoxy)pyridin-2-yl]-1,2,4-oxadiazole a) 5-cyclopropyl-4-(2,2-difluoroethoxy)picolinonitrile

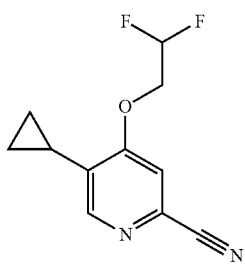 [SMILES: N#Cc1cc(OCC(F)F)c(C2CC2)cn1]

Sodium hydride (123 mg, 3.08 mmol, Eq: 1.1) was added to a solution of 4-chloro-5-cyclopropylpicolinonitrile (500 mg, 2.8 mmol, Eq: 1.00), previously described as Example 48b, and 2,2-difluoroethanol (253 mg, 3.08 mmol, Eq: 1.1) (CAS 359-13-7) in DMF (10 mL) at RT. and stirred for 3 hours. The 5-fold volume of water was added, followed by extraction with EtOAc, washing with brine. Organic layer was dried on MgSO₄, concentrated in vacuo and chromatographied on SiO₂ with DCM to afford 508 mg of the title compound as a dark-yellow solid (Yield 80%). MS (ESI, m/z): 225.2 (MH+).

b) 5-tert-butyl-3-[5-cyclopropyl-4-(2,2-difluoroethoxy)pyridin-2-yl]-1,2,4-oxadiazole

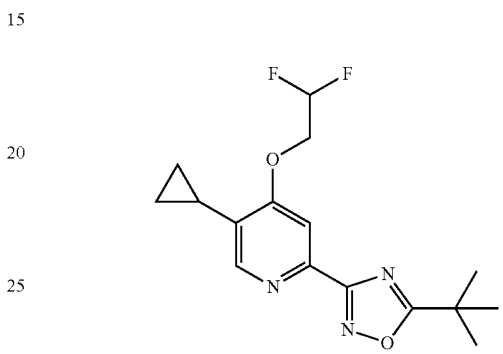

To a solution of 5-cyclopropyl-4-(2,2-difluoroethoxy)picolinonitrile (120 mg, 0.535 mmol, Eq: 1.00) in EtOH (3.5 mL) was added triethylamine (149 µL, 1.07 mmol, Eq: 2.0) and hydroxylamine hydrochloride (55.8 mg, 0.803 mmol, Eq: 1.5) and the mixture heated 30 min at 90° C. with microwave. 1 M NaHCO₃ was added and it was extracted with DCM. Drying on MgSO₄ and concentration in vacuo afforded 60 mg of the compound as light-yellow solid, this was used without further purification and dissolved in DMF (2.00 mL). Then triethylamine (29.0 mg, 40.0 µL, 287 µmol, Eq: 1.2) and pivaloyl chloride (31.4 mg, 32 µL, 260 µmol, Eq: 1.1) were added at RT and after 30 minutes stirring, the solution was heated at 130° C. with microwave for 30 minutes. The mixture was diluted with water and extracted with ethyl acetate, washed with brine, dried on MgSO₄ and concentration in vacuo followed by column chromatography (SiO₂, ethyl acetate in heptane) afforded 45 mg of the title compound (Yield 59%). MS (ESI, m/z): 324.5 (MH+).

Example 116

5-tert-butyl-3-[5-cyclopropyl-4-(2-fluoroethoxy)pyridin-2-yl]-1,2,4-oxadiazole

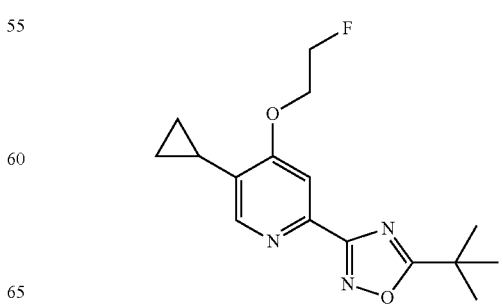

The title compound was synthesized in analogy to Example 115, using 4-chloro-5-cyclopropylpicolinonitrile, previously described as Example 48b, and 2-fluoroethanol (CAS 371-62-0) as starting materials. MS (ESI, m/z): 306.5 (MH+).

Example 117

5-tert-butyl-3-[5-cyclopropyl-4-(pyridin-2-yl-methoxy)pyridin-2-yl]-1,2,4-oxadiazole

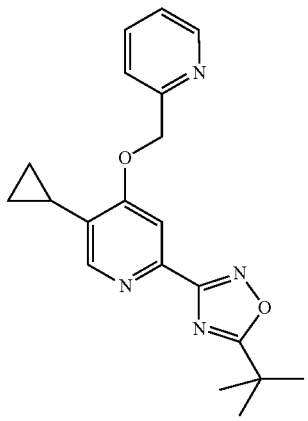 [SMILES: CC(C)(C)c1nc(-c2cc(OCc3ccccn3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and 2-(hydroxymethyl)pyridine (CAS 586-98-1) as starting materials, heated 30 min at 120° C. with microwave and purified by preparative HPLC without any work-up. MS (ESI, m/z): 351.6 (MH+).

Example 118

5-tert-butyl-3-[5-cyclopropyl-4-[(5-fluoropyridin-2-yl)methoxy]pyridin-2-yl]-1,2,4-oxadiazole

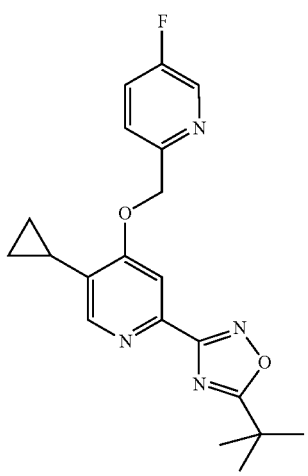 [SMILES: CC(C)(C)c1nc(-c2cc(OCc3ccc(F)cn3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and 5-fluoro-2-hydroxylmethylpyridine (CAS 802325-29-7) as starting materials, heated 30 min at 110° C. under microwave radiation. The mixture was diluted with ethyl acetate and extracted with aqueous Na$_2$CO$_3$. Organic phase was collected and the aqueous phase was back-extracted with ethyl acetate. The organic phases were combined, dried over Na$_2$SO$_4$ and evaporated down to dryness. The crude material was purified by flash chromatography (SiO$_2$, 5 g, ethyl acetate/heptane). MS (ESI, m/z): 369.6 (MH+).

Example 119

5-tert-butyl-3-[5-cyclopropyl-4-(pyridin-3-yl-methoxy)pyridin-2-yl]-1,2,4-oxadiazole

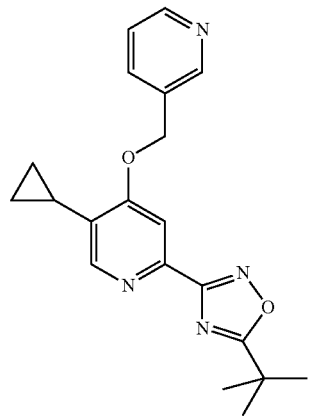 [SMILES: CC(C)(C)c1nc(-c2cc(OCc3cccnc3)c(C3CC3)cn2)no1]

The title compound was synthesized in analogy to Example 48e, using 5-tert-butyl-3-(4-chloro-5-cyclopropylpyridin-2-yl)-1,2,4-oxadiazole and 3-(hydroxymethyl)pyridine (CAS 100-55-0) as starting materials, heated 30 min at 110° C. under microwave radiation. The mixture was diluted with ethyl acetate and extracted with aqueous Na$_2$CO$_3$. The organic phase was collected and the aqueous phase was back-extracted with ethyl acetate. The organic phases were combined, dried over Na$_2$SO$_4$ and evaporated down to dryness. The crude material was purified by flash chromatography (SiO$_2$, 5 g, ethyl acetate/heptane). MS (ESI, m/z): 351.6 (MH+).

Example 120

2-tert-butyl-5-[5-cyclopropyl-4-[(2S)-1,1,1-trifluoropropan-2-yl]oxypyridin-2-yl]-1,3,4-oxadiazole

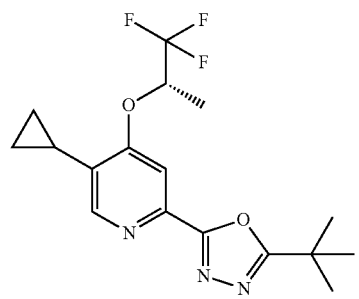 [SMILES: C[C@H](Oc1cc(-c2nnc(C(C)(C)C)o2)ncc1C1CC1)C(F)(F)F]

The title compound was synthesized in a similar manner to Example 98, using the corresponding nitrile 5-cyclopropyl-4-((S)-2,2,2-trifluoro-1-methyl-ethoxy)-pyridine-2-carbonitrile generated from (S)-1,1,1-Trifluoropropan-2-ol (CAS 3539-97-7) according to example 7a-d. MS (ESI, m/z): 356.6 (MH+).

Example 121

3-tert-butyl-5-(5-cyclopropyl-4-(tetrahydro-2H-pyran-4-yloxy)pyridin-2-yl)-1,2,4-oxadiazole

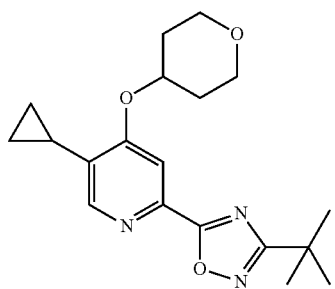 [SMILES: CC(C)(C)c1noc(-c2cc(OC3CCOCC3)c(C3CC3)cn2)n1]

The title compound was synthesized in analogy to Example 51c, using 5-cyclopropyl-4-(tetrahydro-2H-pyran-4-yloxy)picolinic acid from example 98b. MS (ESI, m/z): 344.5 (MH+).

Example 122

3-tert-butyl-5-[5-cyclopropyl-4-[[(2S)-1-methylpyrrolidin-2-yl]methoxy]pyridin-2-yl]-1,2,4-oxadiazole a) tert-butyl (2S)-2-[[2-(3-tert-butyl-1,2,4-oxadiazol-5-yl)-5-cyclopropylpyridin-4-yl]oxymethyl]pyrrolidine-1-carboxylate

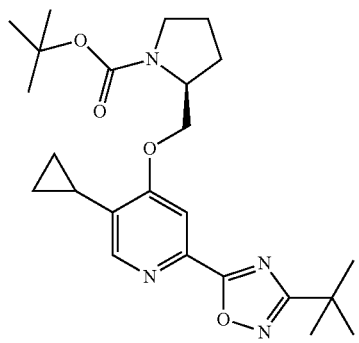 [SMILES: CC(C)(C)OC(=O)N1CCC[C@H]1COc1cc(-c2nc(C(C)(C)C)no2)ncc1C1CC1]

The title compound was synthesized in analogy to Example 51d using Boc-L-prolinol (CAS 69610-40-8). MS (ESI, m/z): 443.7 (MH+).

b) 3-tert-butyl-5-[5-cyclopropyl-4-[[(2S)-pyrrolidin-2-yl]methoxy]pyridin-2-yl]-1,2,4-oxadiazole

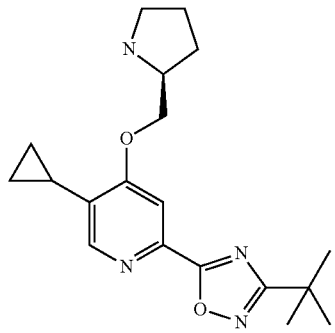 [SMILES: CC(C)(C)c1noc(-c2cc(OC[C@@H]3CCCN3)c(C3CC3)cn2)n1]

tert-butyl (2S)-2-[[2-(3-tert-butyl-1,2,4-oxadiazol-5-yl)-5-cyclopropylpyridin-4-yl]oxymethyl]pyrrolidine-1-carboxylate (364 mg, 823 µmol, Eq: 1.00) was dissolved in a 4M solution of hydrochloric acid in 1,4-dioxane (19.5 ml, 78.1 mmol, Eq: 95) and then stirred at rt for 1.5 hours and monitored by LC-MS. The solvent was evaporated and the reaction mixture was diluted with ethyl acetate and washed with NaHCO3 and the organic phase was collected, dried over Na₂SO₄ and evaporated. The crude material was purified by flash chromatography (SiO₂, 20 g, ethyl acetate/heptane) to afford 104 mg of the title compound as a light yellow powder (Yield 37%). MS (ESI, m/z): 343.6 (MH+).

c) 3-tert-butyl-5-[5-cyclopropyl-4-[[(2S)-1-methyl-pyrrolidin-2-yl]methoxy]pyridin-2-yl]-1,2,4-oxadiazole

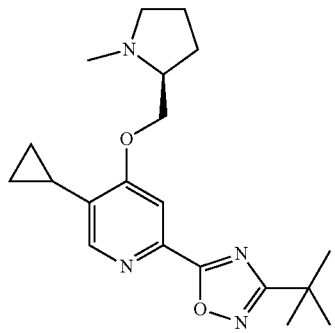 [SMILES: CN1CCC[C@H]1COc1cc(-c2nc(C(C)(C)C)no2)ncc1C1CC1]

To a solution of 3-tert-butyl-5-[5-cyclopropyl-4-[[(2S)-pyrrolidin-2-yl]methoxy]pyridin-2-yl]-1,2,4-oxadiazole (95 mg, 277 µmol, Eq: 1.00) and formaldehyde (295 mg, 360 µl, 3.63 mmol, Eq: 13.1) in dichloromethane (1.8 mL) was added sodium triacetoxyborohydride (300 mg, 1.42 mmol, Eq: 5.1). The reaction was stirred 3 hours at rt, and monitored by LC-MS. The mixture was diluted with dichloromethane and washed with 1 N NaOH. The organic phase was dried over Na₂SO₄ and evaporated. The crude material was purified by flash chromatography (SiO₂, 10 g, ethyl acetate/heptane) to afford 54 mg of the title compound as light yellow oil (Yield 54%). MS (ESI, m/z): 357.6 (MH+).

Example 123

3-tert-butyl-5-(5-cyclopropyl-4-(2,2-difluoroethoxy)pyridin-2-yl)-1,2,4-oxadiazole a) 5-cyclopropyl-4-(2,2-difluoroethoxy)picolinic acid 5-cyclopropyl-4-(2,2-difluoroethoxy)picolinonitrile (350 mg, 1.56 mmol, Eq: 1.00, previously described as Example 115a, was dissolved in aqueous HCl 25% (16.8 g, 15 ml, 115 mmol, Eq: 73.8). Reaction was heated at 110° C. for 1 hour and then cooled down to rt. HCl was neutralized using 6M NaOH aq. sol. Then pH adjusted to 1-2 with HCl 2M. The precipitate formed was then filtered. The remaining salt was precipitated with ethanol and filtered giving the title compound as a light yellow solid. MS (ESI, m/z): 244.3 (MH+).

b) 3-tert-butyl-5-(5-cyclopropyl-4-(2,2-difluoroethoxy)pyridin-2-yl)-1,2,4-oxadiazole

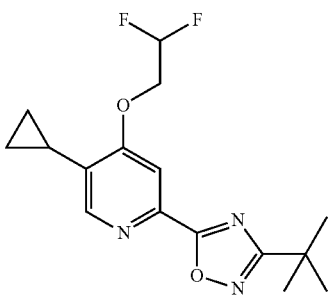 [SMILES: CC(C)(C)c1noc(-c2cc(OCC(F)F)c(C3CC3)cn2)n1]

The title compound was synthesized in analogy to Example 51c, using 5-cyclopropyl-4-(2,2-difluoroethoxy)picolinic acid. MS (ESI, m/z): 324.6 (MH+).

Example 124

Pharmacological Tests

The following tests were carried out in order to determine the activity of the compounds of formula I:

Radioligand Binding Assay

The affinity of the compounds of the invention for cannabinoid CB1 receptors was determined using recommended amounts of membrane preparations (PerkinElmer) of human embryonic kidney (HEK) cells expressing the human CNR1 or CNR2 receptors in conjunction with 1.5 or 2.6 nM [3H]-CP-55,940 (Perkin Elmer) as radioligand, respectively. Binding was performed in binding buffer (50 mM Tris, 5 mM MgCl2, 2.5 mM EDTA, and 0.5% (wt/vol) fatty acid free BSA, pH 7.4 for CB1 receptor and 50 mM Tris, 5 mM $MgCl_2$, 2.5 mM EGTA, and 0.1% (wt/vol) fatty acid free BSA, pH 7.4 for CB2 receptor) in a total volume of 0.2 ml for 1 h at 30° C. shaking. The reaction was terminated by rapid filtration through microfiltration plates coated with 0.5% polyethylenimine (UniFilter GF/B filter plate; Packard). Bound radioactivity was analyzed for Ki using nonlinear regression analysis (Activity Base, ID Business Solution, Limited), with the Kd values for [3H]CP55,940 determined from saturation experiments. The compounds of formula (I) show an excellent affinity for the CB2 receptor with affinities below 10 µM, more particularly of 1 nM to 3 µM and most particularly of 1 nM to 100 nM.

cAMP Assay

CHO cells expressing human CB1 or CB2 receptors are seeded 17-24 hours prior to the experiment 50.000 cells per well in a black 96 well plate with flat clear bottom (Corning Costar #3904) in DMEM (Invitrogen No. 31331), 1×HT supplement, with 10% fetal calf serum and incubated at 5% $CO_2$ and 37° C. in a humidified incubator. The growth medium was exchanged with Krebs Ringer Bicarbonate buffer with 1 mM IBMX and incubated at 30° C. for 30 min. Compounds were added to a final assay volume of 100 µl and incubated for 30 min at 30° C. Using the cAMP-Nano-TRF detection kit the assay (Roche Diagnostics) was stopped by the addition of 50 µl lysis reagent (Tris, NaCl, 1.5% Triton X100, 2.5% NP40, 10% $NaN_3$) and 50 µl detection solutions (20 µM mAb Alexa700-cAMP 1:1, and 48 µM Ruthenium-2-AHA-cAMP) and shaken for 2 h at room temperature. The time-resolved energy transfer is measured by a TRF reader (Evotec Technologies GmbH), equipped with a ND:YAG laser as excitation source. The plate is measured twice with the excitation at 355 nm and at the emission with a delay of 100 ns and a gate of 100 ns, total exposure time 10 s at 730 (bandwidth30 nm) or 645 nm (bandwidth 75 nm), respectively. The FRET signal is calculated as follows: FRET=T730-Alexa730-P(T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 µM to 0.13 nM cAMP.

$EC_{50}$ values were determined using Activity Base analysis (ID Business Solution, Limited). The $EC_{50}$ values for a wide range of cannabinoid agonists generated from this assay were in agreement with the values published in the scientific literature.

The compounds of the invention are CB2 agonists with $EC_{50}$ below 0.5 µM and selectivity versus CB1 in the corresponding assay of at least 10 fold. Particular compound of the invention are CB2 agonists with $EC_{50}$ below 0.05 µM and selectivity versus CB1 in the corresponding assay of at least 500 fold.

For example, the following compounds showed the following human $EC_{50}$ values in the functional cAMP assay described above (in µM):

| Example | EC50 CB2 human | EC50 CB1 human |
|---|---|---|
| 1 | 0.0257 | >10 |
| 2 | 0.0231 | >10 |
| 3 | 0.0012 | >10 |
| 4 | 0.0021 | >10 |
| 5 | 0.0691 | >10 |
| 6 | 0.001 | 0.0092 |
| 7 | 0.0111 | >10 |
| 8 | 0.0213 | >10 |
| 9 | 0.0158 | >10 |
| 10 | 0.0008 | >10 |
| 11 | 0.0006 | >10 |
| 12 | 0.0466 | >10 |
| 13 | 0.0319 | >10 |
| 14 | 0.0037 | >10 |
| 15 | 0.0198 | >10 |
| 16 | 0.3426 | >10 |
| 17 | 0.0205 | >10 |
| 18 | 0.1104 | >10 |
| 19 | 0.0137 | >10 |
| 20 | 0.0037 | >10 |
| 21 | 0.07 | >10 |

| Example | EC50 CB2 human | EC50 CB1 human |
| --- | --- | --- |
| 22 | 0.0042 | 3.67542 |
| 23 | 0.0352 | >10 |
| 24 | 0.0043 | 0.58087 |
| 25 | 0.135 | >10 |
| 26 | 0.0308 | >10 |
| 27 | 0.0035 | >10 |
| 28 | 0.016 | >10 |
| 29 | 0.7967 | >10 |
| 30 | 0.0026 | >10 |
| 31 | 0.0194 | >10 |
| 32 | 0.0086 | >10 |
| 33 | 0.0069 | >10 |
| 34 | 0.0147 | >10 |
| 35 | 0.0328 | >10 |
| 36 | 0.0209 | >10 |
| 37 | 0.2359 | >10 |
| 38 | 0.1283 | >10 |
| 39 | 0.4344 | >10 |
| 40 | 0.0022 | >10 |
| 41 | 0.0539 | >10 |
| 42 | 0.0023 | >10 |
| 43 | 0.0409 | >10 |
| 44 | 0.0159 | >10 |
| 45 | 0.0778 | >10 |
| 46 | 0.1798 | >10 |
| 47 | 0.1659 | >10 |
| 48 | 0.019 | >10 |
| 49 | 0.0515 | >10 |
| 50 | 0.0458 | >10 |
| 51 | 0.0618 | >10 |
| 52 | 0.0131 | >10 |
| 53 | 0.0014 | 0.05506 |
| 54 | 0.0331 | >10 |
| 55 | 0.0077 | >10 |
| 56 | 0.0447 | >10 |
| 57 | 0.0134 | >10 |
| 58 | 0.0156 | >10 |
| 59 | 0.0481 | >10 |
| 60 | 0.4476 | >10 |
| 61 | 0.0062 | >10 |
| 62 | 0.0178 | >10 |
| 63 | 0.0043 | >10 |
| 64 | 0.0875 | >10 |
| 65 | 0.0017 | 0.17031 |
| 66 | 0.009 | >10 |
| 67 | 0.4343 | >10 |
| 68 | 0.0726 | >10 |
| 69 | 0.009 | >10 |
| 70 | 0.0057 | >10 |
| 71 | 0.2795 | >10 |
| 72 | 0.0454 | >10 |
| 73 | 0.0572 | >10 |
| 74 | 0.0047 | >10 |
| 75 | 0.2877 | >10 |
| 76 | 0.0193 | >10 |
| 77 | 0.0021 | >10 |
| 78 | 0.0422 | >10 |
| 79 | 0.009 | >10 |
| 80 | 0.0475 | >10 |
| 81 | 0.0211 | >10 |
| 82 | 0.0379 | >10 |
| 83 | 0.0301 | >10 |
| 84 | 0.0501 | >10 |
| 85 | 0.0356 | 1.33751 |
| 86 | 0.0482 | 1.40191 |
| 87 | 0.1127 | >10 |
| 88 | 0.0529 | >10 |
| 89 | 0.0162 | >10 |
| 90 | 0.0118 | >10 |
| 91 | 0.6412 | >10 |
| 92 | 0.0751 | 0.76771 |
| 93 | 0.0119 | 0.23504 |
| 94 | 0.0602 | >10 |
| 95 | 0.0261 | >10 |
| 96 | 0.0759 | 1.01189 |
| 97 | 0.019 | >10 |
| 98 | 0.042 | >10 |
| 99 | 0.3174 | >10 |
| 100 | 0.5179 | >10 |
| 101 | 0.1423 | >10 |
| 102 | 0.0718 | >10 |
| 103 | 0.0289 | >10 |
| 104 | 0.0698 | >10 |
| 105 | 0.0291 | >10 |
| 106 | 0.1279 | >10 |
| 107 | 0.0958 | >10 |
| 108 | 0.0698 | >10 |
| 109 | 0.162 | >10 |
| 110 | 0.103 | >10 |
| 111 | 0.0576 | >10 |
| 112 | 0.0048 | 0.07317 |
| 113 | 0.0225 | >10 |
| 114 | 0.0037 | 0.45539 |
| 115 | 0.002 | >10 |
| 116 | 0.0155 | >10 |
| 117 | 0.0539 | >10 |
| 118 | 0.035 | >10 |
| 119 | 0.047 | >10 |
| 120 | 0.063 | >10 |
| 121 | 0.001 | >10 |
| 122 | 0.146 | >10 |
| 123 | 0.002 | >10 |

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:
1. A compound selected from the group consisting of:
5-[5-cyclopropyl-4-(cyclopropylmethoxy)pyridin-2-yl]-3-methyl-1,2,4-oxadiazole;
5[5-cyclopropyl-4-(cyclopropylmethoxy)pyridin-2-yl]-3-phenyl-1,2,4-oxadiazole;
3-cyclopropyl-5-[5-cyclopropyl-4-(cyclopropylmethoxy)pyridin-2-yl]-1,2,4-oxadiazole;
3-cyclopentyl-5-[5-cyclopropyl-4-(cyclopropylmethoxy)pyridin-2-yl]-1,2,4-oxadiazole;
3-benzyl-5-[5-cyclopropyl-4-(cyclopropylmethoxy)pyridin-2-yl]1,2,4-oxadiazole;
3-tert-butyl-5-[5-cyclopropyl-4-(cyclopropylmethoxy)pyridin-2-yl]-1,2,4-oxadiazole;
3-cyclopropyl-5-[5-cyclopropyl-4-(2,2,2-trifluoroethoxy)pyridin-2-yl]-1,2,4-oxadiazole;
5-[5-cyclopropyl-4-(2,2,2-trifluoroethoxy)pyridin-2-yl]-3-(trifluoromethyl)-1,2,4-oxadiazole;
5-cyclopropyl-3-[5-cyclopropyl-4-(cyclopropylmethoxy)pyridin-2-yl]-1,2,4-oxadiazole;
5-tert-butyl-3-[5-cyclopropyl-4-(cyclopropylmethoxy)pyridin-2-yl]-1,2,4-oxadiazole;
3-[5-cyclopropyl-4-(cyclopropylmethoxy)pyridin-2-yl]-5-(methoxymethyl)-1,2,4-oxadiazole;
3-[5-cyclopropyl-4-(cyclopropylmethoxy)pyridin-2-yl]-5-ethyl-1,2,4-oxadiazole;
3-[5-cyclopropyl-4-(cyclopropylmethoxy)pyridin-2-yl]-5-propan-2-yl-1,2,4-oxadiazole;
[3-[5-cyclopropyl-4-(cyclopropylmethoxy)pyridin-2-yl]-1,2,4-oxadiazol-5-yl]methanol;
3-[5-cyclopropyl-4-(cyclopropylmethoxy)pyridin-2-yl]-5-(trifluoromethyl)-1,2,4-oxadiazole;
1-[3-[5-cyclopropyl-4-(cyclopropylmethoxy)pyridin-2-yl]-1,2,4-oxadiazol-5-yl]cyclopropan-1-ol;
3-[5-cyclopropyl-4-(cyclopropylmethoxy)pyridin-2-yl]-5-(1-methylcyclopropyl)-1,2,4-oxadiazole;
1-[3-[5-cyclopropyl-4-(cyclopropylmethoxy)pyridin-2-yl]-1,2,4-oxadiazol-5-yl]cyclopropane-1-carboxamide;
2-[3-[5-cyclopropyl-4-(cyclopropylmethoxy)pyridin-2-yl]-1,2,4-oxadiazol-5-yl]propan-2-ol;
5-tert-butyl-3-[5-cyclopropyl-4-(2,2,2-trifluoroethoxy)pyridin-2-yl]-1,2,4-oxadiazole;
3-[5-cyclopropyl-4-(2,2,2-trifluoroethoxy)pyridin-2-yl]-5-(1-methylcyclopropyl)-1,2,4-oxadiazole;
3-[5-cyclopropyl-4-(2,2,2-trifluoroethoxy)pyridin-2-yl]-5-propan-2-yl-1,2,4-oxadiazole;
1-[3-[5-cyclopropyl-4-(2,2,2-trifluoroethoxy)pyridin-2-yl]-1,2,4-oxadiazol-5-yl]cyclopropan-1-ol;
3-[5-cyclopropyl-4-(2,2,2-trifluoroethoxy)pyridin-2-yl]-1,2,4-oxadiazole;
3-tert-butyl-5-[5-cyclopropyl-4-(2,2,2-trifluoroethoxy)pyridin-2-yl]-1,2,4-oxadiazole;
5-[5-cyclopropyl-4-(2,2,2-trifluoroethoxy)pyridin-2-yl]-3-propan-2-yl-1,2,4-oxadiazole;
5-tert-butyl-3-[4-(cyclopropylmethoxy)-5-methylsulfonylpyridin-2-yl]-1,2,4-oxadiazole;
5-tert-butyl-3-[5-cyclopropyl-4-[(2S)-1,1,1-trifluoropropan-2-yl]oxypyridin-2-yl]-1,2,4-oxadiazole;
5-tert-butyl-3-[5-cyclopropyl-4-[(2R)-1,1,1-trifluoropropan-2-yl]oxypyridin-2-yl]-1,2,4-oxadiazole;
3-tert-butyl-5-[5-cyclopropyl-4-[(2R)-1,1,1-trifluoropropan-2-yl]oxypyridin-2-yl]-1,2,4-oxadiazole;
3-tert-butyl-5-[5-cyclopropyl-4-[(2S)-1,1,1-trifluoropropan-2-yl]oxypyridin-2-yl]-1,2,4-oxadiazole;
5-tert-butyl-3[5-cyclopropyl-4-[(4-fluorophenyl)methoxy]pyridin-2-yl]-1,2,4-oxadiazole;
5-tert-butyl-3-[5-cyclopropyl-4-[(3-methyloxetan-3-yl)methoxy]pyridin-2-yl]-1,2,4-oxadiazole;
5-tert-butyl-3-[5-cyclopropyl-4-(oxolan-2-ylmethoxy)pyridin-2-yl]-1,2,4-oxadiazole;
5-tert-butyl-3-[5-cyclopropyl-4-[[(2S)-1-methylpyrrolidin-2-yl]methoxy]pyridin-2-yl]-1,2,4-oxadiazole;
5-tert-butyl-3-[5-cyclopropyl-4-(oxetan-2-ylmethoxy)pyridin-2-yl]-1,2,4-oxadiazole;
5-tert-butyl-3-[5-cyclopropyl-4-(4-fluorophenoxy)pyridin-2-yl]-1,2,4-oxadiazole;
5-tert-butyl-3-[5-methylsulfonyl-4-(2,2,2-trifluoroethoxy)pyridin-2-yl]-1,2,4-oxadiazole;
5-tert-butyl-3-[5-chloro-4-(2,2,2-trifluoroethoxy)pyridin-2-yl]-1,2,4-oxadiazole;
3-[5-chloro-4-(2,2,2-trifluoroethoxy)pyridin-2-yl]-5-cyclopropyl-1,2,4-oxadiazole;
5-cyclopropyl-3-[5-cyclopropyl-4-(2,2,2-trifluoroethoxy)pyridin-2-yl]-1,2,4-oxadiazole;
5-tert-butyl-3-[5-cyclopropyl-4-(4-methylsulfonylphenoxy)pyridin-2-yl]-1,2,4-oxadiazole;
5-tert-butyl-3-(5-cyclopropyl-4-cyclopropylsulfonylpyridin-2-yl)-1,2,4-oxadiazole;
5-tert-butyl-3-[5-cyclopropyl-4-(2-ethoxyethoxy)pyridin-2-yl]-1,2,4-oxadiazole;
5-tert-butyl-3-[5-cyclopropyl-4-(1-methoxybutan-2-yloxy)pyridin-2-yl]-1,2,4-oxadiazole;
5-tert-butyl-3[5-cyclopropyl-4-[2-[(2-methylpropan-2-yl)oxy]ethoxy]pyridin-2-yl]-1,2,4-oxadiazole;
5-tert-butyl-3-[5-cyclopropyl-4-[1-[(2-methylpropan-2-yl)oxy]propan-2-yloxy]pyridin-2-yl]-1,2,4-oxadiazole;
5-tert-butyl-3-[5cyclopropyl-4-(1-methoxypropan-2-yloxy)pyridin-2-yl]-1,2,4-oxadiazole;
5-tert-butyl-3-[5-cyclopropyl-4-(3-methoxybutoxy)pyridin-2-yl]-1,2,4-oxadiazole;
5-tert-butyl-3-[5-cyclopropyl-4-(oxetan-3-ylmethoxy)pyridin-2-yl]-1,2,4-oxadiazole;
5-cyclopropyl-3-[5-cyclopropyl-4-[(2S)-1,1,1-trifluoropropan-2-yl]oxypyridin-2-yl]-1,2,4-oxadiazole;
5-tert-butyl-3-[5-cyclopropyl-4-(2-pyrrolidin-1-ylethoxy)pyridin-2-yl]-1,2,4-oxadiazole;

5-tert-butyl-3-[5-cyclopropyl-4-(2-piperidin-l-ylethoxy)pyridin-2-yl]-1,2,4-oxadiazole;
5-tert-butyl-3-[5-cyclopropyl-4-(1-piperidin-1-ylpropan-2-yloxy)pyridin-2-yl]-1,2,4-oxadiazole;
5-tert-butyl-3-[5-cyclopropyl-4-[(1-methylpiperidin-2-yl)methoxy]pyridin-2-yl]-1,2,4-oxadiazole;
2-[2-(5-tert-butyl-1,2,4-oxadiazol-3-yl)-5-cyclopropylpyridin-4-yl]oxy-N,N-diethylpropan-1-amine;
3-[[2-(5-tert-butyl-1,2,4-oxadiazol-3-yl)-5-cyclopropylpyridin-4-yl]oxyethyl]morpholine;
4-[2-[2-(5-tert-butyl-1,2,4-oxadiazol-3-yl)-5-cyclopropylpyridin-4-yl]oxyethyl]morpholine;
5-tert-butyl-3-[5-cyclopropyl-4-[(3-fluorooxetan-3-yl)methoxy]pyridin-2-yl]-1,2,4-oxadiazole;
5-tert-butyl-3-[5-cyclopropyl-4-[(2,5-dimethyl-1,3-oxazol-4-yl)methoxy]pyridin-2-yl]-1,2,4-oxadiazole;
5-tert-butyl-3-[5-cyclopropyl-4-[(5-methyl-1,2-oxazol-3-yl)methoxy]pyridin-2-yl]-1,2,4-oxadiazole;
5-tert-butyl-3-[5-cyclopropyl-4-(3-methylsulfonylphenoxy)pyridin-2-yl]-1,2,4-oxadiazole;
5-tert-butyl-3-(6-chloro-5-cyclopropyl-4-(4-fluorobenzyloxy)pyridin-2-yl)-1,2,4-oxadiazole;
2-tert-butyl-5-[5-cyclopropyl-4-(2,2,2-trifluoroethoxy)pyridin-2-yl]-1,3,4-oxadiazole;
5-tert-butyl-3-[5-cyclopropyl-4-(2,2-difluoroethoxy)pyridin-2-yl]-1,2,4-oxadiazole;
5-tert-butyl-3-[5-cyclopropyl-4-(2-fluoroethoxy)pyridin-2-yl]-1,2,4-oxadiazole;
5-tert-butyl-3-[5-cyclopropyl-4-(pyridin-2-ylmethoxy)pyridin-2-yl]-1,2,4-oxadiazole;
5-tert-butyl-3-[5-cyclopropyl-4-[(5-fluoropyridin-2-yl)methoxy]pyridin-2-yl]-1,2,4-oxadiazole;
5-tert-butyl-3-[5-cyclopropyl-4-(pyridin-3-ylmethoxy)pyridin-2-yl]-1,2,4-oxadiazole;
2-tert-butyl-5-[5-cyclopropyl-4-[(2S)-1,1,1-trifluoropropan-2-yl]oxypyridin-2-yl]-1,3,4-oxadiazole;
3-tert-butyl-5-[5-cyclopropyl-4-[[(2S)-1-methylpyrrolidin-2-yl]methoxy]pyridin-2-yl]-1,2,4-oxadiazole; and
3-tert-butyl-5-(5-cyclopropyl-4-(2,2-difluoroethoxy)pyridin-2-yl)-1,2,4-oxadiazole;
or a pharmaceutically acceptable salt thereof.

2. A compound selected from the group consisting of:
5-tert-butyl-3-[5-cyclopropyl-4-(2,2,2-trifluoroethoxy)pyridin-2-yl]-1,2,4-oxadiazole;
3 -tert-butyl-5-[5-cyclopropyl-4-(2,2,2-trifluoroethoxy)pyridin-2-yl]-1,2,4-oxadiazole;
5-tert-butyl-3-[5-cyclopropyl-4-[(3-methyloxetan-3-yl)methoxy]pyridin-2-yl]-1,2,4-oxadiazole;
5-tert-butyl-3-[5-cyclopropyl-4-(oxolan-2-ylmethoxy)pyridin-2-yl]-1,2,4-oxadiazole;
5-tert-butyl-3-[5-cyclopropyl-4-(4-fluorophenoxy)pyridin-2-yl]-1,2,4-oxadiazole;
5-tert-butyl-3-[5-cyclopropyl-4-(2-ethoxyethoxy)pyridin-2-yl]-1,2,4-oxadiazole;
5-tert-butyl-3-[5-cyclopropyl-4-(3-methoxybutoxy)pyridin-2-yl]-1,2,4-oxadiazole;
5-tert-butyl-3-[5-cyclopropyl-4-(oxetan-3-ylmethoxy)pyridin-2-yl]-1,2,4-oxadiazole;
5-tert-butyl-3-[5-cyclopropyl-4-[(5-fluoropyridin-2-yl)methoxy]pyridin-2-yl]-1,2,4-oxadiazole;
3-tert-butyl-5-(5-cyclopropyl-4-(2,2-difluoroethoxy)pyridin-2-yl)-1,2,4-oxadiazole;
or a pharmaceutically acceptable salt thereof.

3. A compound of claim 2 selected from the group consisting of:
5-tert-butyl-3-[5-cyclopropyl-4-(2,2,2-trifluoroethoxy)pyridin-2-yl]-1,2,4-oxadiazole;
5-tert-butyl-3-[5-cyclopropyl-4-[(3-methyloxetan-3-yl)methoxy]pyridin-2-yl]-1,2,4-oxadiazole;
5-tert-butyl-3-[5-cyclopropyl-4-(oxolan-2-ylmethoxy)pyridin-2-yl]-1,2,4-oxadiazole;
5-tert-butyl-3-[5-cyclopropyl-4-(4-fluorophenoxy)pyridin-2-yl]-1,2,4-oxadiazole;
5-tert-butyl-3-[5-cyclopropyl-4-(2-ethoxyethoxy)pyridin-2-yl]-1,2,4-oxadiazole;
5-tert-butyl-3-[5-cyclopropyl-4-(3-methoxybutoxy)pyridin-2-yl]-1,2,4-oxadiazole;
5-tert-butyl-3-[5-cyclopropyl-4-(oxetan-3-ylmethoxy)pyridin-2-yl]-1,2,4-oxadiazole;
5-tert-butyl-3-[5-cyclopropyl-4-[(5-fluoropyridin-2-yl)methoxy]pyridin-2-yl]-1,2,4-oxadiazole;
or a pharmaceutically acceptable salt thereof.

4. A compound of claim 2 selected from the group consisting of:
3-tert-butyl-5-(5-cyclopropyl-4-(2,2,2-trifluoroethoxy)pyridin-2-yl)-1,2,4-oxadiazole;
3-tert-butyl-5-(5-cyclopropyl-4-(2,2-difluoroethoxy)pyridin-2-yl)-1,2,4-oxadiazole;
or a pharmaceutically acceptable salt thereof.

5. A pharmaceutical composition comprising a compound of claim 1, or a pharmaceutically acceptable salt thereof, and a therapeutically inert carrier.

6. A pharmaceutical composition comprising a compound of claim 2, or a pharmaceutically acceptable salt thereof, and a therapeutically inert carrier.

7. A pharmaceutical composition comprising a compound of claim 3, or a pharmaceutically acceptable salt thereof, and a therapeutically inert carrier.

8. A pharmaceutical composition comprising a compound of claim 4, or a pharmaceutically acceptable salt thereof, and a therapeutically inert carrier.

9. A compound, which is 3-tert-butyl-5-[5-cyclopropyl-4-(2,2,2-trifluoroethoxy)pyridin-2-yl]-1,2,4-oxadiazole, or a pharmaceutically acceptable salt thereof.

10. A pharmaceutical composition comprising a compound of claim 9, or a pharmaceutically acceptable salt thereof, and a therapeutically inert carrier.

* * * * *